United States Patent
Nanson et al.

(10) Patent No.: US 11,603,431 B2
(45) Date of Patent: Mar. 14, 2023

(54) ORGANIC SEMICONDUCTORS

(71) Applicant: Raynergy Tek Incorporation, Hsinchu (TW)

(72) Inventors: Lana Nanson, Southampton (GB); Nicolas Blouin, Darmstadt (DE); William Mitchell, Chandler's Ford (GB); Joseph Cameron, Glasgow (GB); Peter Skabara, Glasgow (GB)

(73) Assignee: RAYNERGY TEK INCORPORATION, Hsinchu (TW)

( * ) Notice: Subject to any disclaimer, the term of this patent is extended or adjusted under 35 U.S.C. 154(b) by 949 days.

(21) Appl. No.: 16/075,396

(22) PCT Filed: Dec. 30, 2016

(86) PCT No.: PCT/EP2016/002189
§ 371 (c)(1),
(2) Date: Aug. 3, 2018

(87) PCT Pub. No.: WO2017/133752
PCT Pub. Date: Aug. 10, 2017

(65) Prior Publication Data
US 2019/0040188 A1 Feb. 7, 2019

(30) Foreign Application Priority Data
Feb. 4, 2016 (EP) .................................. 16154179

(51) Int. Cl.
*C08G 61/12* (2006.01)
*H01L 51/00* (2006.01)
(Continued)

(52) U.S. Cl.
CPC ......... *C08G 61/126* (2013.01); *C07D 487/02* (2013.01); *C07D 487/04* (2013.01);
(Continued)

(58) Field of Classification Search
None
See application file for complete search history.

(56) References Cited

U.S. PATENT DOCUMENTS

2006/0081839 A1 4/2006 Jeong
2006/0113527 A1 6/2006 Han
(Continued)

FOREIGN PATENT DOCUMENTS

CN 105143190 A 12/2015
CN 105885640 A 8/2016
(Continued)

OTHER PUBLICATIONS

Machine English translation of Okubo et al. (JP 5838975 B2). Sep. 29, 2021.*
(Continued)

*Primary Examiner* — Jay Yang
(74) *Attorney, Agent, or Firm* — WPAT, PC

(57) ABSTRACT

The invention relates to novel compounds containing one or more units derived from 2,6-disubstituted-[1,5]naphthyridine or 1,6-disubstituted-1H-[1,5]naphthyridine-2-one, to methods for their preparation and educts or intermediates used therein, to mixtures and formulations containing them, to the use of the compounds, mixtures and formulations as organic semiconductors in organic electronic (OE) devices, especially in organic photovoltaic (OPV) devices and organic photodetectors (OPD), and to OE, OPV and OPD devices comprising these compounds, mixtures or formulations.

27 Claims, 2 Drawing Sheets

(51) Int. Cl.
*H01L 51/05* (2006.01)
*C07D 487/04* (2006.01)
*C07D 519/00* (2006.01)
*C07D 487/02* (2006.01)

(52) U.S. Cl.
CPC ......... *C07D 519/00* (2013.01); *C08G 61/122* (2013.01); *H01L 51/0036* (2013.01); *H01L 51/0043* (2013.01); *H01L 51/0068* (2013.01); *H01L 51/0071* (2013.01); *H01L 51/0072* (2013.01); *H01L 51/0073* (2013.01); *H01L 51/0558* (2013.01); *C08G 2261/122* (2013.01); *C08G 2261/124* (2013.01); *C08G 2261/146* (2013.01); *C08G 2261/1424* (2013.01); *C08G 2261/3241* (2013.01); *C08G 2261/3243* (2013.01); *C08G 2261/344* (2013.01); *C08G 2261/364* (2013.01); *C08G 2261/414* (2013.01); *C08G 2261/92* (2013.01); *Y02E 10/549* (2013.01)

(56) References Cited

U.S. PATENT DOCUMENTS

| | | | | |
|---|---|---|---|---|
| 2008/0116789 | A1* | 5/2008 | Yamaguchi | C07D 519/00 313/504 |
| 2013/0187134 | A1 | 7/2013 | Chung | |

FOREIGN PATENT DOCUMENTS

| | | |
|---|---|---|
| JP | 2003017062 A | 1/2003 |
| JP | 5838975 B2 * | 11/2015 |
| WO | 2004043458 A1 | 5/2004 |
| WO | 2007078179 A1 | 7/2007 |
| WO | 2007133637 A1 | 11/2007 |
| WO | 2009151991 A1 | 12/2009 |
| WO | 2010058314 A1 | 5/2010 |
| WO | 2011004276 A1 | 1/2011 |
| WO | 2012111811 A1 | 8/2012 |
| WO | 2013182262 A1 | 12/2013 |
| WO | 2014158916 A1 | 10/2014 |
| WO | 2015015397 A1 | 2/2015 |
| WO | WO2015024848 A1 | 2/2015 |

OTHER PUBLICATIONS

Office Action issued by China National Intellectual Property Administration, dated Sep. 24, 2020.
PubChem, "3-Bromo-7-methoxy-1,5-naphthyridine", Oct. 6, 2017, C9H7BrN2O—PubChem, https://pubchem.ncbi.nlm.nih.gov/compound/129957736.
International Search Report PCT/EP2016/002189 dated Mar. 7, 2017.
Alexander M D et al.: "Designing Air and Water Stable N-Dopable Model Compounds and Polymers: Calculation of Relative Oxidative Stability", Proceedings—Electrochemical Society, Electrochemical Society, Pennington, NJ, US, vol. 2000-15, Jan. 1, 2000 (Jan. 1, 2000), pp. 128-131, XP008051597, ISSN: 0161-6374.
Sheo B. Singh et al: "Tricyclic 1,5-naphthyridinone oxabicyclooctane-linked novel bacterial topoisomerase inhibitors as broad-spectrum antibacterial agents—SAR of left-hand-side moiety (Part-2)", Bioorganic & Medicinal Chemistry Letters, vol. 25, No. 9, May 1, 2015 (May 1, 2015), Amsterdam, NL, pp. 1831-1835, XP055347191, ISSN: 0960-894X, DOI: 10.1016/j.bmcl.2015.03.044.
Czuba, W.: "Bromination of 1,5-naphthyridine in fuming H2SO4", Bulletin De L'Academie Polonaise Des Sciences, Serie Des-scienceschimiques, 1963, pp. 375-380, XP009193528.
Database Registry Chemical Abstracts Service, Columbus, Ohio, US; Chemical Catalog Supplier: Abby Pharmatech, LLC: "1,5-Naphthyridine, 3-bromo-7-methoxy-", XP055346855 (1 page).

* cited by examiner

ORGANIC SEMICONDUCTORS

TECHNICAL FIELD

The invention relates to novel compounds containing one or more units derived from 2,6-disubstituted-[1,5]naphthyridine or 1,6-disubstituted-1H-[1,5]naphthyridine-2-one, to methods for their preparation and educts or intermediates used therein, to mixtures and formulations containing them, to the use of the compounds, mixtures and formulations as organic semiconductors in organic electronic (OE) devices, especially in organic photovoltaic (OPV) devices and organic photodetectors (OPD), and to OE, OPV and OPD devices comprising these compounds, mixtures or formulations.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The organic semiconducting materials are typically present in the electronic device in the form of a thin layer.

The performance of OFET devices is principally based upon the charge carrier mobility of the semiconducting material and the current on/off ratio, so the ideal semiconductor should have a low conductivity in the off state, combined with a high charge carrier mobility ($>1 \times 10^{-3}$ cm$^2$ V$^{-1}$ s$^{-1}$). In addition, it is important that the semiconducting material is relatively stable to oxidation i.e. it has a high ionisation potential, as oxidative doping leads to reduced device performance, for example increased off current and threshold voltage shift. Further requirements for the semiconducting material to have include good processability, especially for large-scale production of thin-film layers and desired patterns, and high stability, thin-film uniformity and integrity of the organic semiconductor layer.

Another particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies over 10%.

The conjugated polymer serves as the main absorber of the solar energy in the bulk-heterojunction blend layer and therefore a low band gap is a basic requirement of the ideal polymer design to absorb the maximum of the solar spectrum.

A commonly used strategy to narrow the band gap of polymers is to utilize an alternating copolymer consisting of both electron rich donor units and electron deficient acceptor units within the polymer backbone. However, the ideal polymer which combines high efficiency, facile synthesis and scalable has yet to be found.

Thus there is still a need for organic semiconducting (OSC) polymers which are easy to synthesize, especially by methods suitable for mass production, show good structural organization and film-forming properties, exhibit good electronic properties, especially a high charge carrier mobility, a good processability, especially a high solubility in organic solvents, and high stability in air. Especially for use in OPV cells, there is a need for OSC materials having a low bandgap, which enable improved light harvesting by the photoactive layer and can lead to higher cell efficiencies, compared to the polymers from prior art.

It was an aim of the present invention to provide compounds for use as organic semiconducting materials in OE devices like OFETs, OPDs and OPV devices, which are easy to synthesize, especially by methods suitable for mass production, which show especially good processability, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing compounds having a divalent unit derived from 2,6-disubstituted-[1,5]naphthyridine or 1,6-disubstituted-1H-[1,5]naphthyridine-2-one.

In case of the 2,6-disubstituted-[1,5]naphthyridines, the ring system incorporating two fused six-membered rings, together with the introduction of substituents, like for example alkoxy groups, to the 2,6-position, is expected to lead to an alternative solubility and morphology profile, which has an impact on the compound's electrical properties, and consequently its OFET, OPD and/or OPV device performance.

In case of the 1-6-disubstituted-1H-[1,5]naphthyridin-2-ones, incorporation of this unsymmetrical unit into small molecules and polymers is also expected to lead to alternative solubility and morphology profiles. As with 2,6-disubstituted-[1,5]naphthyridine, this difference will have an impact on the compound's electrical properties, and consequently its OFET, OPD and/or OPV device performance.

WO 2015/015397 A1 discloses the use of 1,5-naphthyridines, which are connected to further aryl or heteroaryl units, as acceptor molecules in OE devices. However, the document does not disclose or suggest any further substitution on the 1,5-naphthyridine core.

JP09003171 also claims the use of the 1,5-naphthyridine but again does not claim substitution of the ring other than to link the unit within the polymer chain. JP09003171 also states the inclusion of an N-oxide unit within the polymer chain.

Few examples of materials containing the unsymmetrical 1-6-disubstituted-1H-[1,5]naphthyridin-2-one core exist, and the publications that do discuss this structure are aimed at a pharmaceutical target. See for example J. Med. Chem., 2014, 57 (11), 4889-4905.

However, compounds as disclosed and claimed hereinafter and their use as organic semiconductors have not been disclosed or suggested in prior art so far.

SUMMARY

The invention relates to compounds comprising one or more divalent units of formula I1 or I2

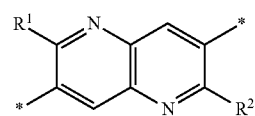

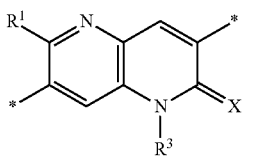

wherein the individual radicals, independently of each other and on each occurrence identically or differently, have the following meanings X O or S, $R^1$, $R^2$, $R^3$ H, halogen, CN, straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)O—, —O—C(=O)—, —$NR^0$—, —$SiR^0R^{00}$—, —$CF_2$—, —$CR^0=CR^{00}$—, —$CY^1=CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, L F, Cl, —CN, —NC, —NCO, —NCS, —OCN, —SCN, —C(=O)$NR^0R^{00}$, —C(=O)$X^0$, —C(=O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, or carbyl or hydrocarbyl with 1 to 20 C atoms that is optionally substituted and optionally comprises one or more hetero atoms, preferably F, alkyl, alkoxy, thioalkyl, alkylcarbonyl, alkoxycarbonyl, alkylcarbonyloxy or alkoxycarbonyloxy with 1 to 20 C atoms that is optionally fluorinated, $Y^1$, $Y^2$ H, F, Cl or CN, $X^0$ halogen, $R^0$, $R^{00}$ H or alkyl with 1 to 12 C-atoms.

The invention further relates to a formulation comprising one or more compounds as described above and below and one or more solvents, preferably selected from organic solvents.

The invention further relates to an organic semiconducting formulation comprising one or more compounds as described above and below, and further comprising one or more organic binders or precursors thereof, preferably having a permittivity c at 1,000 Hz and 20° C. of 3.3 or less, and optionally one or more solvents.

The invention further relates to the use of the units of formula I1 and I2 as repeating units in conjugated polymers.

The invention further relates to a compound as described above and below which is a conjugated polymer comprising one or more repeating units, wherein said repeating units contain a unit of formula I1 and/or I2 and optionally contain one or more units selected from arylene and heteroarylene units that are optionally substituted, and wherein at least one repeating unit in the conjugated polymer contains at least one unit of formula I1 or I2.

The invention further relates to the use of units of formula I1 and I2 in or as repeating units having electron acceptor property in conjugated polymers.

The invention further relates to a conjugated polymer comprising one or more electron acceptor repeating units comprising a unit of formula I1 and/or I2, and preferably further comprising one or more repeating units having electron donor property.

The invention further relates to a monomer containing a unit of formula I1 and/or I2, and optionally containing one or more additional arylene or heteroarylene units, and further containing one or more reactive groups which can be reacted to form a conjugated polymer as described above and below.

The invention further relates to the use of a compound as described above and below as electron acceptor or n-type semiconductor.

The invention further relates to the use of a conjugated polymer as described above and below as semiconductor, preferably as electron donor or p-type semiconductor.

The invention further relates to the use of a compound as described above and below as electron donor or electron acceptor component in a semiconducting material, formulation, polymer blend, device or component of a device.

The invention further relates to a semiconducting material, formulation, polymer blend, device or component of a device comprising a compound as described above and below as electron donor component, and preferably further comprising one or more compounds having electron acceptor properties.

The invention further relates to a mixture, which may also be a polymer blend, comprising one or more compounds as described above and below, and further comprising one or more additional compounds selected from compounds having one or more of semiconducting, charge transport, hole or electron transport, hole or electron blocking, electrically conducting, photoconducting or light emitting properties.

The invention further relates to a mixture comprising one or more compounds as described above and below, and further comprising one or more n-type organic semiconductors, preferably selected from fullerenes or substituted fullerenes.

The invention further relates to a formulation comprising one or more compounds or mixtures as described above and below, and further comprising one or more solvents, preferably selected from organic solvents.

The invention further relates to an optical, electrooptical, electronic, electroluminescent or photoluminescent device, or a component thereof, or an assembly comprising it, which is prepared using a formulation according to the present invention.

The invention further relates to the use of a compound or mixture as described above and below as semiconducting, charge transport, electrically conducting, photoconducting or light emitting material, or in an optical, electrooptical, electronic, electroluminescent or photoluminescent device, or in a component of such a device or in an assembly comprising such a device or component The invention further relates to a semiconducting, charge transport, electrically conducting, photoconducting or light emitting material comprising a compound or mixture as described above and below.

The invention further relates to an optical, electrooptical, electronic, electroluminescent or photoluminescent device, or a component thereof, or an assembly comprising it, which comprises a compound or mixture as described above and below, or comprises a semiconducting, charge transport, electrically conducting, photoconducting or light emitting material as described above and below.

The optical, electrooptical, electronic, electroluminescent and photoluminescent device includes, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye-sensitized solar cells (DSSC), perovskite-based solar cells, laser diodes, Schottky diodes, photoconductors and photodetectors.

Preferred devices are OFETs, OTFTs, OPVs, OPDs and OLEDs, in particular bulk heterojunction (BHJ) OPVs or inverted BHJ OPVs.

Further preferred is the use of a compound or mixture as described above and below as dye in a DSSC or a perovskite-based solar cell. Further preferred is a DSSC or perovskite-based solar cells comprising a compound or mixture as described above and below.

The component of the above devices includes, without limitation, charge injection layers, charge transport layers, interlayers, planarising layers, antistatic films, polymer electrolyte membranes (PEM), conducting substrates and conducting patterns.

The assembly comprising such a device or component includes, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds, mixtures and formulations of the present invention can be used as electrode materials in batteries and in components or devices for detecting and discriminating DNA sequences.

The invention further relates to a bulk heterojunction which comprises, or is being formed from, a mixture comprising one or more compounds according to the present invention and one or more n-type organic semiconductors that are preferably selected from fullerenes or substituted fullerenes. The invention further relates to a bulk heterojunction (BHJ) OPV device or inverted BHJ OPV device, comprising such a bulk heterojunction.

TERMS AND DEFINITIONS

Figure 1A:
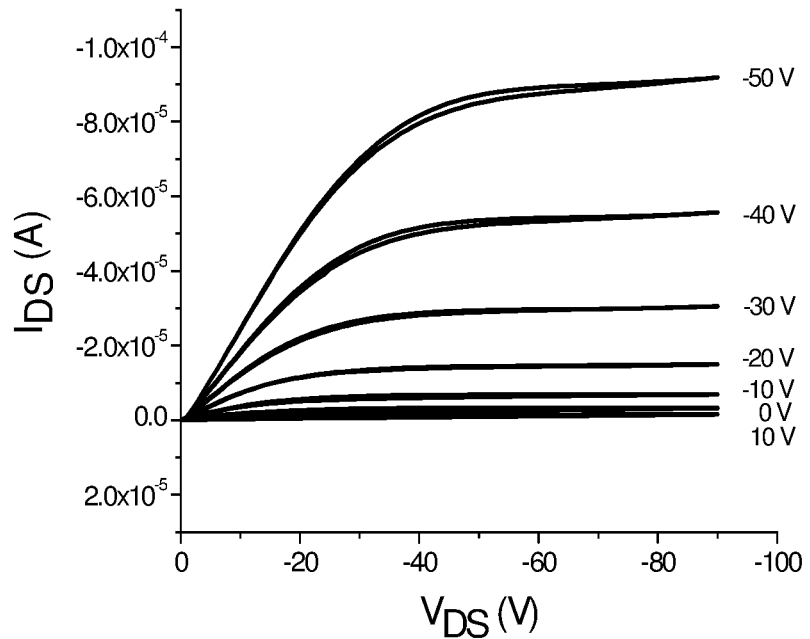
FIG. 1a shows the output graph of an OFET prepared according to Use Example A.

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, like for example a unit of formula I or a polymer of formula III or IV, or their subformulae, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^5$ or $R^6$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19 Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from F, Cl, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 20 C atoms that is optionally substituted and optionally comprises one or more hetero atoms, and is preferably F, alkyl, alkoxy, thioalkyl, alkylcarbonyl, alkoxycarbonyl, alkylcarbonyloxy or alkoxycarbonyloxy with 1 to 20 C atoms that is optionally fluorinated, X$^0$ is halogen, preferably F, Cl or Br, and R$^0$, R$^{00}$ have the meanings given above and below, and preferably denote H or alkyl with 1 to 12 C atoms.

Preferred substituents L are selected from halogen, most preferably F, or alkyl, alkoxy, oxaalkyl, thioalkyl, fluoroalkyl and fluoroalkoxy with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal CH$_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more CH$_2$ groups are replaced by —CH═CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one CH$_2$ group is replaced by —O— and one CH$_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more CH$_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one CH$_2$ group is replaced by —S—, is preferably straight-chain thiomethyl (—SCH$_3$), 1-thioethyl (—SCH$_2$CH$_3$), 1-thiopropyl (═SCH$_2$CH$_2$CH$_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the CH$_2$ group adjacent to the sp$^2$ hybridised vinyl carbon atom is replaced.

A fluoroalkyl group is perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the alkyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

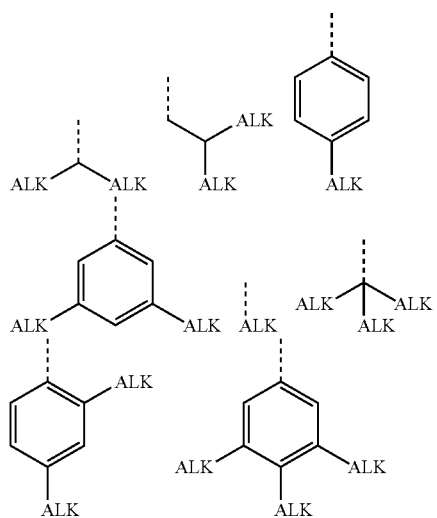

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, if an aryl(oxy) or heteroaryl(oxy) group is "alkylated or alkoxylated", this means that it is substituted with one or more alkyl or alkoxy groups having from 1 to 20 C-atoms and being straight-chain or branched and wherein one or more H atoms are optionally substituted by an F atom.

Above and below, $Y^1$ and $Y^2$ are independently of each other H, F, Cl or CN.

As used herein, —CO—, —C(=O)— and —C(O)— will be understood to mean a carbonyl group, i.e. a group having the structure

As used herein, C=$CR^1R^2$ will be understood to mean an ylidene group, i.e. a group having the structure

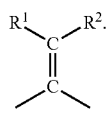

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer is preferably Br or I.

DETAILED DESCRIPTION

The polymers of the present invention are easy to synthesize and exhibit advantageous properties. They show good processability for the device manufacture process, high solubility in organic solvents, and are especially suitable for large scale production using solution processing methods. At the same time, the co-polymers derived from monomers of the present invention and electron donor monomers show low bandgaps, high charge carrier mobilities, high external quantum efficiencies in BHJ solar cells, good morphology when used in p/n-type blends e.g. with fullerenes, high oxidative stability, a long lifetime in electronic devices, and are promising materials for organic electronic OE devices, especially for OPV devices with high power conversion efficiency.

The polymers according to the present invention are especially suitable as p-type semiconductors for the preparation of blends of p-type and n-type semiconductors which are suitable for use in BHJ photovoltaic devices.

Besides, the polymers of the present invention show the following advantageous properties:

i) Compared to unsubstituted 1,5-naphthyridine, substitution on the 2,6-positions, or substitution on the 6-position along with carbonyl functionalisation of the 2-position, is expected to lead to alternative solubility and morphology profiles. Such differences are expected to have an impact on the OFET and/or OPV device fabrication process and performance.

ii) Solubility can be introduced into the polymer or compound by inclusion of functional groups or solubility increasing groups on the 2,6-disubstituted-[1,5]naphthyridine and 1-6-disubstituted-1H-[1,5]naphthyridin-2-one cores.

iii) The units of 2,6-disubstituted [1,5]naphthyridine and 1,6-disubstituted1H-[1,5]naphthyridin-2-one cores are planar structures that enable strong pi-pi stacking in the solid state leading to improved charge transport properties in the form of higher charge carrier mobility.

iv) Fine-tuning of the electronic energies (HOMO/LUMO levels) by either careful selection of arylene or heteroarylene units on each side of 2,6-disubstituted-[1,5]naphthyridine and 1-6-disubstituted-1H-[1,5]naphthyridin-2-one cores, or co-polymerisation with appropriate co-monomer(s), can afford candidate materials for OFET and/or OPV applications.

v) Alternatively, fine-tuning of the electronic energies (HOMO/LUMO levels) and solubility of the resulting polymer or compound can be achieved by careful selection of different arylene or heteroarylene units generating asymmetric compounds or repeat units in the polymer backbone, for example by pre-flanking the symmetrical 2,6-disubstituted-[1,5]napthyridine unit with different arylene or heteroarylene groups, to bring more disorder to the polymer and so increase solubility.

Preferably X in the units of formula I2 is O.

Preferably $R^3$ in the units of formula I1 and I2 denotes H or is selected from the group consisting of alkyl, alkoxy and thioalkyl with 1 to 30, preferably 1 to 20, C atoms, each of which is straight-chain, branched or cyclic and is unsubstituted or substituted by one or more F atoms, Preferably $R^1$ and $R^2$ in the units of formula I1 and I2 are different from H.

Preferably $R^1$ and $R^2$ in the units of formula I1 and I2 are selected from the following groups or any combination thereof:

the group consisting of alkyl, alkoxy and thioalkyl with 1 to 30, preferably 1 to 20, C atoms, each of which is straight-chain, branched or cyclic and is unsubstituted or substituted by one or more F atoms, the group consisting of alkylcarbonyl, alkylcarbonyloxy, alkyloxycarbonyl and alkoxycarbonyloxy with 2 to 20 C atoms, each of which is straight-chain or branched and is unsubstituted or substituted by one or more F atoms, the group consisting of aryl, aryloxy, heteroaryl and heteroaryloxy, each of which has 4 to 20 ring atoms and optionally contains fused rings and is unsubstituted or substituted by one or more groups L as defined in formula I1, wherein said groups L are preferably selected from F, alkyl, alkoxy, thioalkyl, alkylcarbonyl, alkoxycarbonyl, alkylcarbonyloxy or alkoxycarbonyloxy each having 1 to 20 C atoms and being optionally fluorinated.

If $R^1$ or $R^2$ denote an aryl(oxy) or heteroaryl(oxy) group, it is preferably selected from phenyl, pyrrole, furan, pyridine, thiazole, thiophene, thieno[3,2-b]thiophene or thieno[2,3-b]thiophene, each of which is optionally fluorinated, alkylated or alkoxylated.

In another preferred embodiment of the present invention, $R^1$ and/or $R^2$ denote straight-chain, branched or cyclic alkyl with 1 to 20 C-atoms wherein one or more $CH_2$ or $CH_3$ groups are substituted by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms.

Further preferred cationic groups are selected from the group consisting of the following formulae

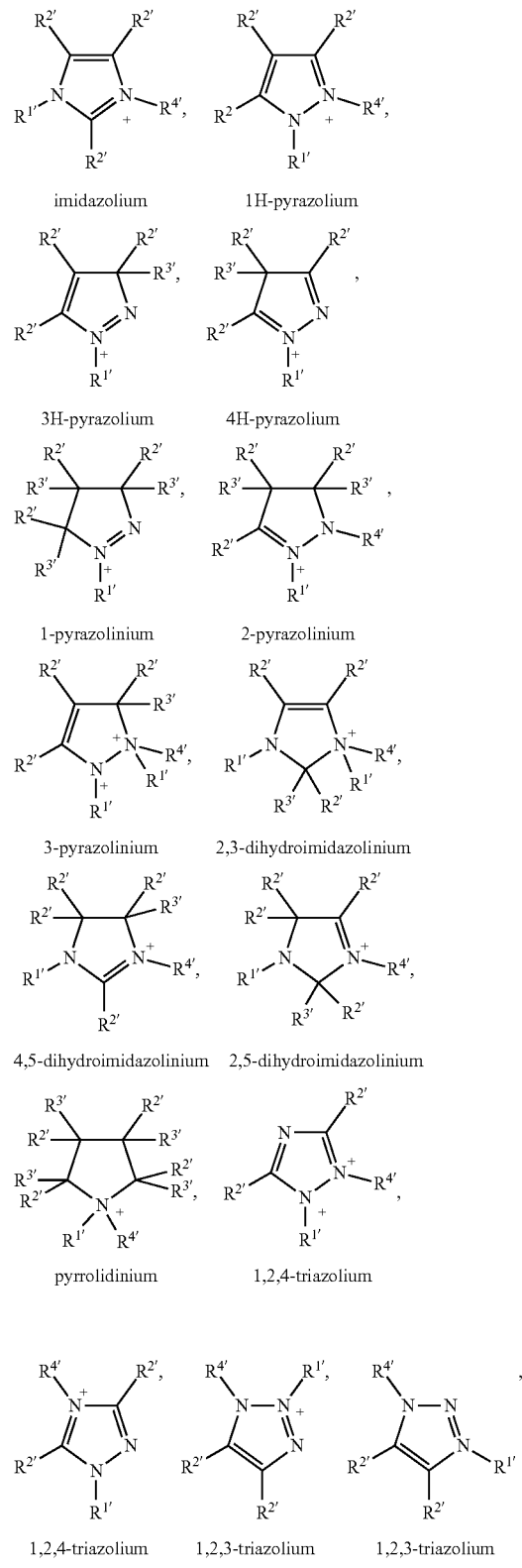

imidazolium    1H-pyrazolium 3H-pyrazolium    4H-pyrazolium 1-pyrazolinium    2-pyrazolinium 3-pyrazolinium    2,3-dihydroimidazolinium 4,5-dihydroimidazolinium    2,5-dihydroimidazolinium pyrrolidinium    1,2,4-triazolium 1,2,4-triazolium    1,2,3-triazolium    1,2,3-triazolium

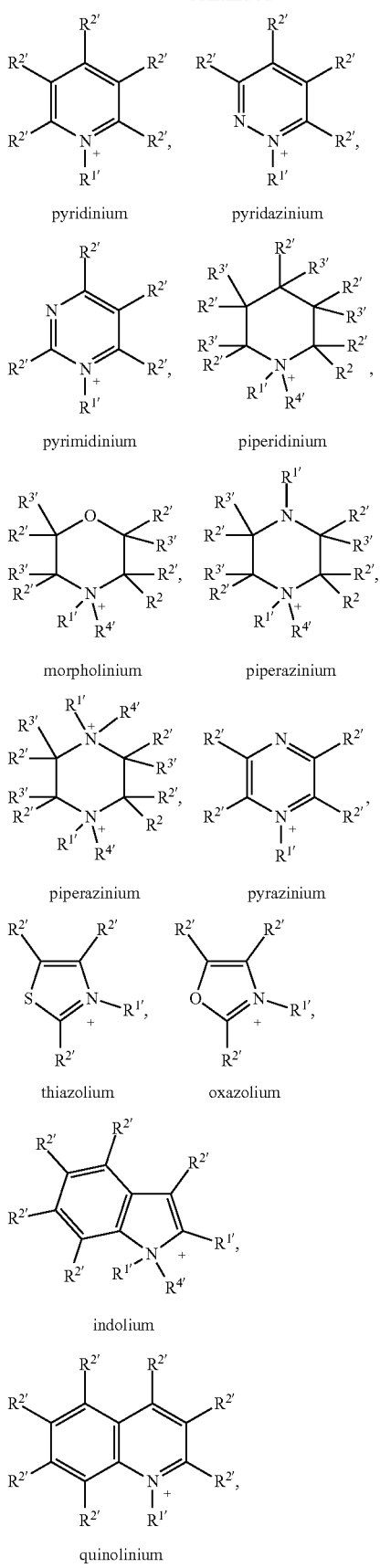

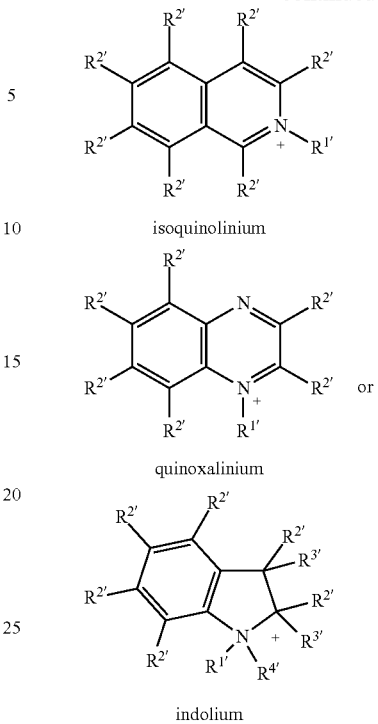

wherein $R^{1\prime}$, $R^{2\prime}$, $R^{3\prime}$ and $R^{4\prime}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents L as defined below, or denote a link to the respective group $R^{1-4}$.

In the above cationic groups of the above-mentioned formulae any one of the groups $R^{1\prime}$, $R^{2\prime}$, $R^{3\prime}$ and $R^{4\prime}$ (if they replace a $CH_3$ group) can denote a link to the group $R^1$, or two neighbored groups $R^{1\prime}$, $R^{2\prime}$, $R^{3\prime}$ or $R^{4\prime}$ (if they replace a $CH_2$ group) can denote a link to the respective group $R^{1-4}$.

The anionic group is preferably selected from the group consisting of borate, imide, phosphate, sulfonate, sulfate, succinate, naphthenate or carboxylate, very preferably from phosphate, sulfonate or carboxylate.

The compound according to the present invention includes small molecules, monomers, oligomers and polymers.

In a preferred embodiment of the present invention the compound is a conjugated polymer comprising one or more units of formula I1 or I2 as defined above and below.

Preferably the conjugated polymer according to the present invention comprises one or more repeating units of formula II1 or II2, and optionally one or more repeating units of formula II3:

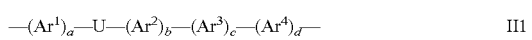    II1

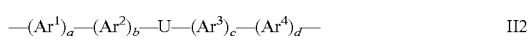    II2

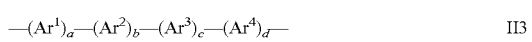    II3 wherein the individual radicals, independently of each other and on each occurrence identically or differently, have the following meanings
U a unit of formula I1 or I2 as defined above and below,
$Ar^{1-4}$ arylene or heteroarylene that is different from U, has 5 to 30 ring atoms, and is optionally substituted by one or more groups L,
$R^5$ has one of the meanings of L or its preferred meanings as described above and below,
a, b, c, d are on each occurrence identically or differently 0 or 1, wherein in formula II3 a+b+c+d≥1.

Preferably the conjugated polymer comprises one or more repeating units of formula II1 or II2 wherein a+b+c+d≥1.

Further preferably at least one of $Ar^1$, $Ar^2$, $Ar^3$ and $Ar^4$ is an arylene or heteroarylene group as being defined in formula II1 and having electron donor property.

Preferably L denotes F or is selected from the following groups
the group consisting of alkyl, alkoxy and thioalkyl with 1 to 20 C atoms, each of which is straight-chain, branched and cyclic and is unsubstituted or substituted by one or more F atoms,
the group consisting of alkylcarbonyl, alkylcarbonyloxy, alkyloxycarbonyl and alkoxycarbonyloxy with 2 to 20 C atoms, each of which is straight-chain or branched and is unsubstituted or substituted by one or more F atoms.

Further preferably the conjugated polymer according to the present invention is selected of formula III:

$$*\!-\!\!\left[\!-\!(A)_x\!-\!(B)_y\!-\!\right]_n\!\!-\!*\qquad\text{III}$$

wherein
A is a unit of formula I1, I2, II1 or II2 as defined above and below,
B is a unit of formula I1, I2, II1, II2 or II3 as defined above and below,
x is >0 and ≤1,
y is ≥0 and <1,
x+y is 1, and
n is an integer >1.

Preferred polymers of formula III are selected from the following formulae

[Structural formulae III1 through III8 depicted]

wherein $R^1$, $R^2$ and $R^3$ have the meanings of formula I1 or one of the preferred meanings given above and below, $Ar^1$, $Ar^2$, $Ar^3$, $Ar^4$, a, b, c and d have the meanings of formula II1 or one of the preferred meanings given above and below, and x, y and n have the meanings of formula III or one of the preferred meanings given above and below, and wherein preferably $Ar^3$ is selected from arylene or heteroarylene units as described above and below having electron donor properties.

In the polymers of formula III and III1-III8, x and y denote the mole fraction of repeating units A and B, respectively, and n denotes the degree of polymerisation or total number of repeating units A and B. These formulae include block copolymers, random or statistical copolymers and alternating copolymers of A and B, as well as homopolymers of A for the case when x>0 and y=0.

In the polymers of formula III and III1-III8, x is preferably from 0.1 to 0.9, very preferably from 0.3 to 0.7.

In the polymers of formula III and III1-III8, y is preferably from 0.1 to 0.9, very preferably from 0.3 to 0.7.

In the polymers according to the present invention, the total number of repeating units n is preferably from 2 to 10,000. The total number of repeating units n is preferably 5, very preferably 10, most preferably 50, and preferably 500, very preferably 1,000, most preferably 2,000, including any combination of the aforementioned lower and upper limits of n.

The polymers of the present invention include homopolymers and copolymers, like statistical or random copolymers, alternating copolymers and block copolymers, as well as combinations thereof.

Further preferably the conjugated polymer is selected of formula IV $$R^5\text{-chain-}R^6 \qquad \qquad IV$$

wherein "chain" denotes a polymer chain selected of formulae III and III1-III8, and $R^5$ and $R^6$ have independently of each other one of the meanings of L as defined above, or denote, independently of each other, H, F, Br, Cl, I, —CH$_2$Cl, —CHO, —CR'=CR"$_2$, —SiR'R"R'", —SiR'X'X", —SiR'R"X', —SnR'R"R'", —BR'R", —B(OR')(OR"), —B(OH)$_2$, —O—SO$_2$—R', —C≡CH, —C≡C—SiR'$_3$, —ZnX' or an endcap group, X' and X" denote halogen, R', R" and R'" have independently of each other one of the meanings of $R^0$ given in formula I1, and preferably denote alkyl with 1 to 12 C atoms, and two of R', R", R'" may also form a cyclosilyl, cyclostannyl, cycloborane or cycloboronate group with 2 to 20 C atoms together with the respective hetero atom to which they are attached.

Preferred endcap groups $R^5$ and $R^6$ are H, $C_{1-20}$ alkyl, or optionally substituted $C_{6-12}$ aryl or $C_{2-10}$ heteroaryl, very preferably H or phenyl.

In a further preferred embodiment of the present invention the compound is a monomer of formula V1 or V2

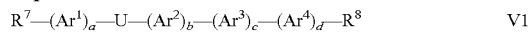

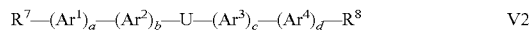

wherein U, Ar$^{1-4}$, a, b, c and d have the meanings of formula II1, or one of the preferred meanings as described above and below, and $R^7$ and $R^8$ are independently of each other selected from the group consisting of H, which is preferably an activated C—H bond, Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, Z$^{1-4}$ are selected from the group consisting of alkyl and aryl, preferably $C_{1-10}$ alkyl and $C_{6-12}$ aryl, each being optionally substituted, and two groups Z$^2$ may also form a cycloboronate group having 2 to 20 C atoms together with the B- and O-atoms.

Very preferred are monomers of formula V1 and V2 wherein a+b+c+d≥1.

Further preferred are monomers of formula V1 wherein a+b+c+d=0.

Further preferred are monomers selected from the following formulae

wherein U, Ar$^1$, Ar$^2$, R$^7$ and R$^8$ are as defined in formula V.

In a further preferred embodiment of the present invention relates the compound is a small molecule or oligomer comprising one or more units of formula I1 or I2 as defined above and below. Preferred small molecules and oligomers according to the present invention are selected of formula VI1 and VI2

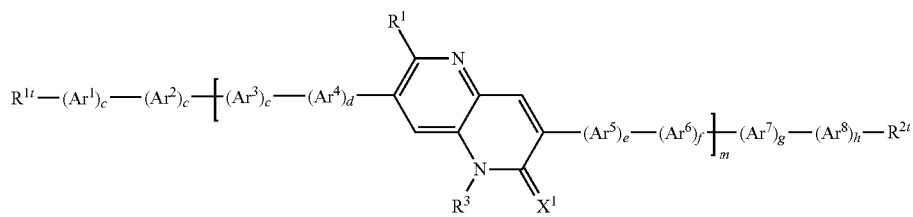

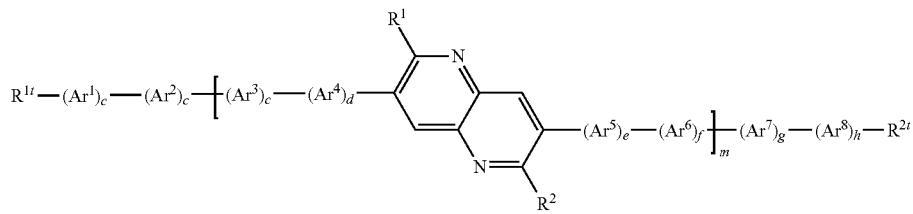

wherein the individual radicals, independently of each other and on each occurrence identically or differently, have the following meanings $Ar^{1-8}$ one of the meanings given for $Ar^1$ in formula I11 or one of its preferred meanings given above and below, or denote —CY$^1$=CY$^2$—, —C≡C— or a unit of formula I1 or I2 as defined above and below, $Y^1$, $Y^2$ H, F, Cl or CN, $R^{1\prime}$, $R^{2\prime}$ H, F, Cl, Br, —CN, —CF$_3$, R, —CF$_2$—R, —O—R, —S—R, —SO$_2$—R, —SO$_3$—R—C(O)—R, —C(S)—R, —C(O)—CF$_2$—R, —C(O)—OR, —C(S)—OR, —O—C(O)—R, —O—C(S)—R, —C(O)—SR, —S—C(O)—R, —C(O)NRR', —NR'—C(O)—R, —NHR, —NRR', —CR'=CR"R"', —C≡C—R', —C≡C—SiR'R"R"', —SiR'R"R"', —CH=C(CN)—C(O)—OR, —CH=C(COOR)$_2$, CH=C(CONRR')$_2$, CH=C(CN)(Ar$^9$),

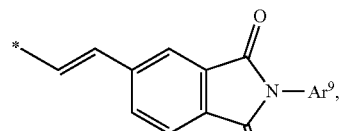

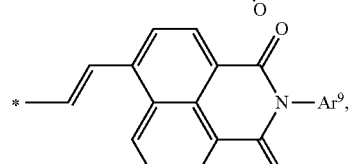

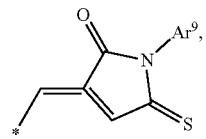

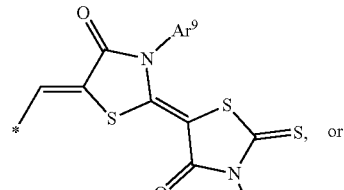

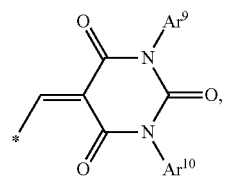

$Ar^{9,10}$ aryl or heteroaryl, each having from 4 to 30 ring atoms, optionally containing fused rings and being unsubstituted or substituted with one or more groups L as defined in formula I1, R alkyl with 1 to 20 C atoms which is straight-chain, branched or cyclic, and is unsubstituted, or substituted with one or more F or Cl atoms or CN groups, or perfluorinated, and in which one or more C atoms are optionally replaced by —O—, —S—, —C(O)—, —C(S)—, —SiR$^o$R$^{oo}$—, —NR$^o$R$^{oo}$—, —CHR$^o$=CR$^{oo}$— or —C≡C— such that O- and/or S-atoms are not directly linked to each other, $R^o$, $R^{oo}$ H or $C_{1-12}$ alkyl, R', R", R"' H or one of the meanings of R, a-h 0 or 1, with at least one of a-h being 1, m 1, 2 or 3.

Especially preferred are repeating units, monomers, oligomers, polymers and small molecules of formulae I11, I12, III, III1-III8, IV, V1, V2, V1a-V1d, V1 and V2 and their subformulae wherein one or more of $Ar^1$, $Ar^2$, $Ar^3$ and $Ar^4$ denote arylene or heteroarylene, preferably having electron donor properties, selected from the group consisting of the following formulae

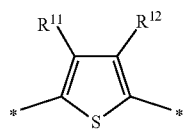
(D1)

(D2)

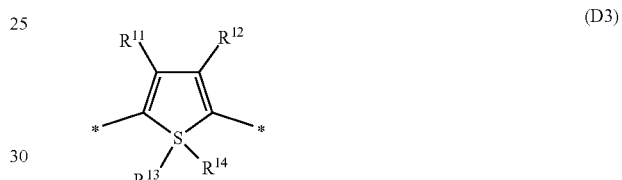
(D3)

(D4)

(D5)

(D6)

(D7)

(D8)

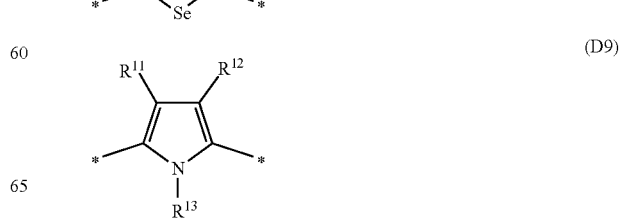
(D9)

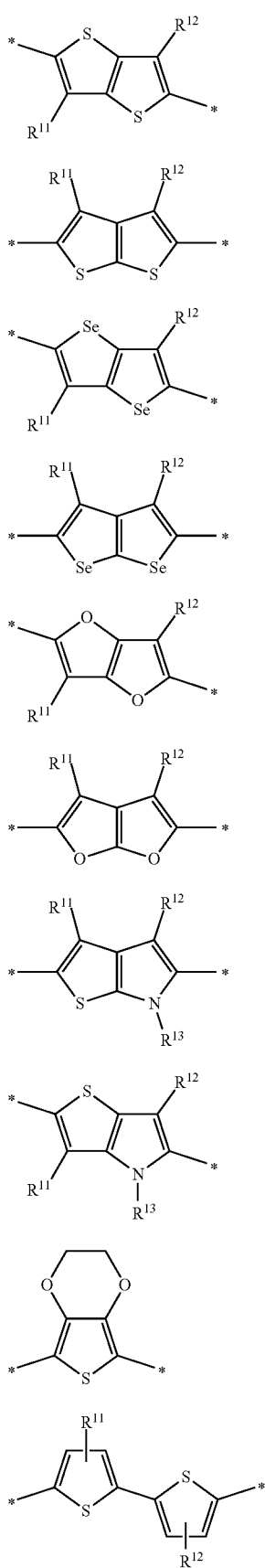
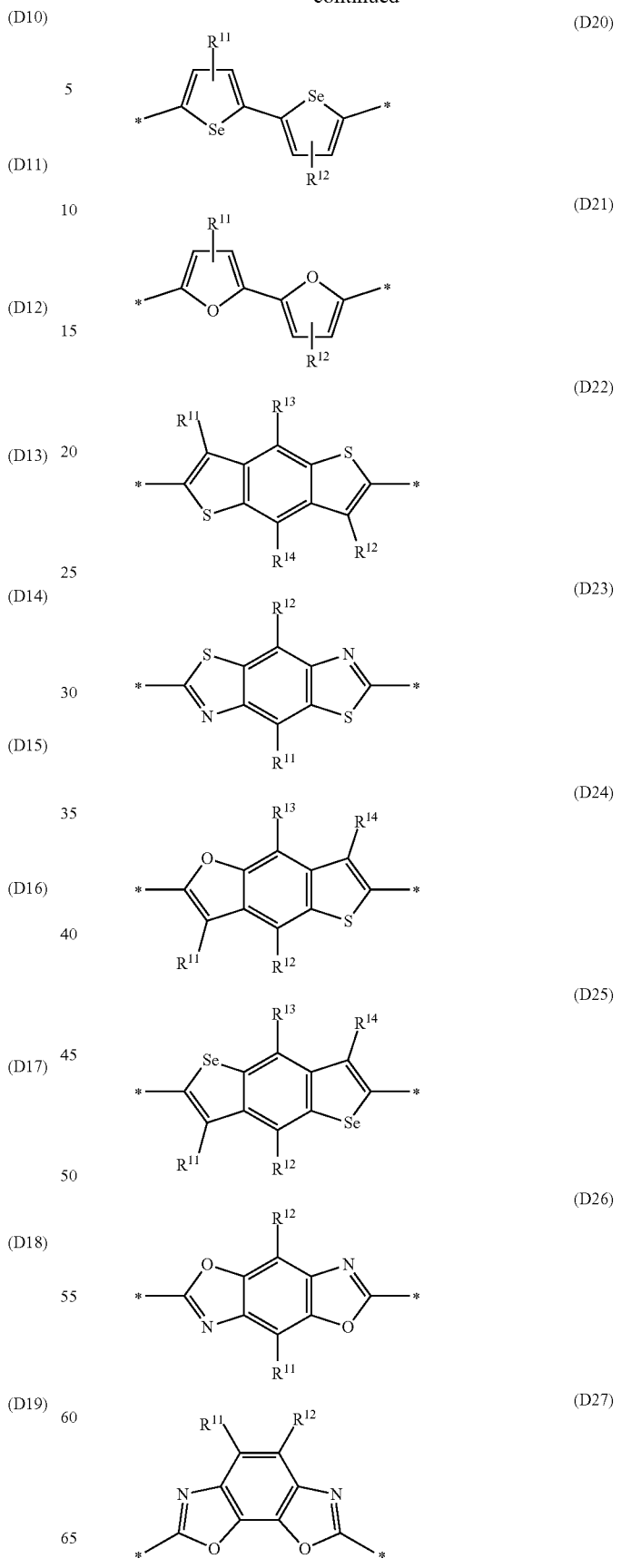

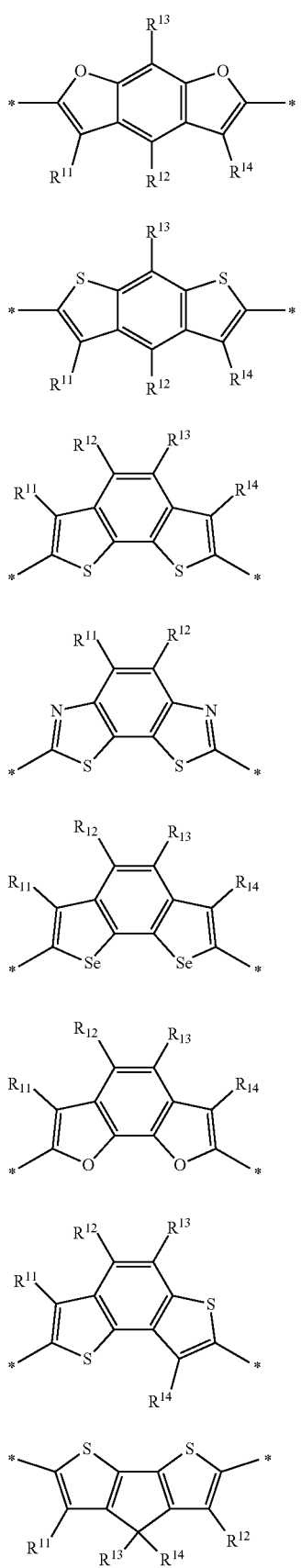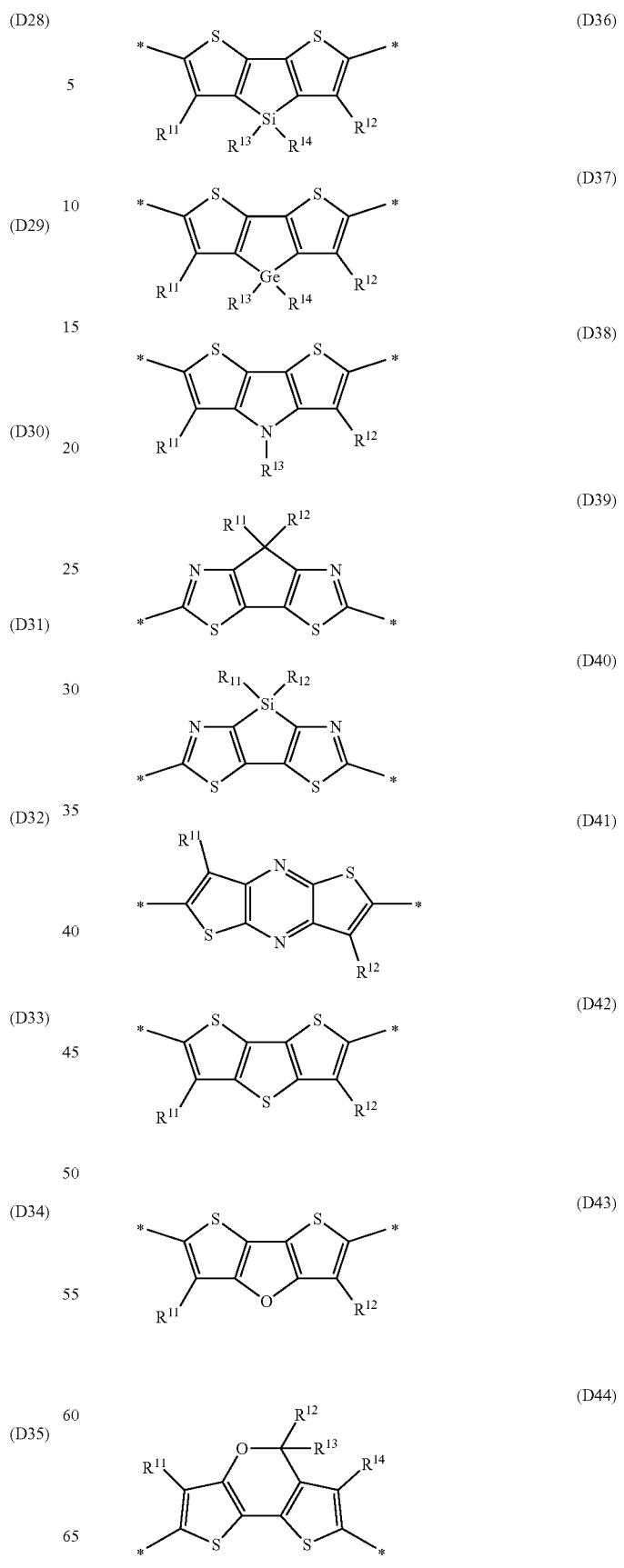

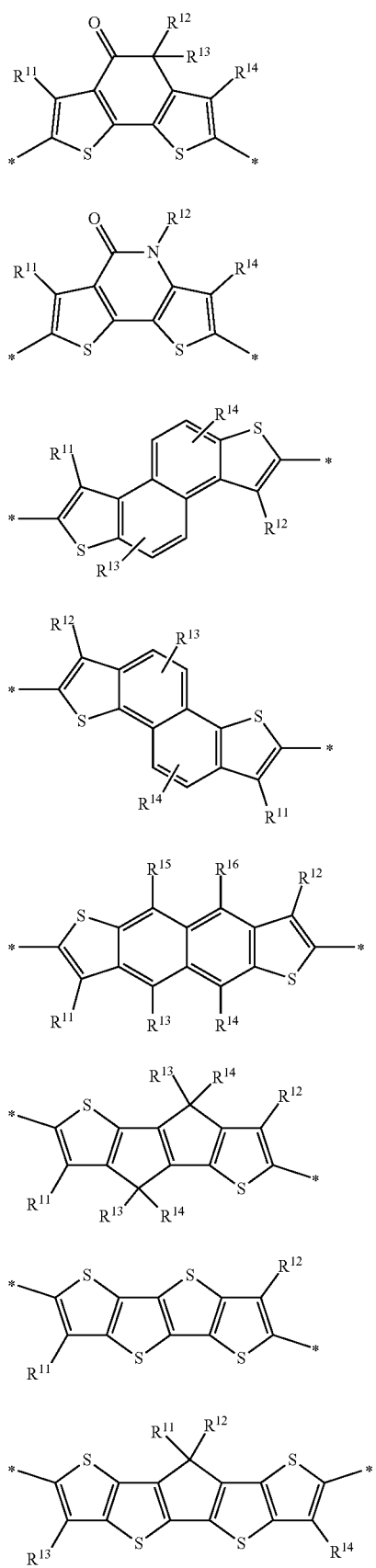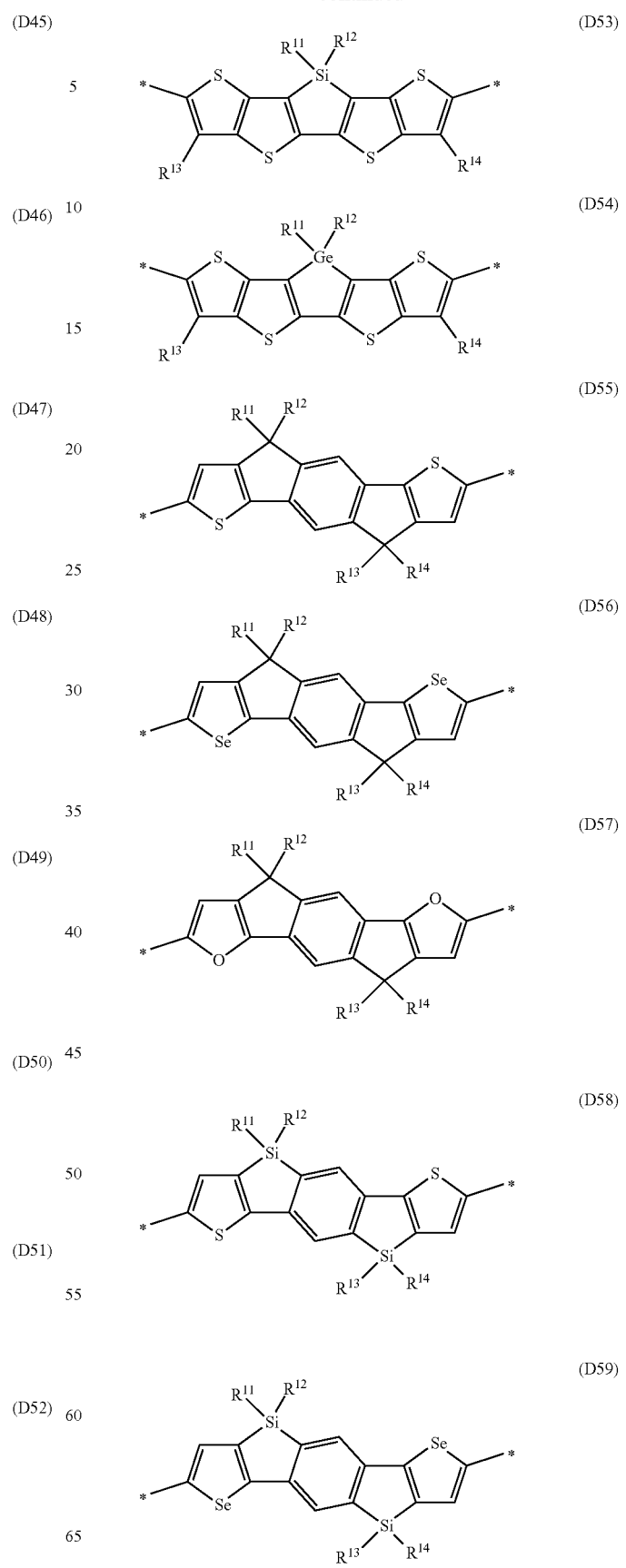

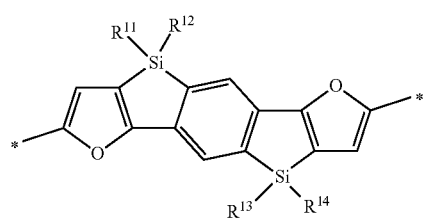
(D60)
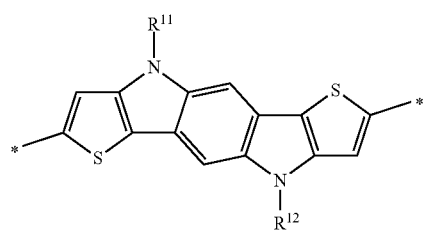
(D61)
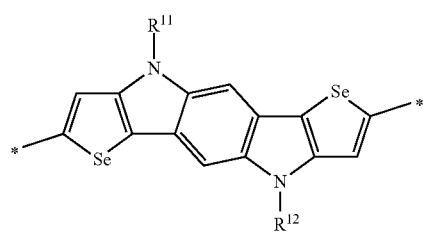
(D62)
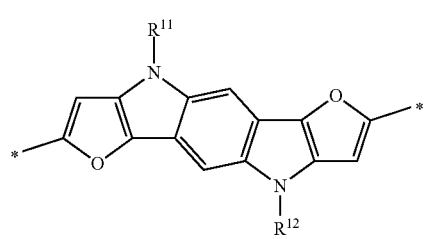
(D63)
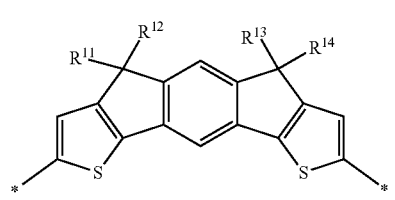
(D64)
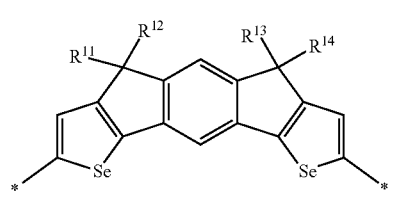
(D65)
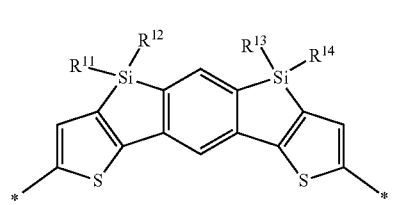
(D66)
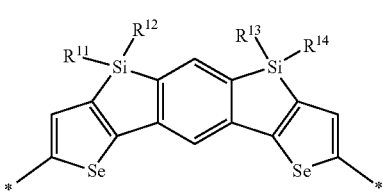
(D67)
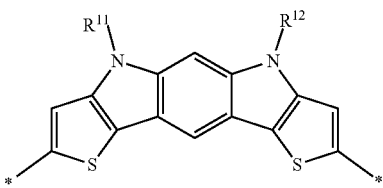
(D68)
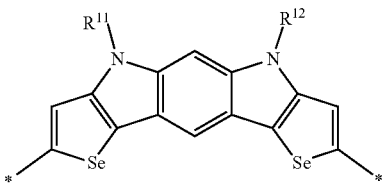
(D69)
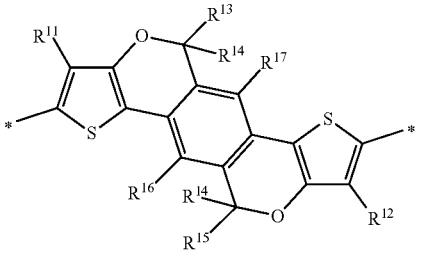
(D70)
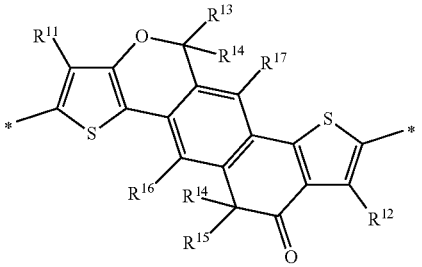
(D71)
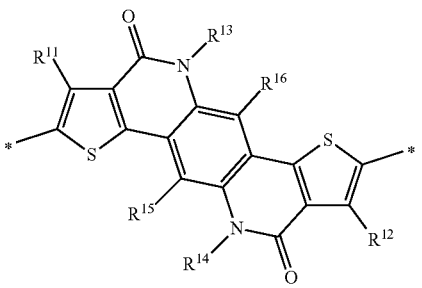
(D72)

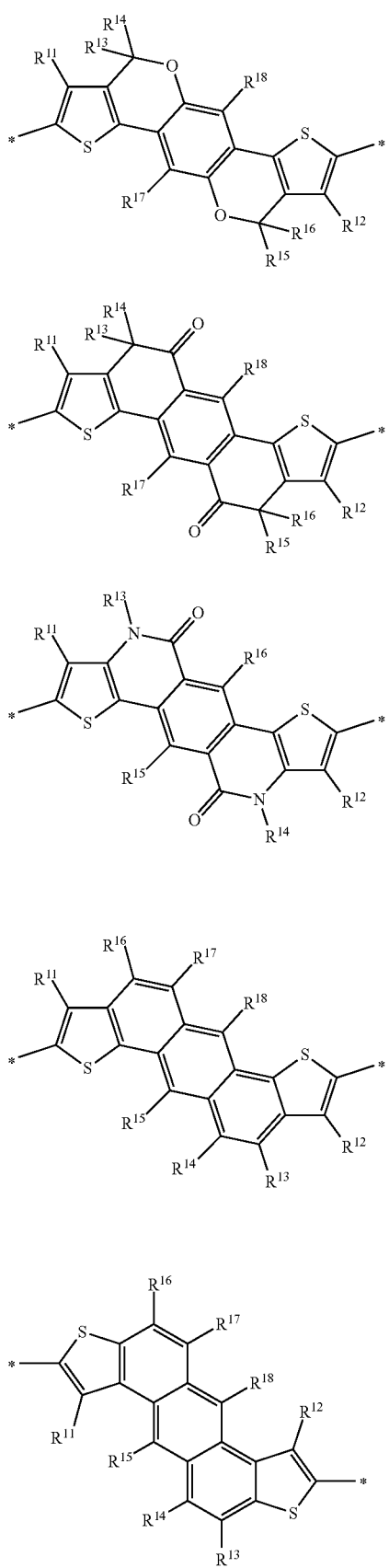
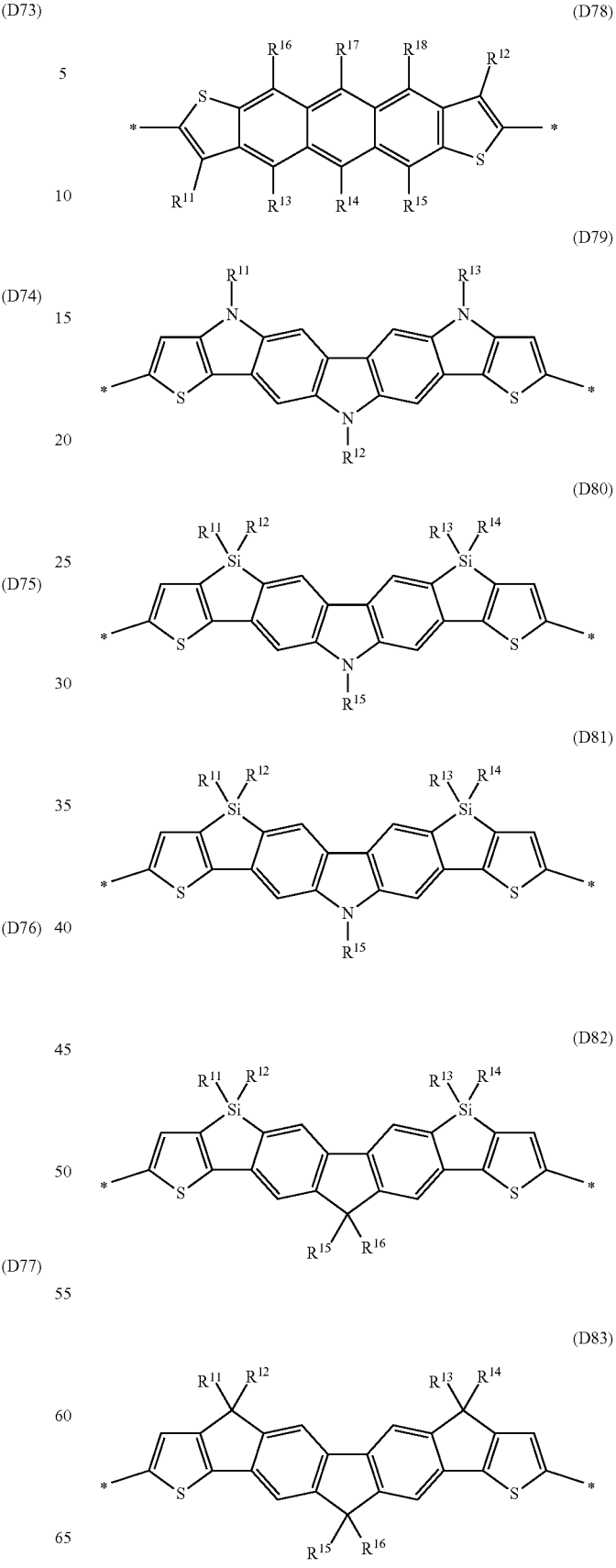

-continued
(D84)
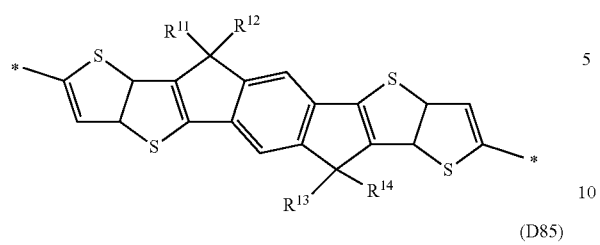
(D85)
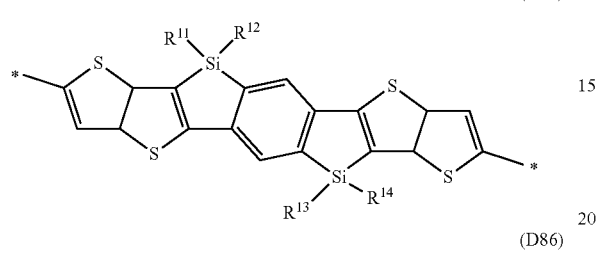
(D86)
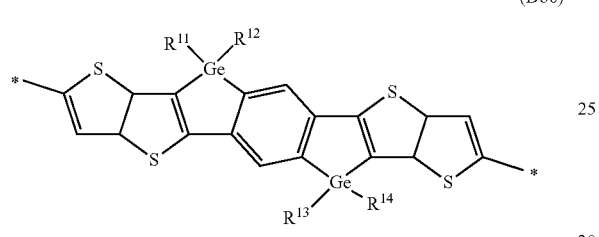
(D87)
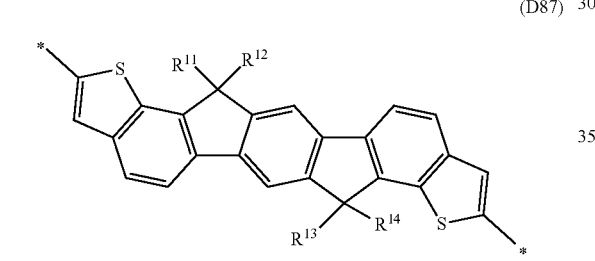
(D88)
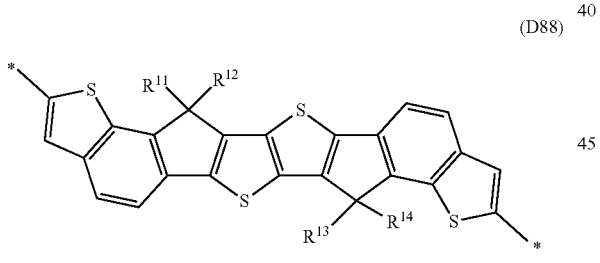
(D89)
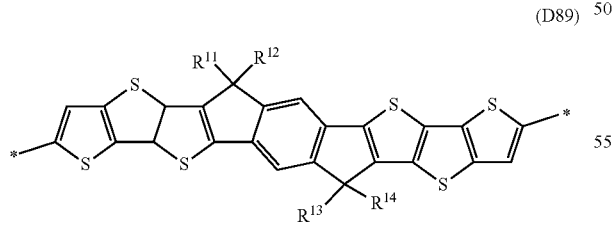
(D90)
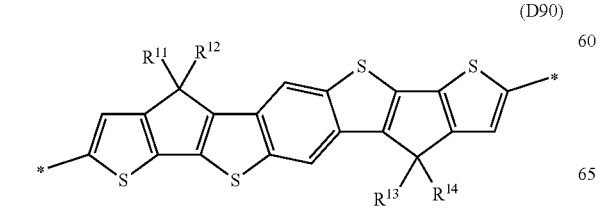
-continued
(D91)
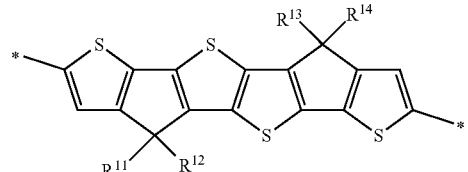
(D92)
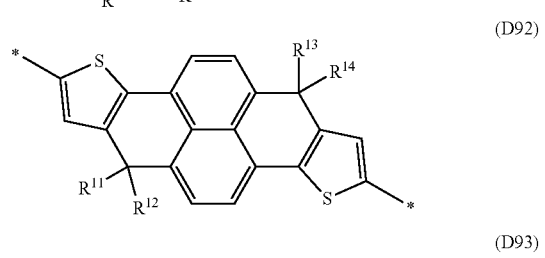
(D93)
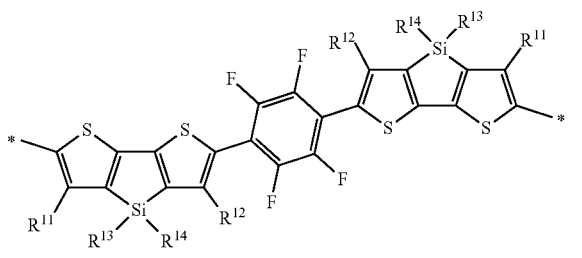
(D94)
(D95)
(D96)
(D97)
(D98)
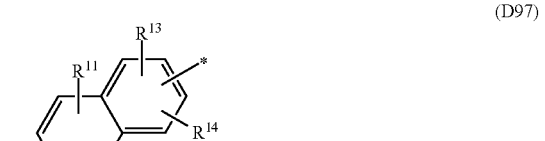
(D99)

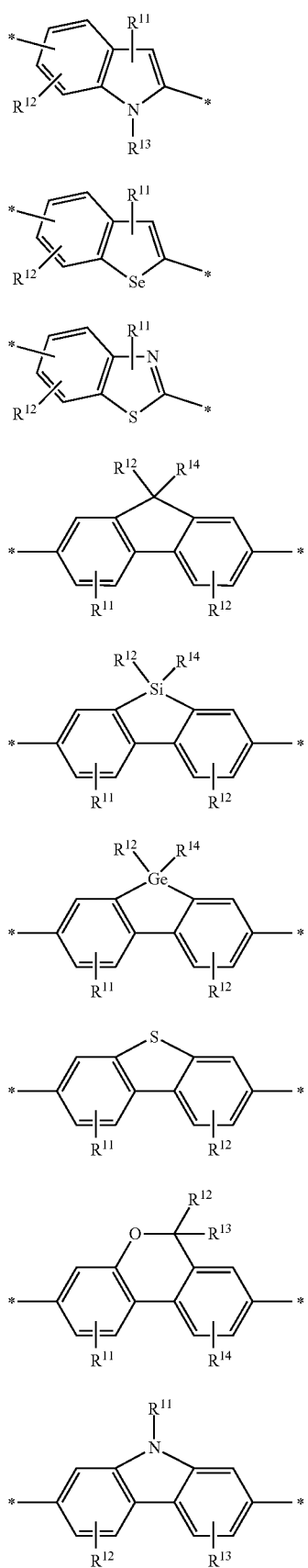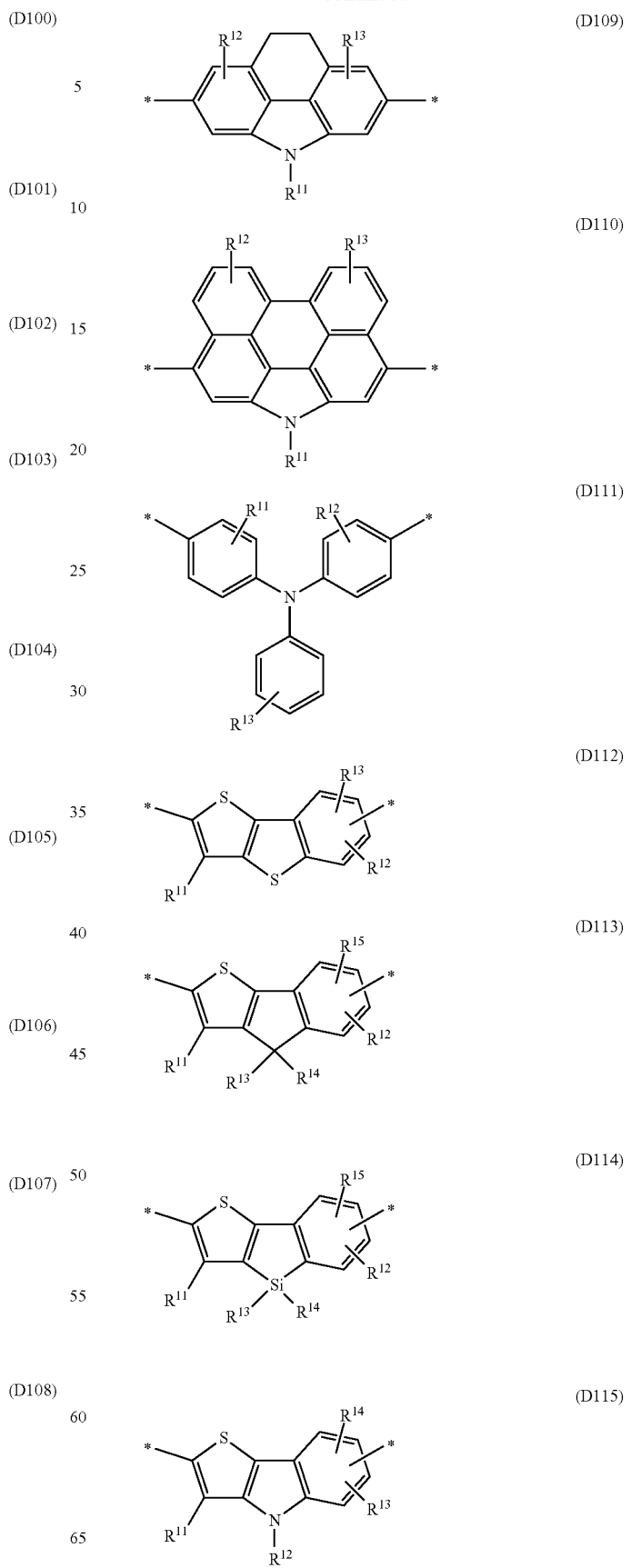

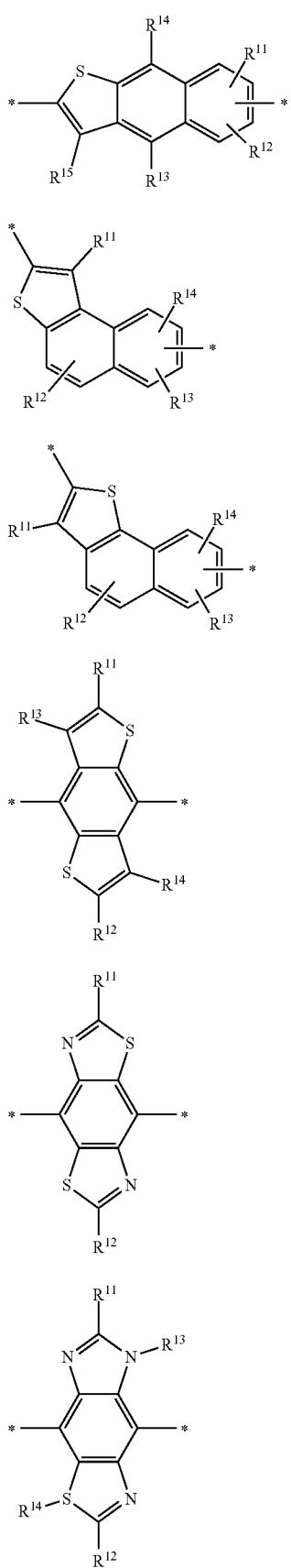
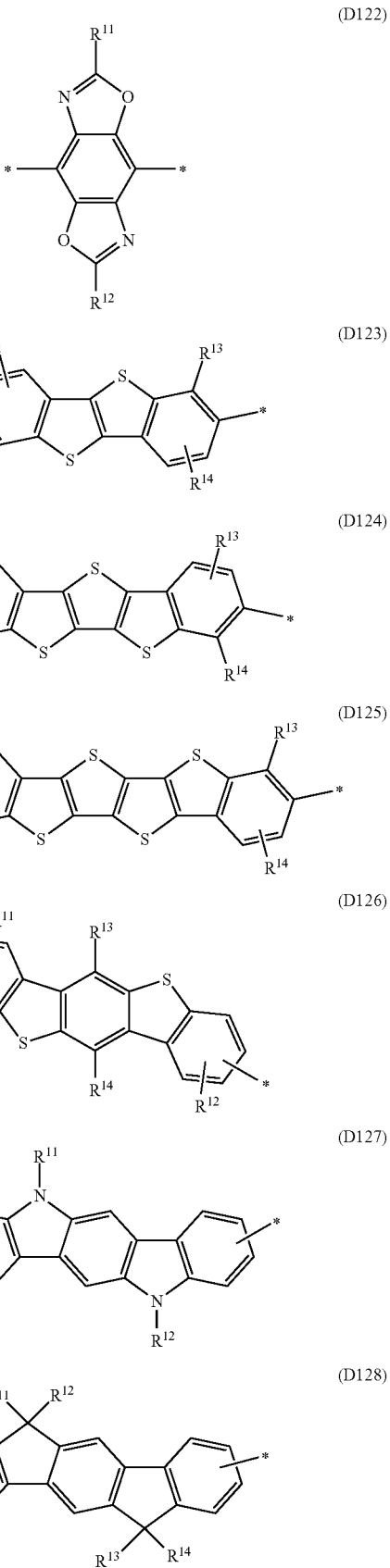

-continued
(D129) 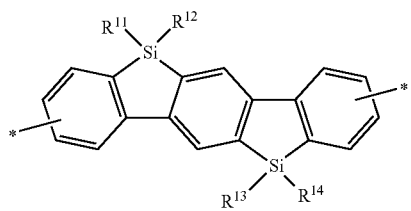
(D130) 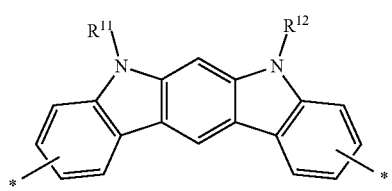
(D131) 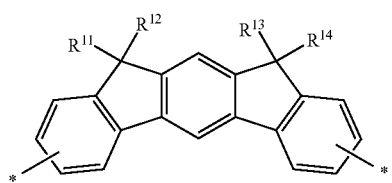
(D132) 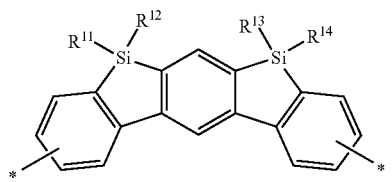
(D133) 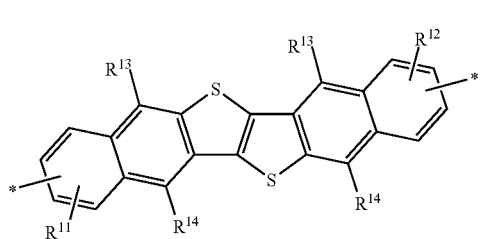
(D134) 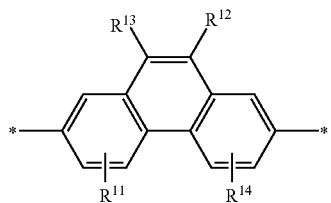
(D135) 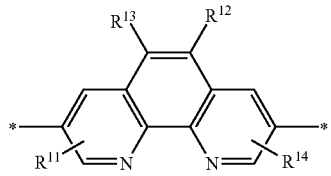
(D136) 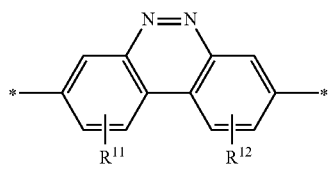
-continued
(D137) 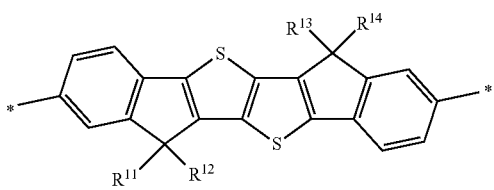
(D138) 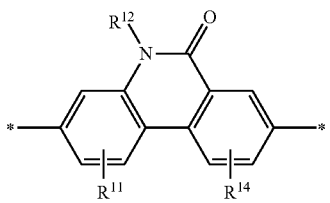
(D139) 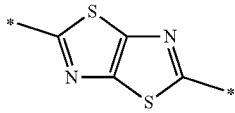
(D140) 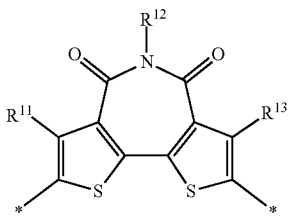
(D141) 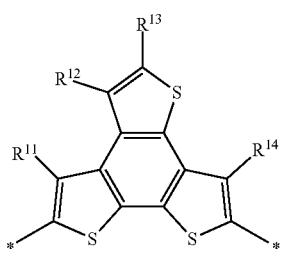
(D142) 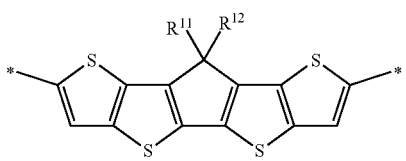
(D143) 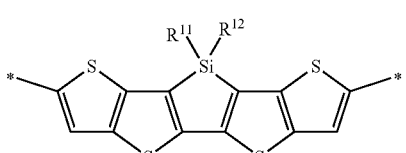
(D144) 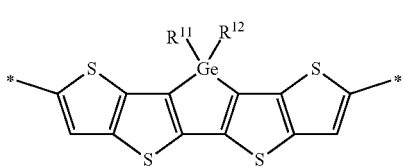

(D145) 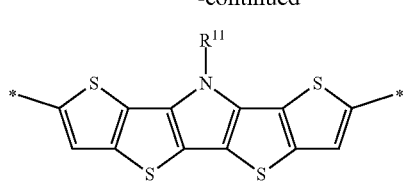

(D146) 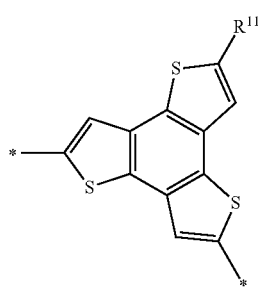

(D147) 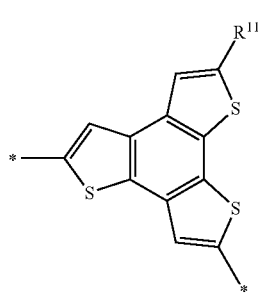

(D148) 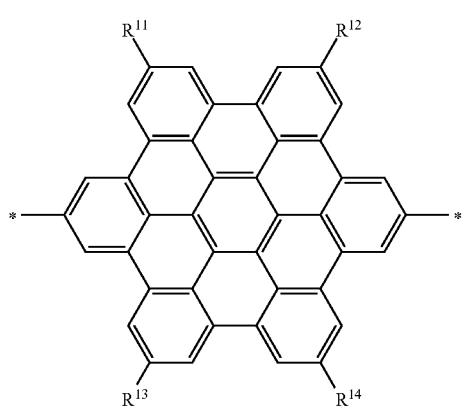

(D149) 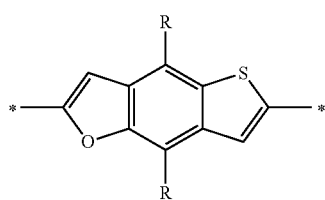

wherein $R^{11}$, $R^{12}$, $R^{13}$, $R^{14}$, $R^{15}$, $R^{16}$, $R^{17}$ and $R^{18}$ independently of each other denote H or have one of the meanings of L as defined above and below.

Preferred donor units are selected from formulae D1, D10, D19, D22, D30, D35, D36, D37, D38, D42, D44, D55, D84, D93, D94, D103, D108, D111, D137, D139, D140 or D141 wherein preferably at least one of $R^{11}$, $R^{12}$, $R^{13}$ and $R^{14}$ is different from H.

Further preferred are repeating units, monomers, oligomers, polymers and small molecules of formulae II1, II2, III, III1-III8, IV, V1, V2, V1a-V1d, V1 and V2 and their subformulae wherein one or more of $Ar^1$, $Ar^2$, $Ar^3$ and $Ar^4$ denote arylene or heteroarylene, preferably having electron acceptor properties, selected from the group consisting of the following formulae (A1) 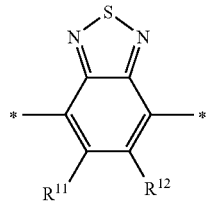

(A2) 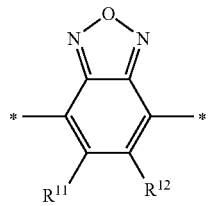

(A3) 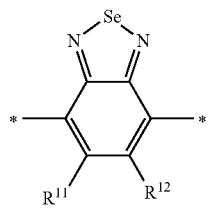

(A4) 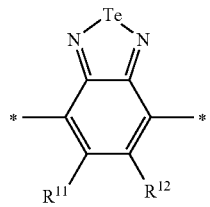

(A5) 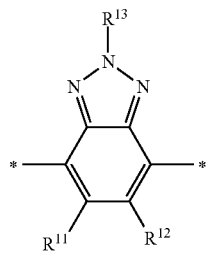

(A6) 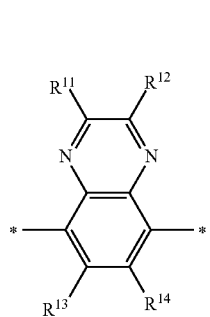

-continued
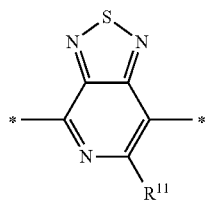  (A7)
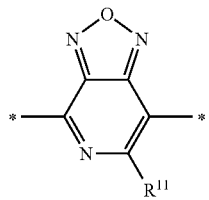  (A8)
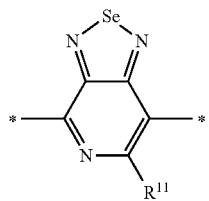  (A9)
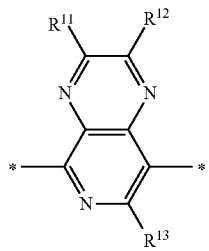  (A10)
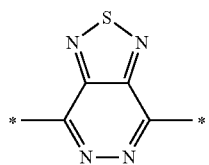  (A11)
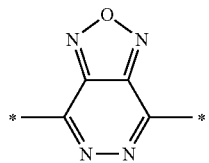  (A12)
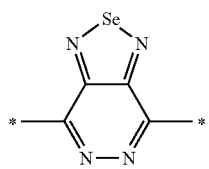  (A13)
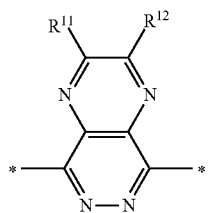  (A14)
-continued
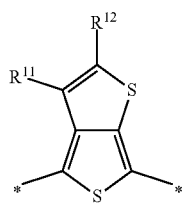  (A15)
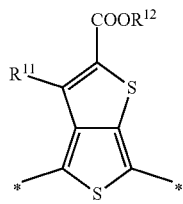  (A16)
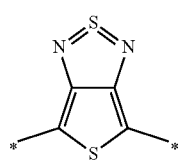  (A17)
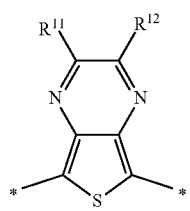  (A18)
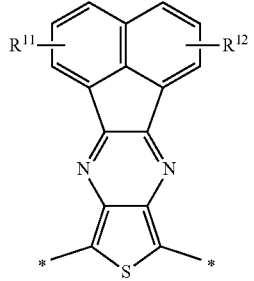  (A19)
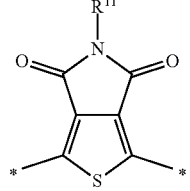  (A20)
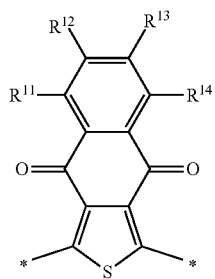  (A21)

-continued
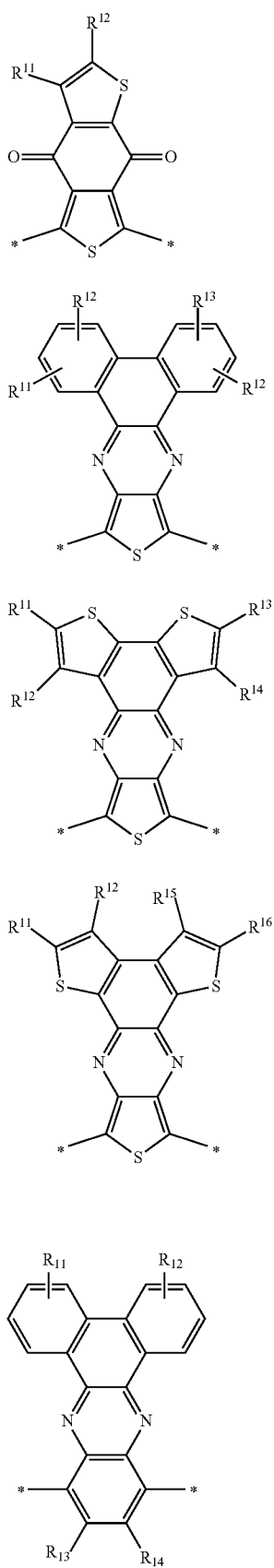
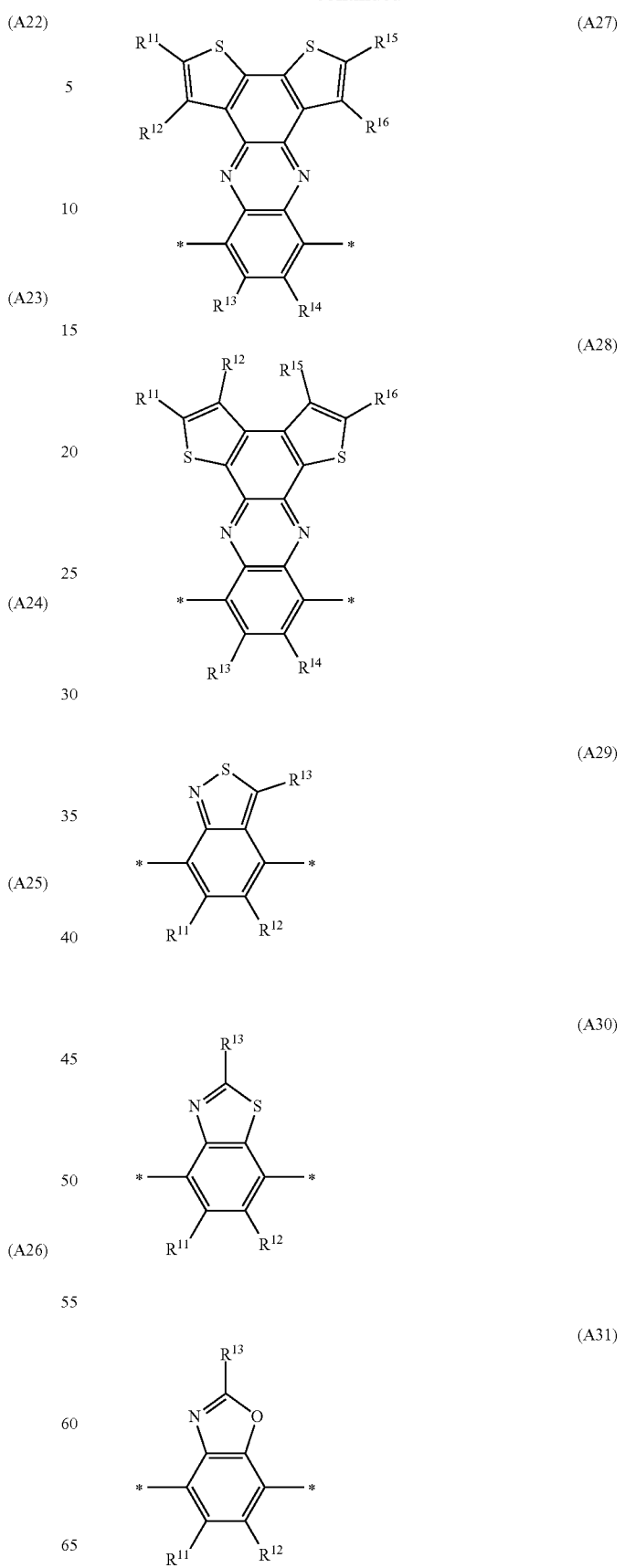

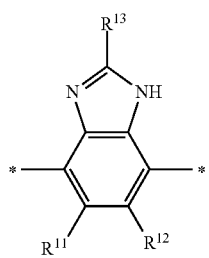
(A32)
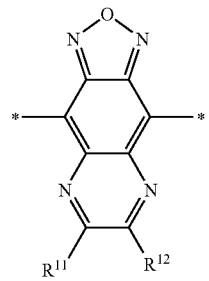
(A37)
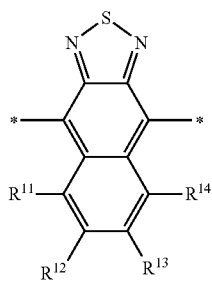
(A33)
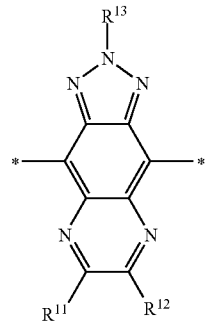
(A38)
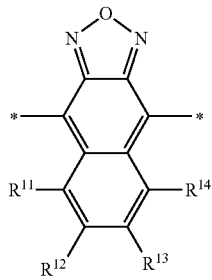
(A34)
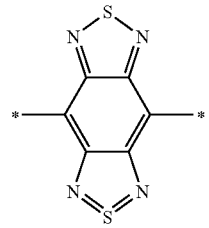
(A39)
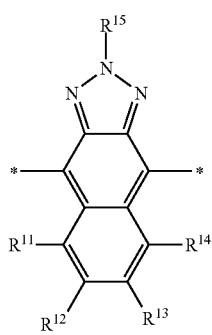
(A35)
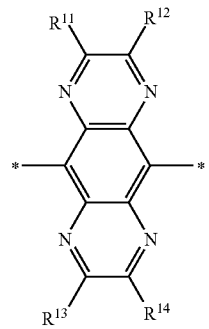
(A40)
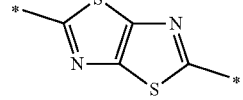
(A41)
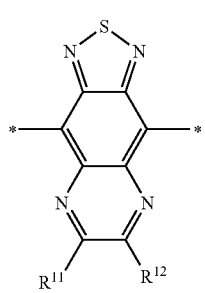
(A36)
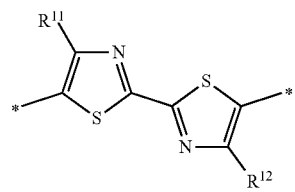
(A42)
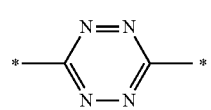
(A43)

-continued
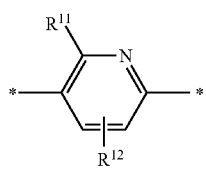
(A44)
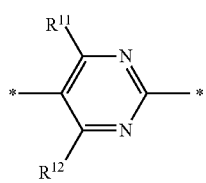
(A45)
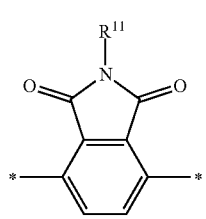
(A46)
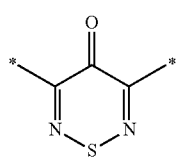
(A47)
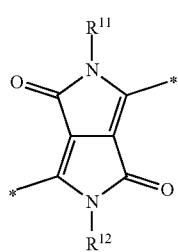
(A48)
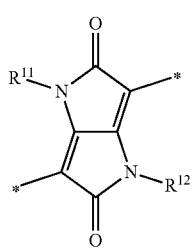
(A49)
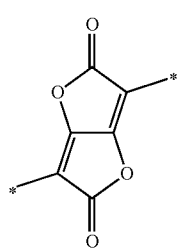
(A50)
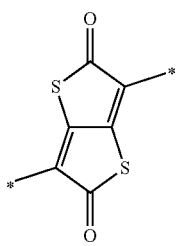
(A51)
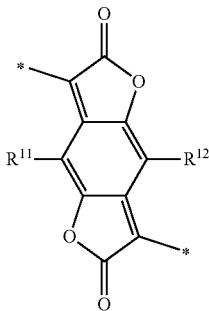
(A52)
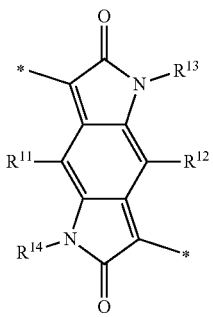
(A53)
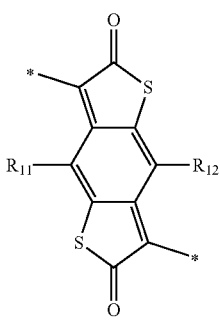
(A54)
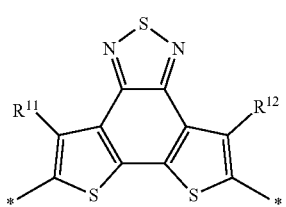
(A55)

-continued
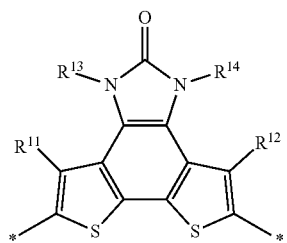 (A56)
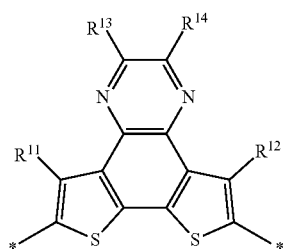 (A57)
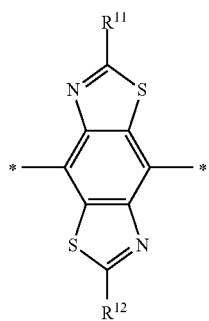 (A58)
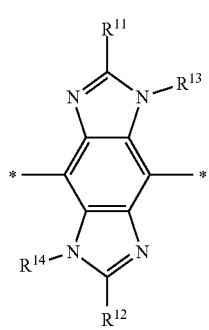 (A59)
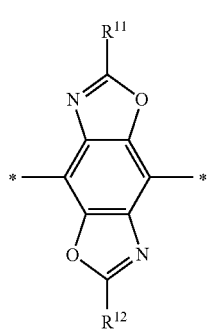 (A60)
-continued
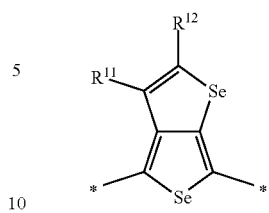 (A61)
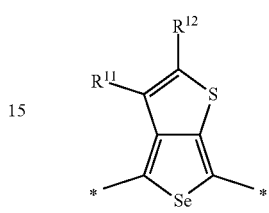 (A62)
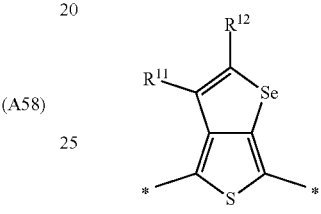 (A63)
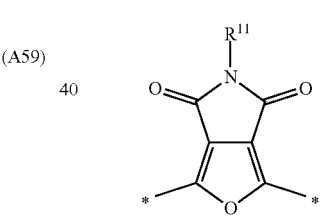 (A64)
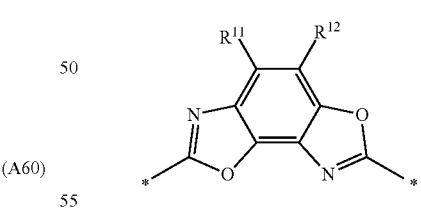 (A65)
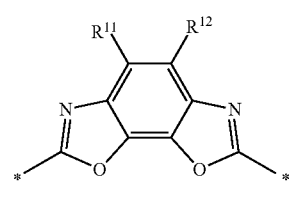 (A66)
(A67)

(A68) 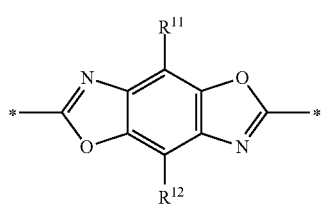
(A69) 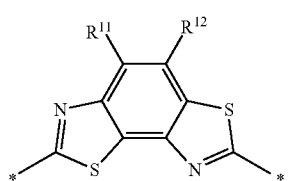
(A70) 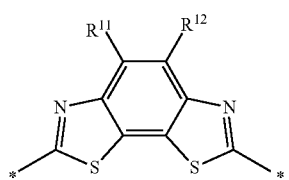
(A71) 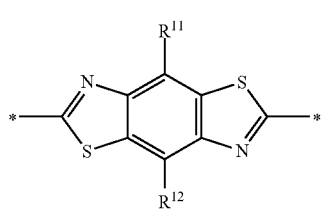
(A72) 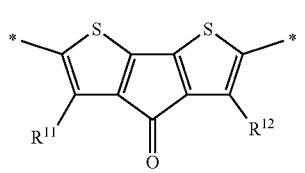
(A73) 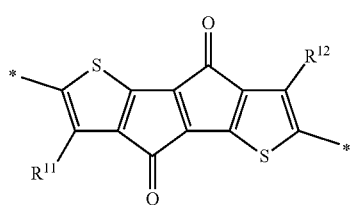
(A74) 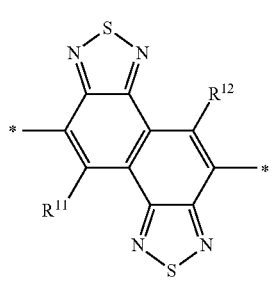
(A75) 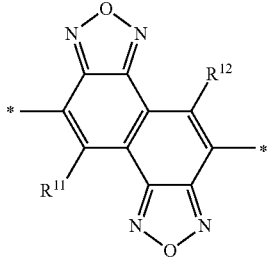
(A76) 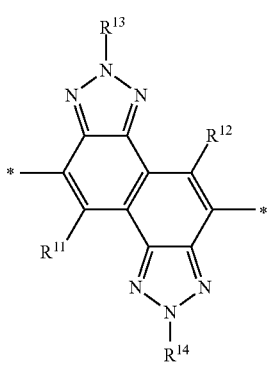
(A77) 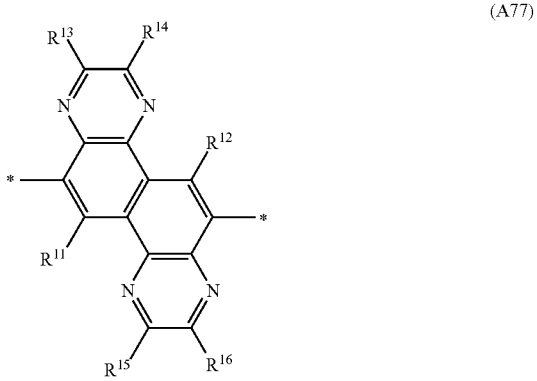
(A78) 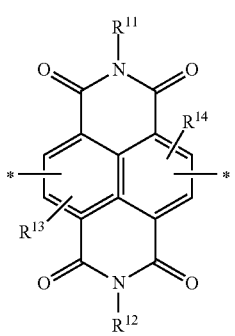

-continued
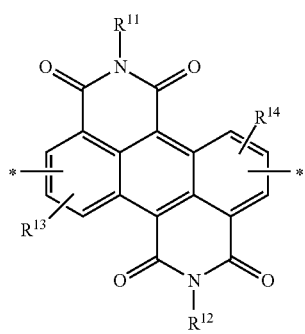 (A79)
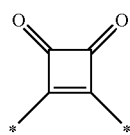 (A80)
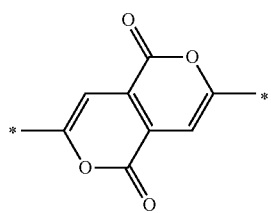 (A81)
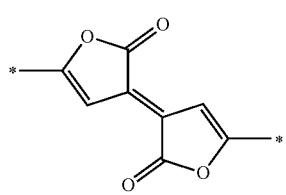 (A82)
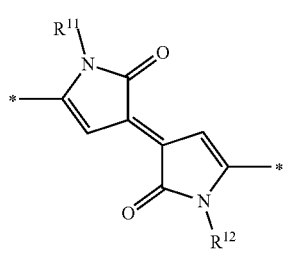 (A83)
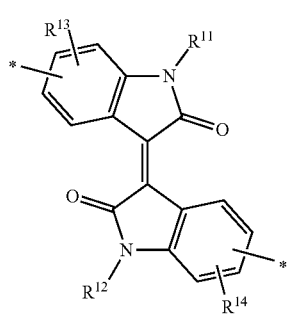 (A84)
-continued
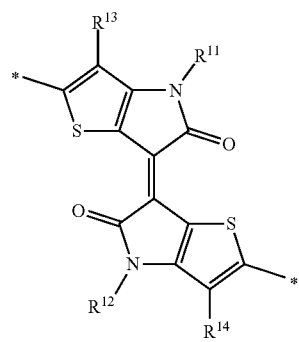 (A85)
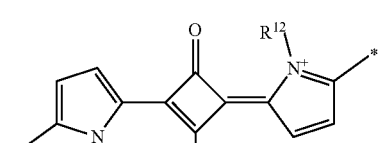 (A86)
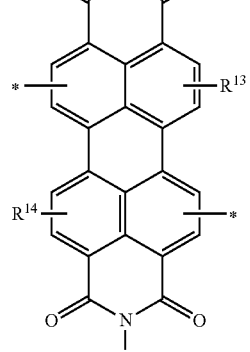 (A87)
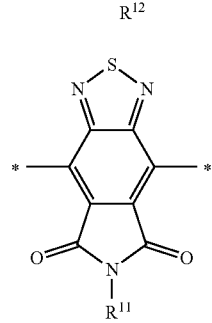 (A88)
 (A89)

(A90) 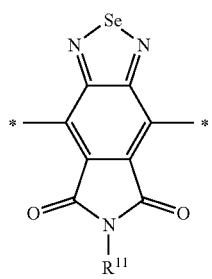

(A91) 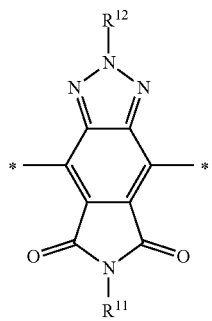

(A92) 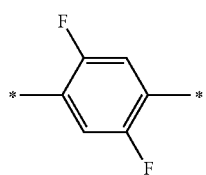

(A93) 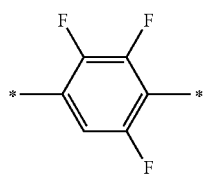

(A94) 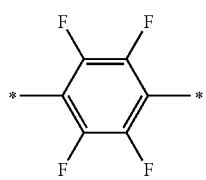

(A95) 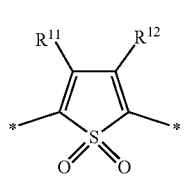

(A96) 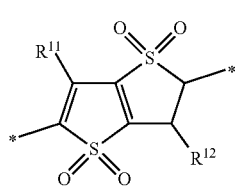

(A97) 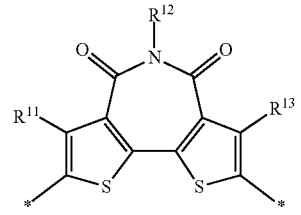

(A98) 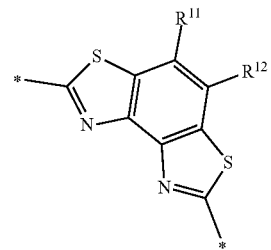

(A99) 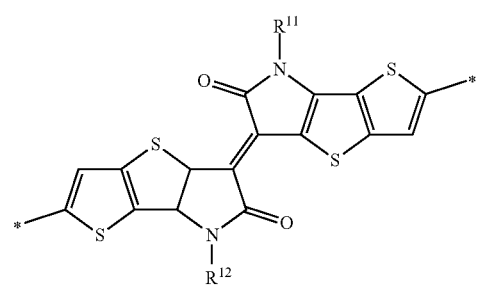

(A100) 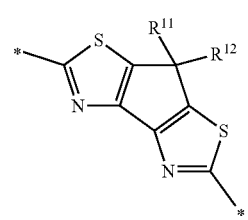

(A101) 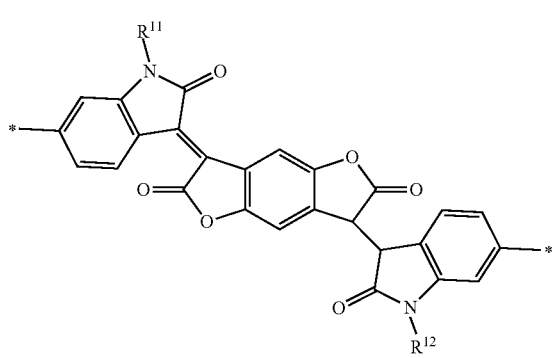

wherein $R^{11}$, $R^{12}$, $R^{13}$, $R^{14}$, $R^{15}$ and $R^{16}$ independently of each other denote H or have one of the meanings of L as defined above and below.

Preferred acceptor units are selected from formulae A1, A2, A3, A7, A15, A16, A20, A41, A48, A74, A84, A85, A88 or A94 wherein preferably at least one of $R^{11}$, $R^{12}$, $R^{13}$ and $R^{14}$ is different from H.

Further preferred are repeating units, monomers, oligomers, polymers and small molecules of formulae II1, II2, III, III1-III8, IV, V1, V2, V1a-V1d, V1 and V2 and their subformulae wherein one or more of $Ar^1$, $Ar^2$, $Ar^3$ and $Ar^4$ denote arylene or heteroarylene selected from the group consisting of the following formulae

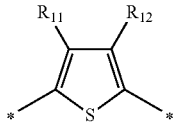
Sp1

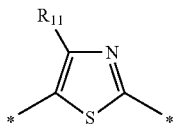
Sp2

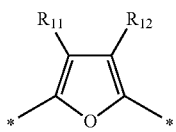
Sp3

Sp4

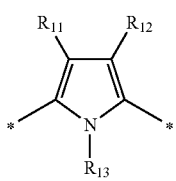
Sp5

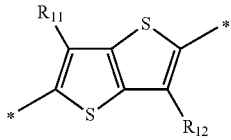
Sp6

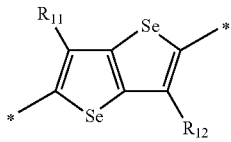
Sp7

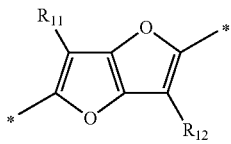
Sp8

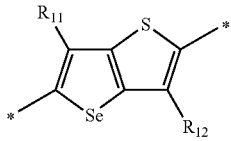
Sp9

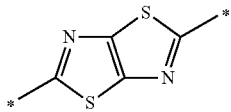
Sp10

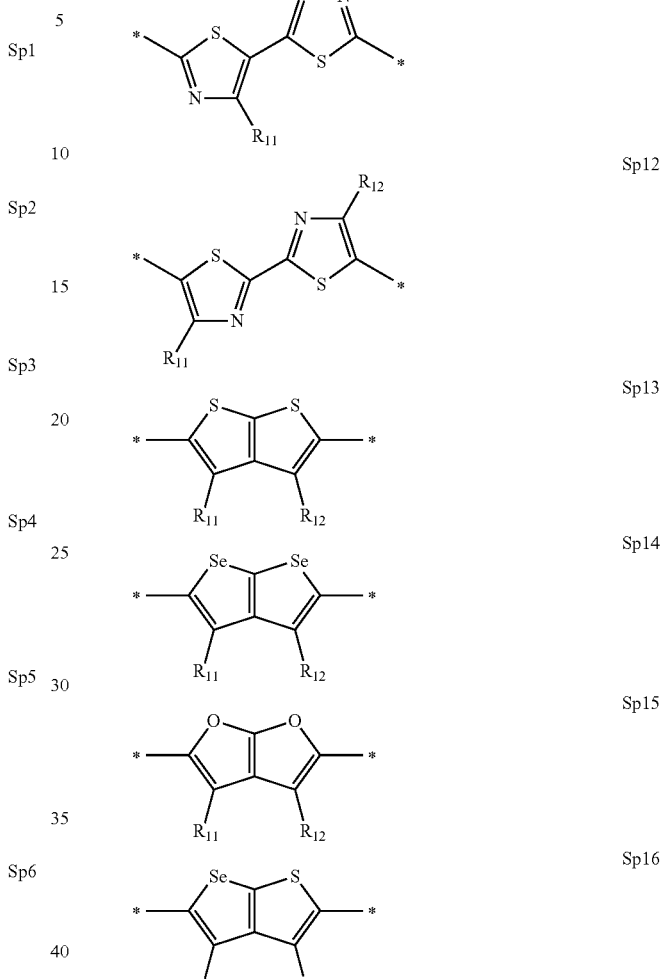

wherein $R^{11}$ and $R^{12}$ independently of each other denote H or have one of the meanings of L as defined above and below.

Very preferred are units selected from formulae Sp1, Sp4, Sp6, wherein preferably one of $R^{11}$ and $R^{12}$ is H or both $R^{11}$ and $R^{12}$ are H.

Further preferred are repeating units, monomers and polymers of formulae II1, II2, III, III1-III8, IV, V1, V2, V1a-V1 d and their subformulae wherein a) one or more of $Ar^1$, $Ar^2$, $Ar^3$ and $Ar^4$ denote arylene or heteroarylene, preferably having electron donor properties, selected from the group consisting of the formulae D1-D145, very preferably of the formulae D1, D10, D19, D22, D30, D35, D36, D37, D38, D42, D44, D55, D84, D93, D94, D103, D108, D111, D137, D139, D140 and D141, and b) one or more of $Ar^1$, $Ar^2$, $Ar^3$ and $Ar^4$ denote arylene or heteroarylene selected from the group consisting of formulae Sp1-Sp15, very preferably of formulae Sp1, Sp6 and Sp10.

Further preferred are repeating units, monomers and polymers of formulae II1, II2, III, III1-III8, IV, V1, V2, V1a-V1 d and their subformulae wherein all of $Ar^1$, $Ar^2$, $Ar^3$ and $Ar^4$ are selected from groups a) and b) above, preferably containing at least one group $Ar^1$, $Ar^2$, $Ar^3$ and $Ar^4$ selected from group a) and at least one group $Ar^1$, $Ar^2$, $Ar^3$ and $Ar^4$ selected from group b).

Further preferred are oligomers and small molecules of formula VI1 and VI2 wherein $Ar^{1-10}$ are selected from the following groups
a) the group consisting of the formulae D1-D145, very preferably of the formulae D1, D10, D19, D22, D30, D35, D36, D37, D38, D42, D44, D55, D84, D93, D94, D103, D108, D111, D137, D139, D140 and D141,
b) the group consisting of the formulae A1-A97, very preferably of the formulae A1, A2, A3, A7, A15, A16, A20, A41, A48, A74, A84, A85, A88 and A94,
c) the group consisting of the formulae Sp1-Sp15, very preferably of the formulae Sp1, Sp6 and Sp10.

The polymers according to the present invention can be prepared for example by copolymerising one or more monomers of formula V1, V2 or V1a-V1d with each other or with one or monomers of the following formulae in an aryl-aryl coupling reaction $R^7$—$Ar^1$—$R^8$  MI $R^7$—$Ar^2$—$R^8$  MII $R^7$—$Ar^3$—$R^8$  MIII $R^7$—$Ar^4$—$R^8$  MIV wherein $Ar^{1-4}$, $R^7$ and $R^8$ have the meanings given in formula II2 and V1 or one of the preferred meanings given above and below.

The polymer according to the present invention can be synthesized according to or in analogy to methods that are known to the skilled person and are described in the literature. Other methods of preparation can be taken from the examples.

For example, the polymer can be suitably prepared by aryl-aryl coupling reactions, such as Yamamoto coupling, C—H activation coupling, Suzuki coupling, Stille coupling, Sonogashira coupling, Heck coupling or Buchwald coupling. Suzuki coupling, Stille coupling and Yamamoto coupling are especially preferred. The monomers which are polymerised to form the repeat units of the polymers can be prepared according to methods which are known to the person skilled in the art.

Preferably the polymer is prepared from monomers selected from formulae V1, V2, V1a-d and MI-MIV as described above.

Another aspect of the invention is a process for preparing a polymer by coupling one or more identical or different monomers selected from formulae V1, V2, V1a-d with each other and/or with one or more co-monomers, preferably selected from formulae MI-MIV, in a polymerisation reaction, preferably in an aryl-aryl coupling reaction.

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in J. Chem. Soc., Chem. Commun., 1977, 683-684. Yamamoto coupling is described in for example in T. Yamamoto et al., Prog. Polym. Sci., 1993, 17, 1153-1205, or WO 2004/022626 A1. Stille coupling is described for example in Z. Bao et al., J. Am. Chem. Soc., 1995, 117, 12426-12435. C—H activation is described for example for example in M. Leclerc et al, Angew. Chem. Int. Ed. 2012, 51, 2068-2071. For example, when using Yamamoto coupling, monomers having two reactive halide groups are preferably used. When using Suzuki coupling, monomers having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used. When synthesizing a linear polymer by C—H activation polymerisation, preferably a monomer as described above is used wherein at least one reactive group is an activated hydrogen bond.

Preferred catalysts, especially for Suzuki, Negishi or Stille coupling, are selected from Pd(0) complexes or Pd(II) salts. Preferred Pd(0) complexes are those bearing at least one phosphine ligand such as $Pd(Ph_3P)_4$. Another preferred phosphine ligand is tris(ortho-tolyl)phosphine, i.e. $Pd(o-Tol_3P)_4$. Preferred Pd(II) salts include palladium acetate, i.e. $Pd(OAc)_2$ or trans-di(p-acetato)-bis[o-(di-o-tolylphosphino)benzyl]dipalladium(II). Alternatively the Pd(0) complex can be prepared by mixing a Pd(0) dibenzylideneacetone complex, for example tris(dibenzyl-idene acetone)dipalladium (0), bis(dibenzylideneacetone)palladium(0), or Pd(II) salts e.g. palladium acetate, with a phosphine ligand, for example triphenylphosphine, tris(ortho-tolyl)phosphine, tris(o-methoxyphenyl)phosphine or tri(tert-butyl)phosphine. Suzuki polymerisation is performed in the presence of a base, for example sodium carbonate, potassium carbonate, cesium carbonated, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

Suzuki, Stille or C—H activation coupling polymerisation may be used to prepare homopolymers as well as statistical, alternating and block random copolymers. Statistical, random block copolymers or block copolymers can be prepared for example from the above monomers, wherein one of the reactive groups is halogen and the other reactive group is a C—H activated bond, boronic acid, boronic acid derivative group or and alkylstannane. The synthesis of statistical, alternating and block copolymers is described in detail for example in WO 03/048225 A2 or WO 2005/014688 A2.

As alternatives to halogen as described above, leaving groups of formula —O—$SO_2Z^1$ can be used wherein $Z^1$ is as defined above. Particular examples of such leaving groups are tosylate, mesylate and triflate.

Preferred polymerisation conditions lead to alternating polymers which are particularly preferred for OTFT application, whereas statistical block co-polymers are prepared preferably for OPV and OPD application. Preferred polycondensation are Suzuki coupling, Stille coupling, Sonogashira coupling, Heck coupling or Buchwald coupling, Negishi coupling or C—H activation coupling where the first set of reactive groups is composed of —Cl, —Br, —I, O-tosylate, O-triflate, O-mesylate and O-nonaflate and the second set of reactive groups is composed of —H, —$SiR_2F$, —$SiRF_2$, —$B(OR)_2$, —CR=CHR', —C≡CH, —ZnX, —MgX and —$Sn(R)_3$. If a Yamamoto coupling reaction is used to prepare the polymer, the reactive monomer ends are both composed independently of —Cl, —Br, —I, O-tosylate, O-triflate, O-mesylate and O-nonaflate.

Suitable and preferred methods for preparing compounds according to the present invention are illustrated in the reaction schemes below.

Schemes 1-5 show the synthesis of the units of formula I1 and I2. Therein R and R' have one of the meanings of $R^1$ or $R^3$ given in formula I1.

As shown in J. Med. Chem., 2014, 57 (11), 4889-4905, the unsymmetrical 1-6-disubstituted-1H-[1,5]naphthyridin-2-one core can be accessed from the known intermediate, 6-methoxy-1H-[1,5]naphthyridin-2-one as exemplarily illustrated in Scheme 1.

Scheme 1

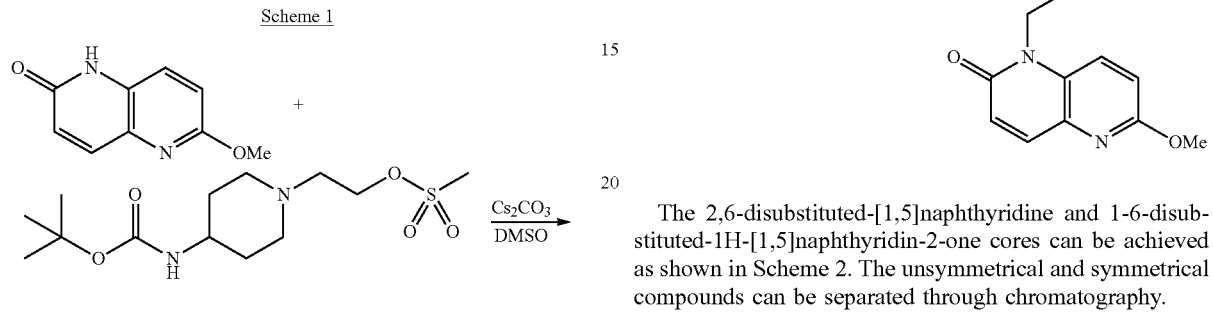

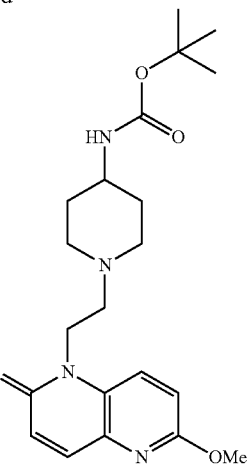

The 2,6-disubstituted-[1,5]naphthyridine and 1-6-disubstituted-1H-[1,5]naphthyridin-2-one cores can be achieved as shown in Scheme 2. The unsymmetrical and symmetrical compounds can be separated through chromatography.

Scheme 2

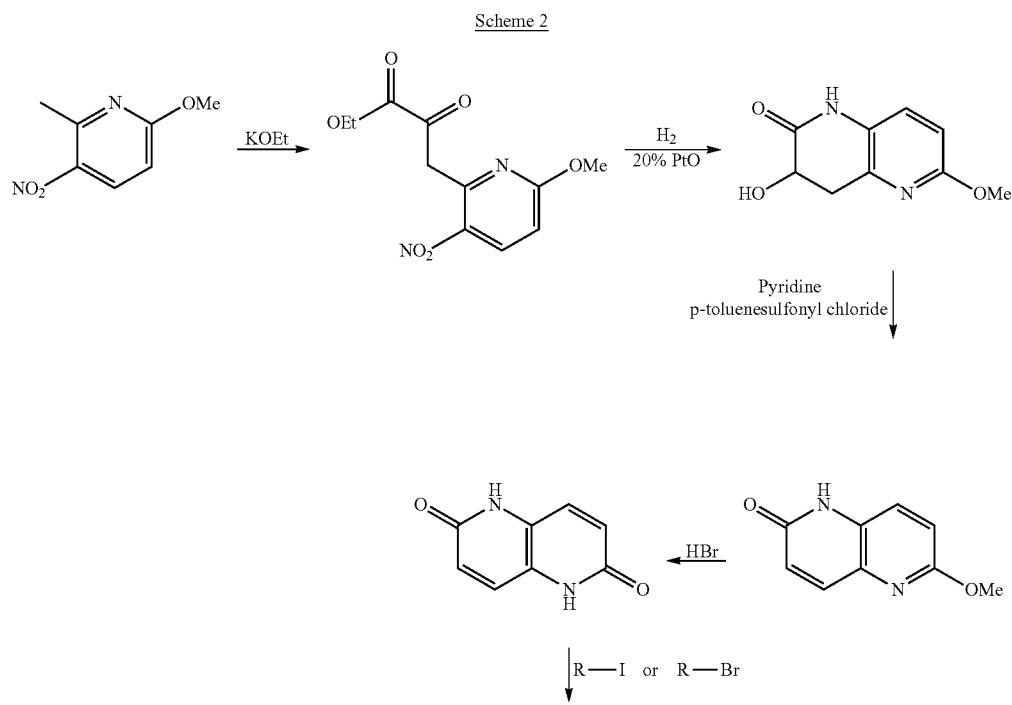

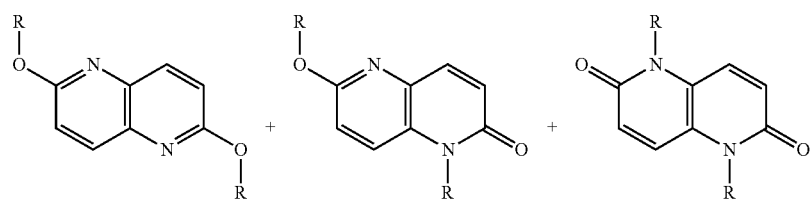

Different substituents R can be accessed as shown in Scheme 3.
Scheme 3
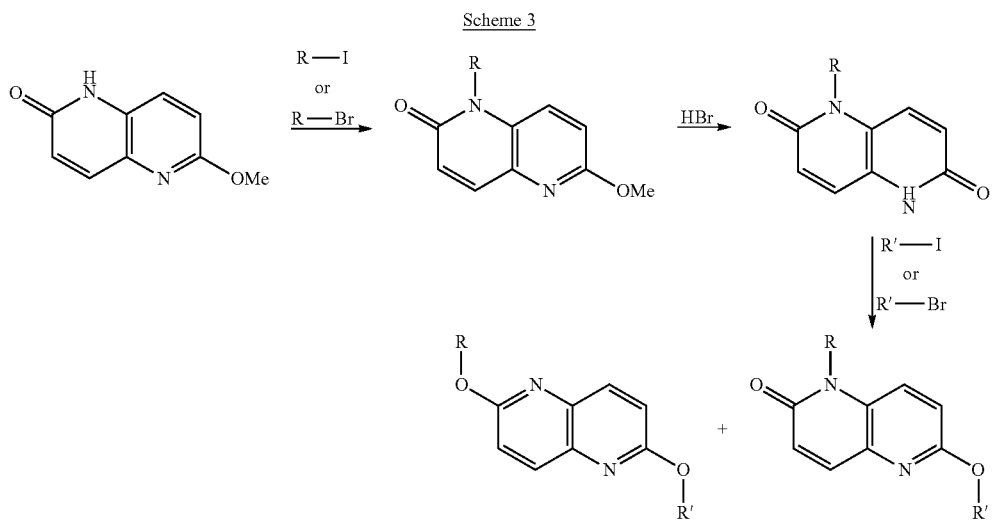
Alternative routes to the target compounds are shown in Schemes 4 and 5.
Scheme 4
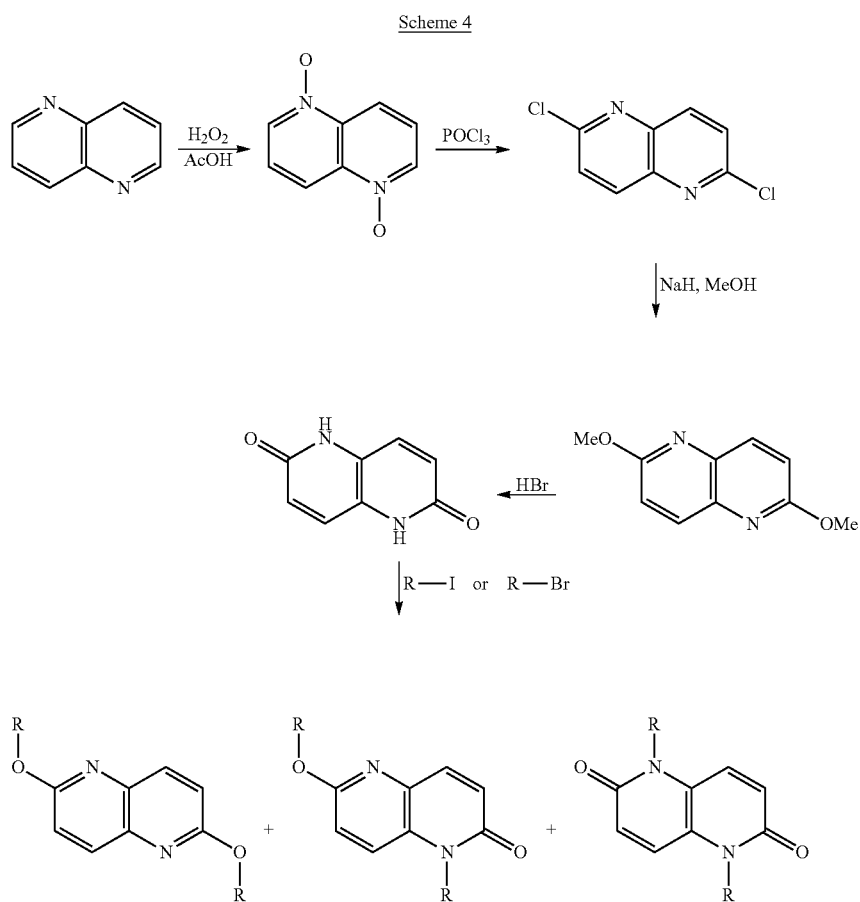

Scheme 5

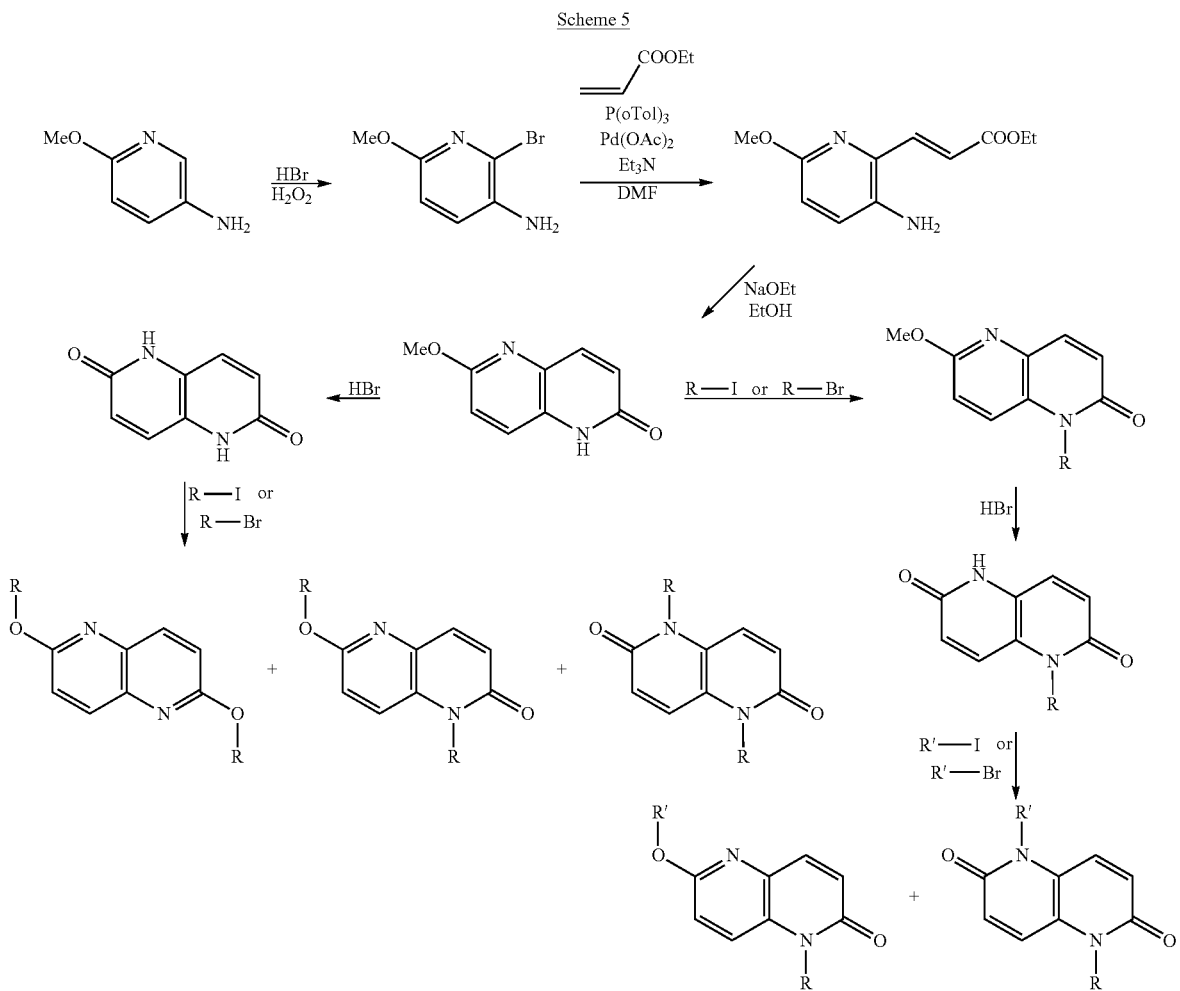

Following the generic 2,6-disubstituted-[1,5]naphthyridine and 1-6-disubstituted-1H-[1,5]naphthyridin-2-one core syntheses, functionalisation of the cores with reactive bromo, stannyl or boronate groups can be achieved as described in Schemes 6 and 7. Therein $X^{1,2}$ are Br, $SnR_3$ or $B(OR)_2$; R, R', $R^{1,2}$ are for example alkyl groups; $Ar^1$ is arylene or heteroarylene as defined for example in formula II1.

Scheme 6

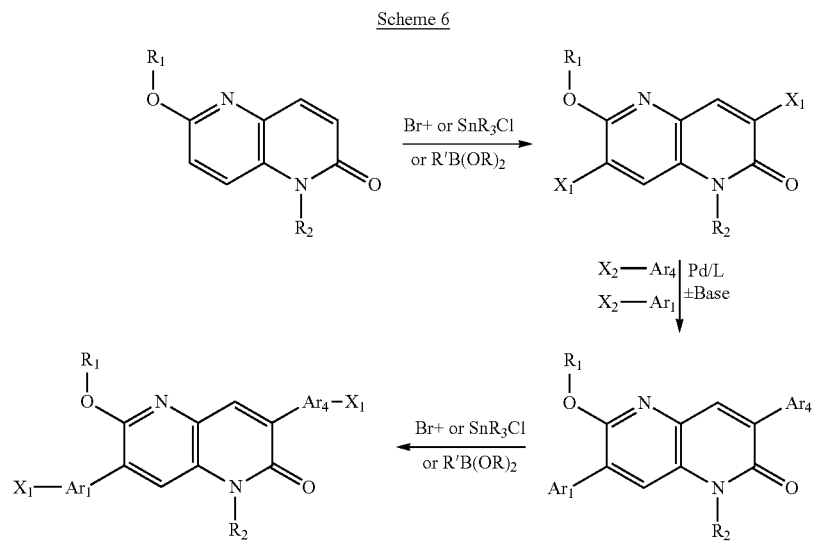

-continued
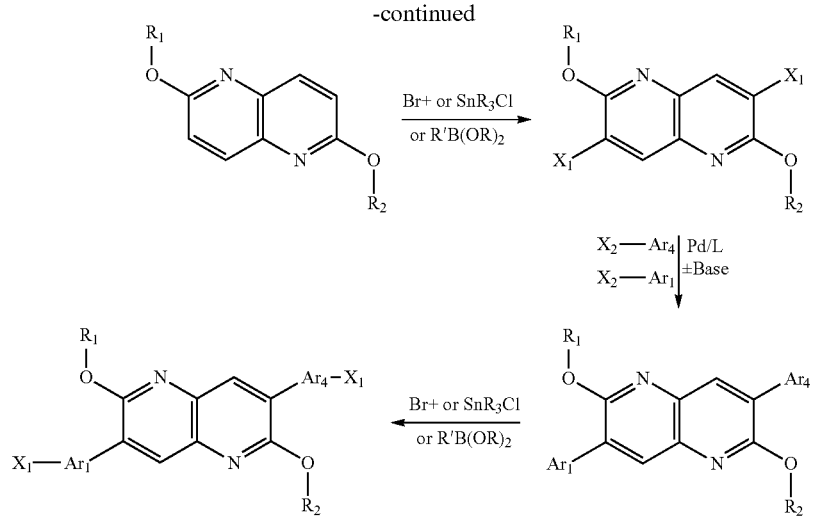
Scheme 7
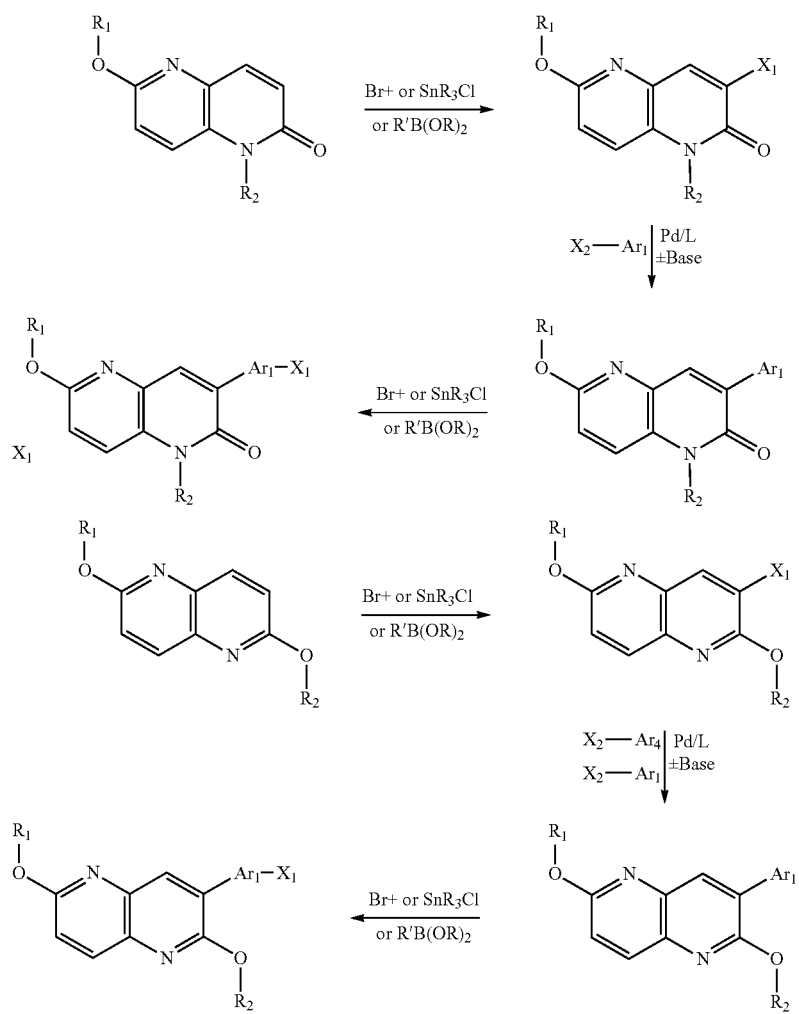

The thione can be accessed from the dione core as shown in Scheme 8, wherein $R^{1,2}$ are for example alkyl groups.

Scheme 8

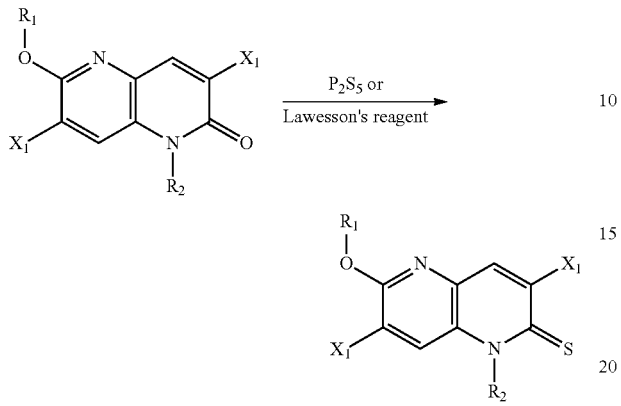

The synthesis of alternating co-polymers of the 2,6-disubstituted-[1,5]naphthyridine and 1-6-disubstituted-1H-[1,5]naphthyridin-2-one cores is shown in Scheme 9. Therein Y1 and Y2 are O or S, X1=Br and X2=SnR$_3$ or X1=Br and X2=B(OR)$_2$ or X1=SnR$_3$ and X2=Br or X1=B(OR)$_2$ and X2=Br or X1=Br or Cl, Ar$_x$ is optionally substituted arylene or heteroarylene as defined in formula III1, and a-d are 0 or 1 with a+b+c+d≥0, and R is for example alkyl.

Scheme 9

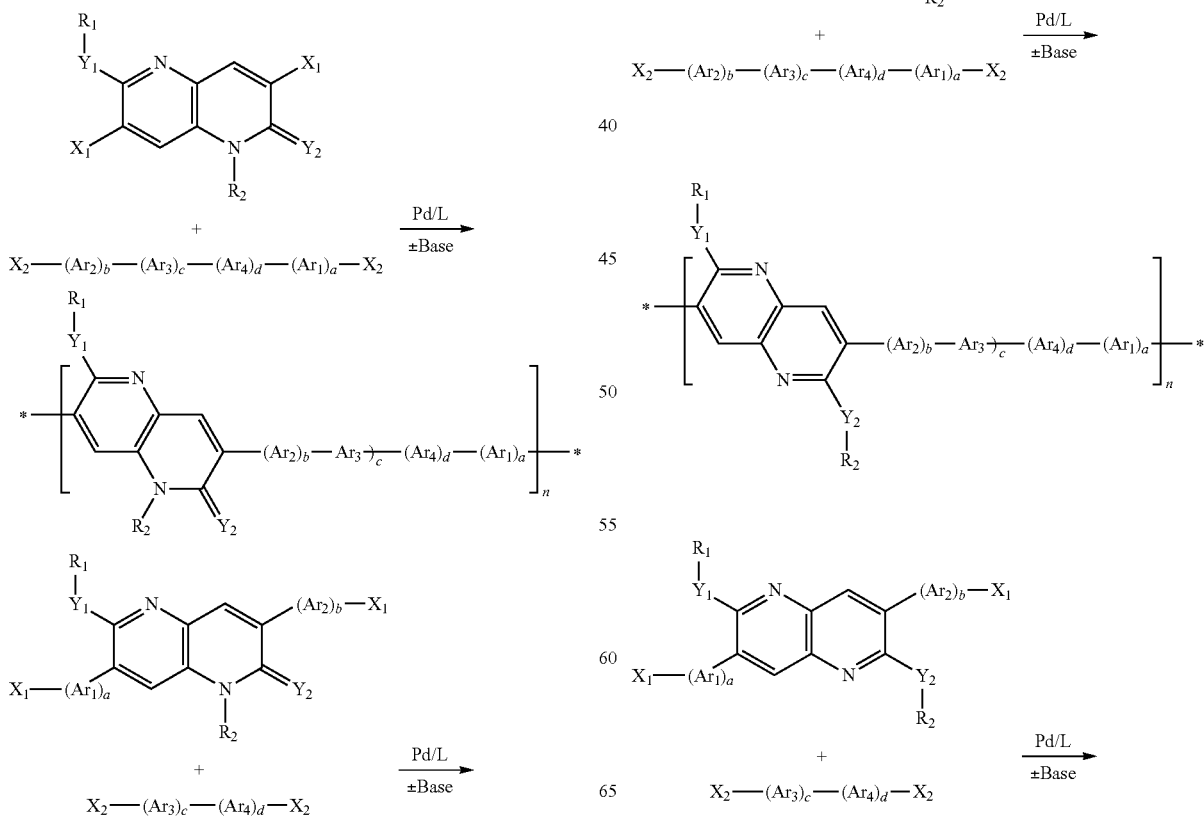

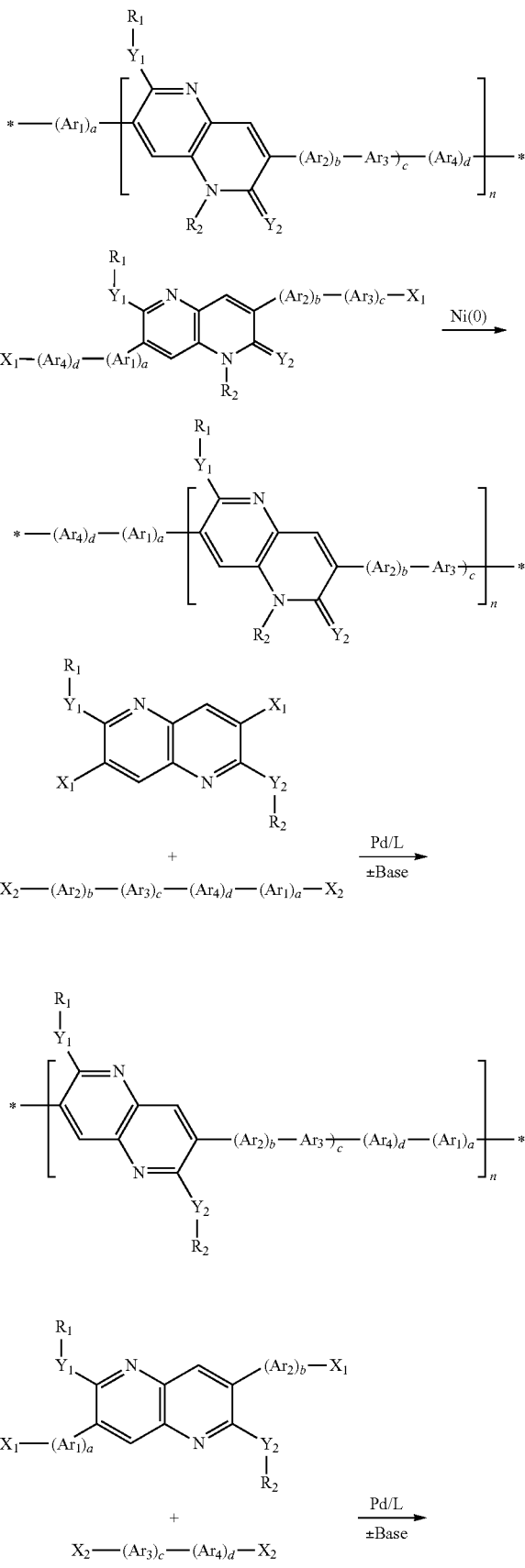

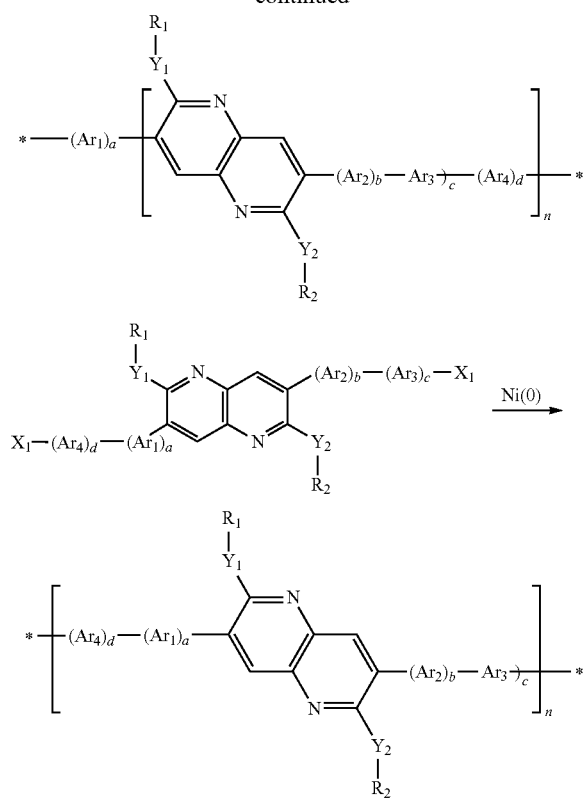

The synthesis of statistical block co-polymers of the 2,6-disubstituted-[1,5]naphthyridine and 1-6-disubstituted-1H-[1,5]naphthyridin-2-one cores is shown in Scheme 10, wherein the individual radicals are as defined in Scheme 9.

Scheme 10

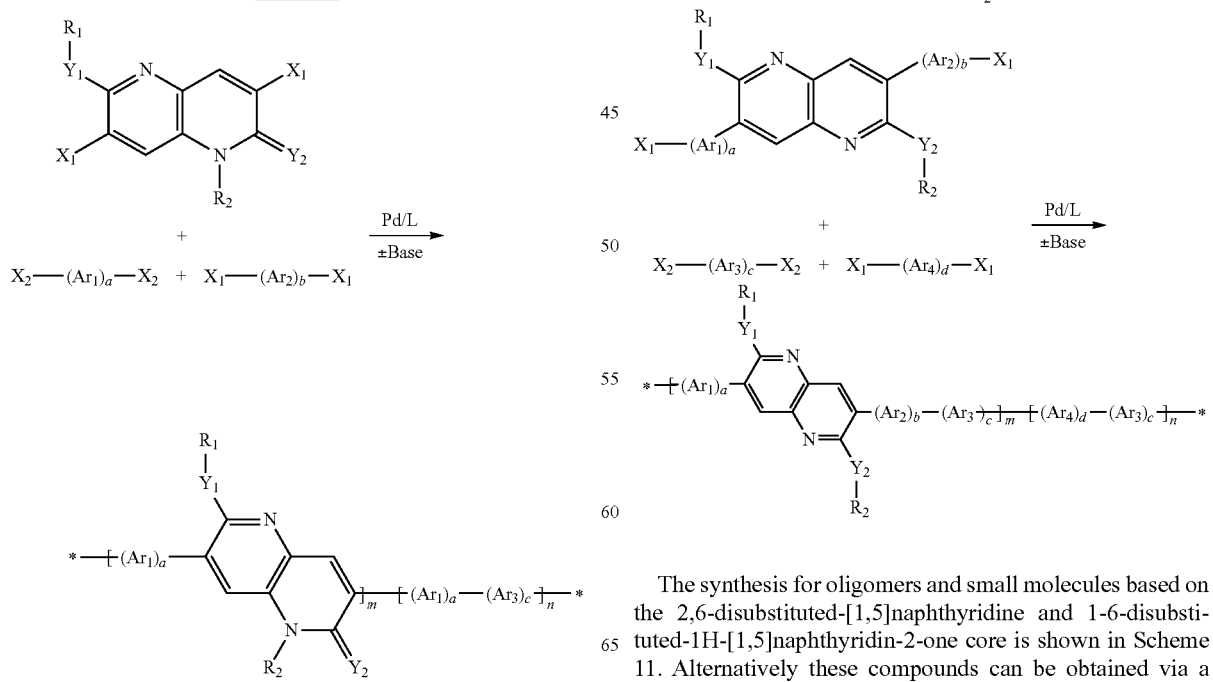

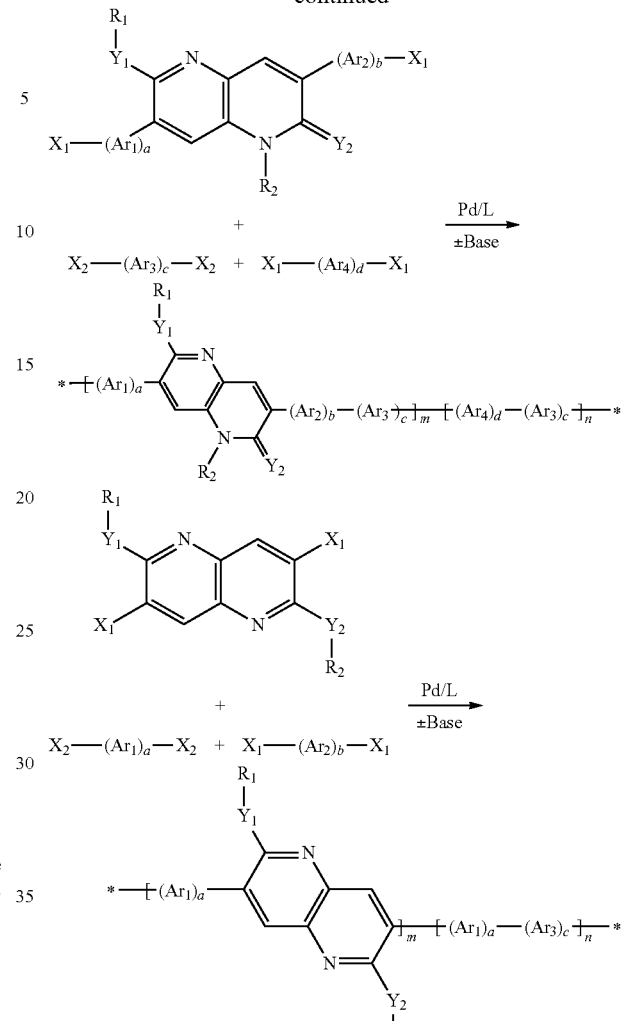

The synthesis for oligomers and small molecules based on the 2,6-disubstituted-[1,5]naphthyridine and 1-6-disubstituted-1H-[1,5]naphthyridin-2-one core is shown in Scheme 11. Alternatively these compounds can be obtained via a convergent synthesis strategy as shown in Scheme 12.

Therein Y1 and Y2 is O or S, X1=Br and X2=SnR$_3$ or B(OR)$_2$ or X1=SnR$_3$ and X2=Br or X1=B(OR)$_2$ and X2=Br, Ar$_{1-8}$ correspond to Ar$^{1-8}$ as defined in formula VI1, and Ar$_5$—Ar$_6$—Ar$_7$—Ar$_8$—R$^2_{end}$ is identical to Ar$_4$—Ar$_3$—Ar$_2$—Ar$_1$—R$^1_{end}$, and R$^1_{end}$ and R$^2_{end}$ correspond to R$^{1t}$ and R$^{2t}$ in formula VI1.
Scheme 11
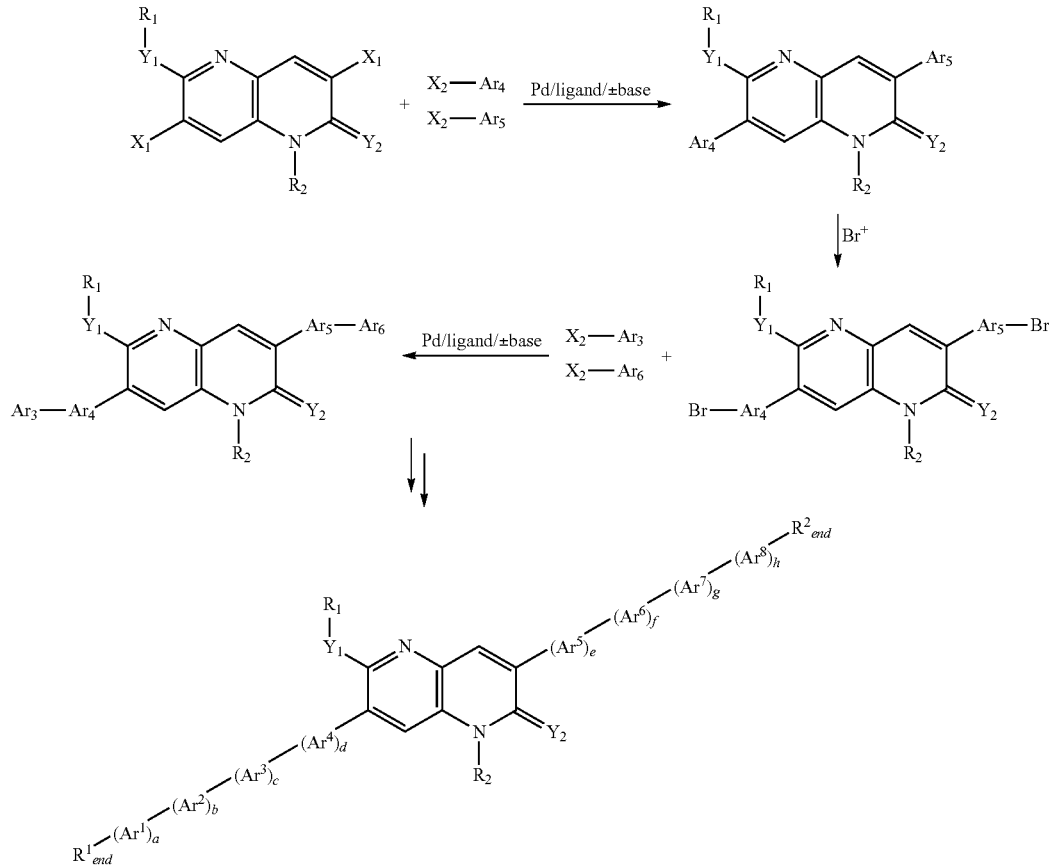
Scheme 12
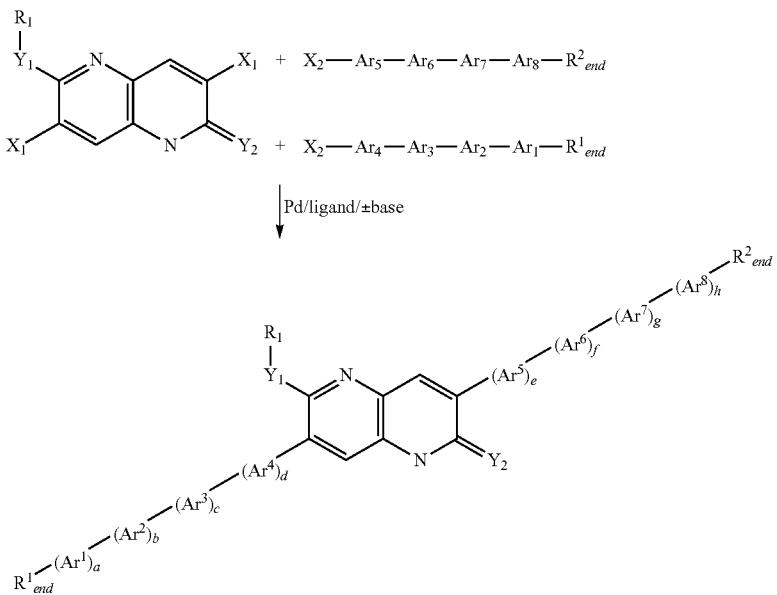

-continued
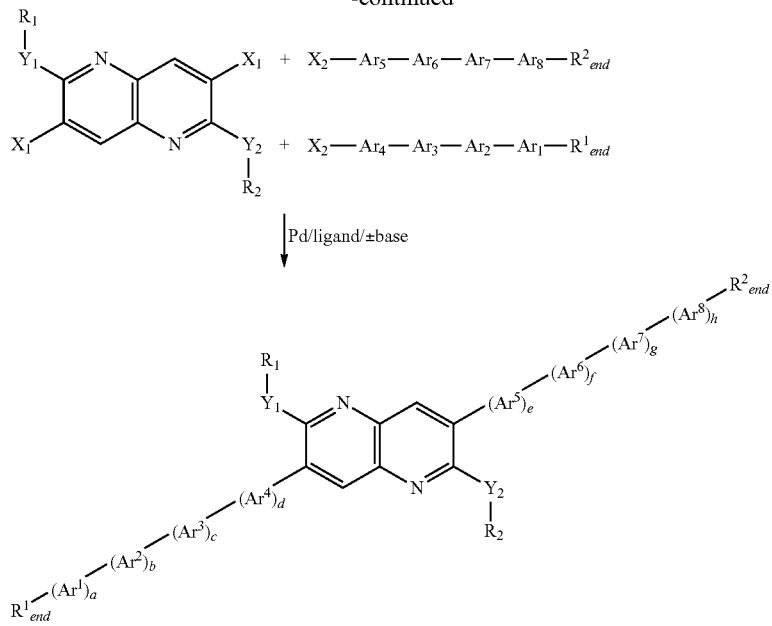
Alternatively the asymmetric small molecules based on 2,6-disubstituted-[1,5]naphthyridine and 1-6-disubstituted-1H-[1,5]naphthyridin-2-one can be obtained via a convergent synthesis strategy as shown in Scheme 13, wherein the individual radicals are as defined in Scheme 11.
Scheme 13
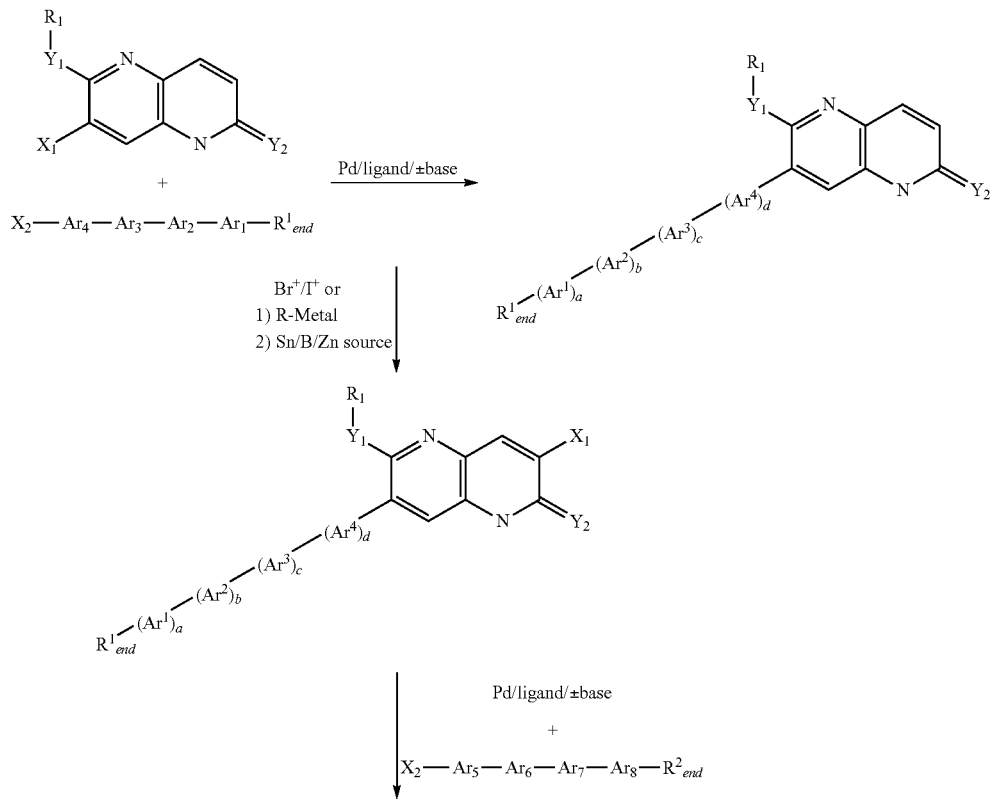

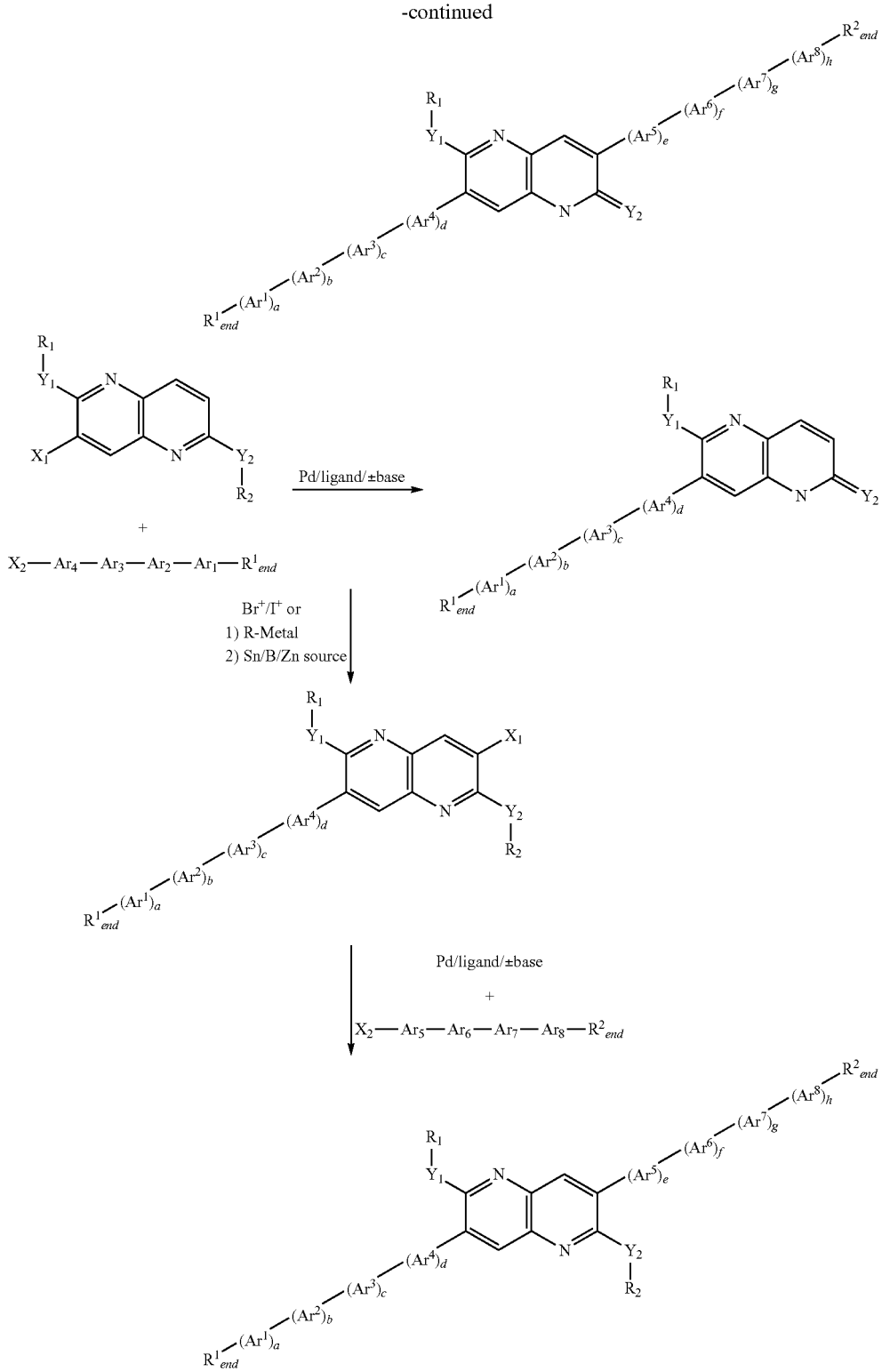
The synthesis of asymmetric compounds containing multiple 2,6-disubstituted-[1,5]naphthyridine and 1-6-disubstituted-1H-[1,5]naphthyridin-2-one units via a convergent synthesis strategy is shown in Scheme 14, wherein the individual radicals are as defined in Scheme 11, and 1<n≤3.

Scheme 14
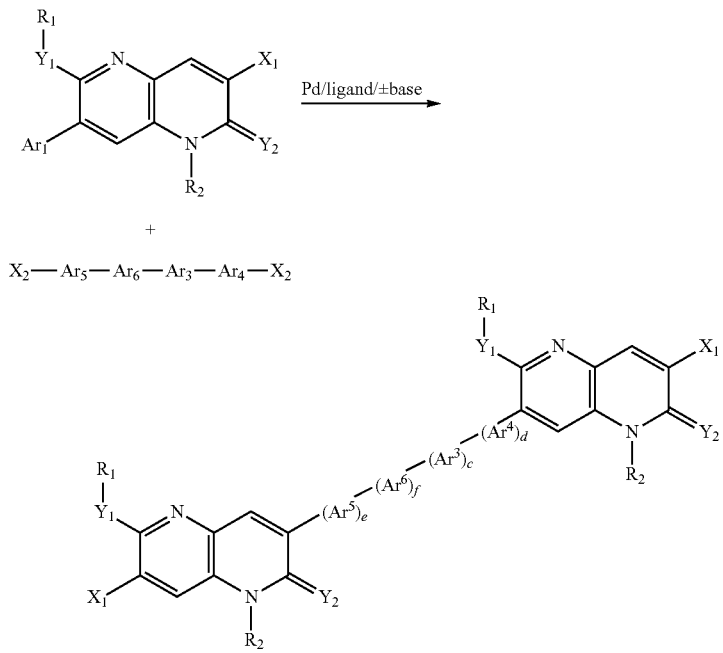
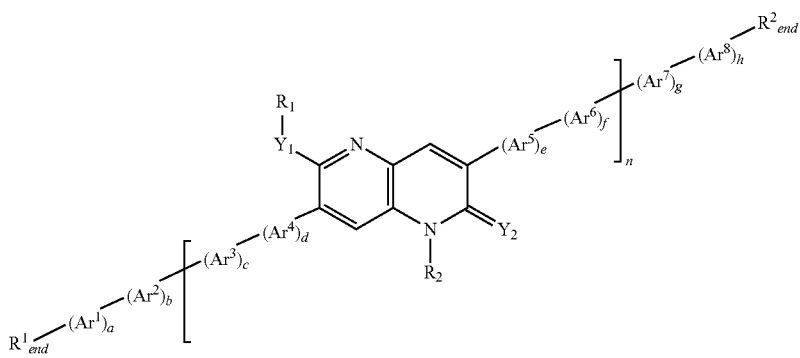
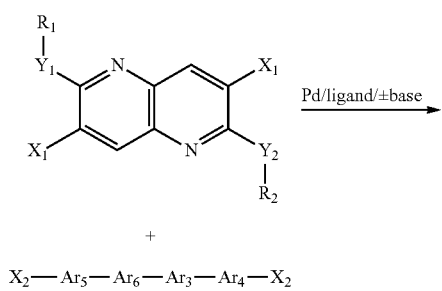

-continued

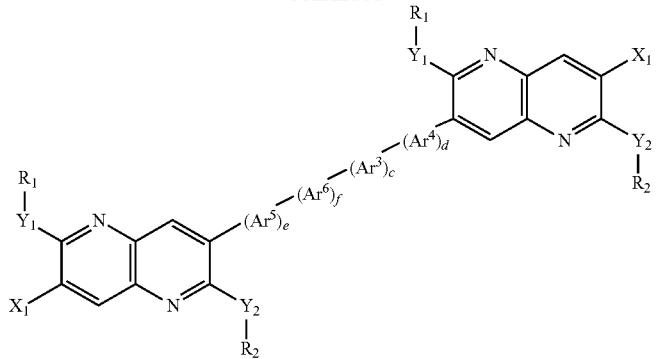

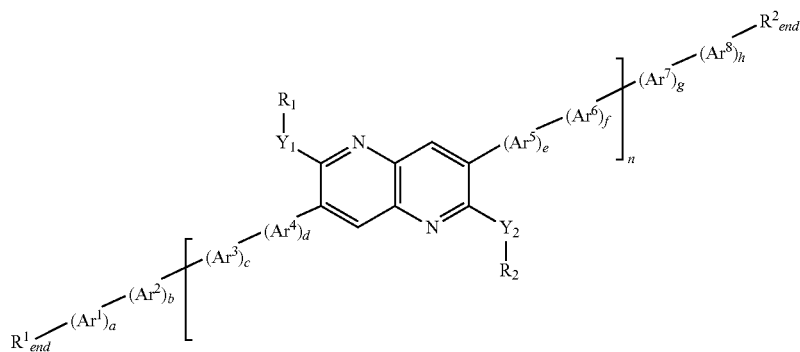

Further substitution can be added to the 2,6-disubstituted-[1,5]naphthyridine and 1-6-disubstituted-1H-[1,5]naphthyridin-2-one cores at the $R^x_{end}$ substitution after the 2,6-disubstituted-[1,5]naphthyridine and 1-6-disubstituted-1H-[1,5]naphthyridin-2-one core organic semiconductors have been prepared as shown in Scheme 15, wherein the individual radicals are as defined in Scheme 14.

Scheme 15

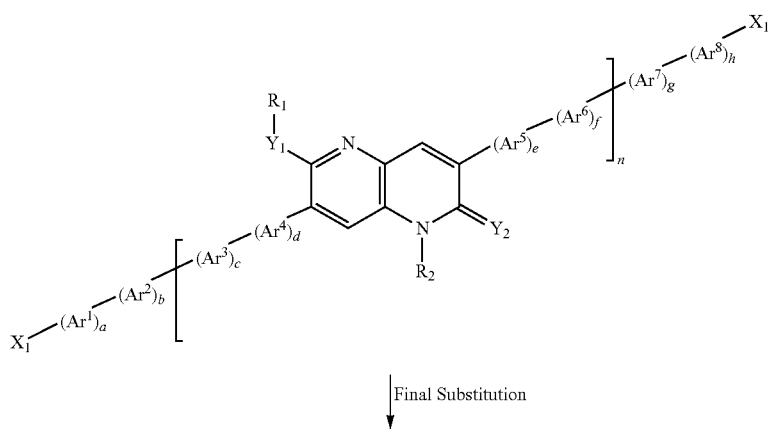

Final Substitution

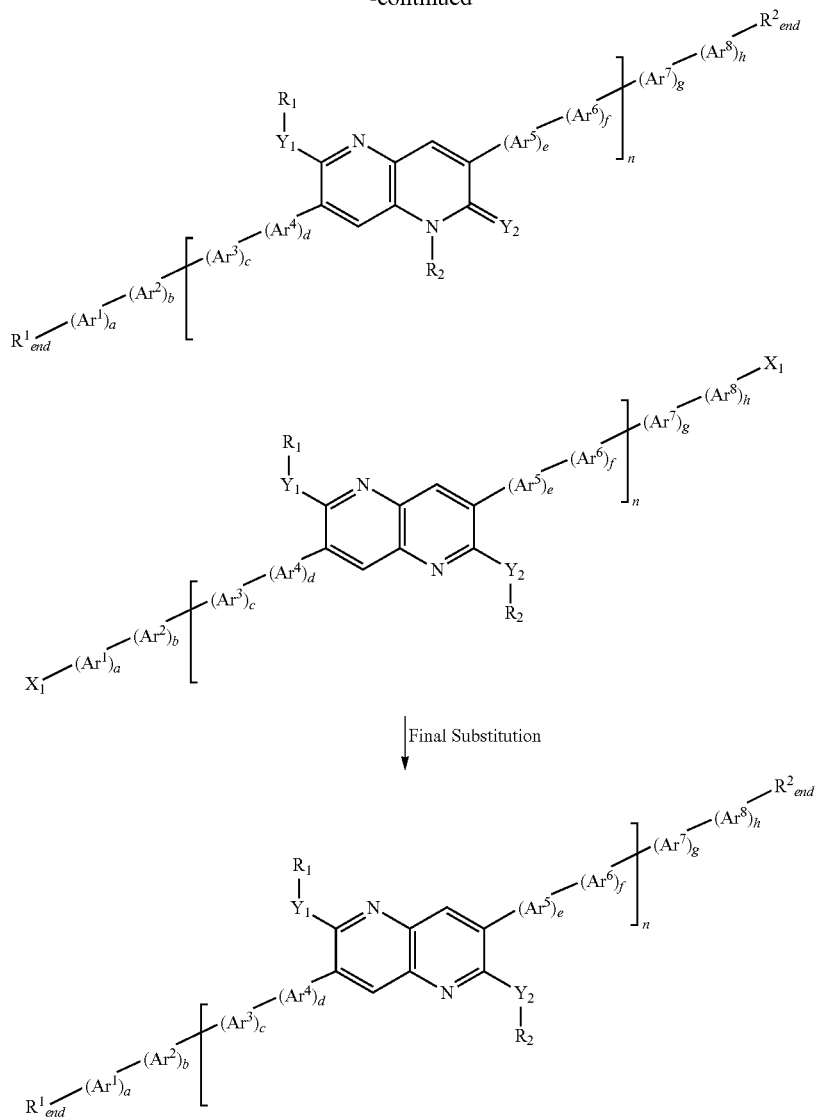

The novel methods of preparing a compound, monomer or polymer as described above and below, and the novel monomers and intermediates used therein, are further aspects of the invention.

The polymer according to the present invention can also be used in mixtures or polymer blends, for example together with monomeric compounds or together with other polymers having charge-transport, semiconducting, electrically conducting, photoconducting and/or light-emitting semiconducting properties, or for example with polymers having hole blocking, electron blocking properties for use as interlayers, charge blocking layers, charge transporting layer in OLED devices, OPV devices or pervorskite based solar cells. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers, polymer blends or mixtures as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethylanisole, N,N-dimethylaniline, ethyl benzoate, 1-fluoro-3,5-dimethoxy-benzene, 1-methylnaphthalene, N-methylpyrrolidinone, 3-fluorobenzotrifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, tetrachloromethane, chlorobenzene, o-dichlorobenzene, 1,2,4-trichlorobenzene, 1,2-dichloroethane, 1,1,1-trichloroethane, 1,1,2,2-tetrachloroethane, 1,8-diiodooctane, 1-chloronaphthalene, 1,8-octane-dithiol, anisole, 2,5-di-methylanisole, 2,4-dimethylanisole, toluene, o-xylene, m-xylene, p-xylene, mixture of o-, m-, and p-xylene isomers, 1,2,4-trimethylbenzene, mesitylene, cyclohexane, 1-methylnaphthalene, 2-methylnaphthalene, 1,2-dimethylnaphthalene, tetraline, decaline, indane, 1-methyl-4-(1-methylethenyl)-cyclohexene (d-Limonene), 6,6-dimethyl-2-methylenebicyclo[3.1.1] heptanes (β-pinene), methyl benzoate, ethyl benzoate, nitrobenzene, benzaldehyde, tetrahydrofuran, 1,4-dioxane, 1,3-dioxane, morpholine, acetone, methylethylketone, ethyl acetate, n-butyl acetate, N,N-dimethylformamide, dimethylacetamide, dimethylsulfoxide and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The polymer according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers, polymer blends, mixtures and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers, polymer blends and mixtures according to the present invention are useful as charge transport, semiconducting, electrically conducting, photoconducting or light emitting material in optical, electrooptical, electronic, electroluminescent or photoluminescent components or devices. In these devices, a polymer, polymer blend or mixture of the present invention is typically applied as a thin layer or film.

Thus, the present invention also provides the use of the polymer, polymer blend, mixture or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, mixture or polymer blend according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, mixture or organic semiconducting layer according to the present invention. Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices the polymer according to the present invention is preferably used in a formulation that comprises or contains, more preferably consists essentially of, very preferably exclusively of, one or more p-type (electron donor) semiconductor and one or more n-type (electron acceptor) semiconductor. The p-type semiconductor is constituted of a least one polymer according to the present invention. The n-type semiconductor can be an inorganic material such as zinc oxide ($ZnO_x$), zinc tin oxide (ZTO), titanium oxide ($TiO_x$), molybdenum oxide ($MoO_x$), nickel oxide ($NiO_x$) or cadmium selenide (CdSe), or an organic material such as graphene or a fullerene, a conjugated polymer or substituted fullerene, for example a (6,6)-phenyl-butyric acid methyl ester derivatized methano $C_{60}$ fullerene, also known as "PCBM-$C_{60}$" or "$C_{60}$PCBM", as disclosed for example in Science 1995, 270, 1789 and having the structure shown below, or structural analogous compounds with e.g. a $C_{70}$ fullerene group or an organic polymer (see for example Coakley, K. M. and McGehee, M. D. Chem. Mater. 2004, 16, 4533).

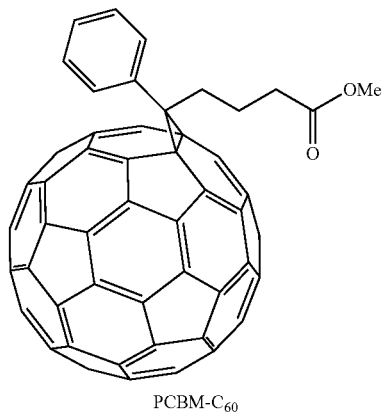

PCBM-$C_{60}$

Preferably the polymer according to the present invention is blended with an n-type semiconductor such as a fullerene or substituted fullerene of formula XII to form the active layer in an OPV or OPD device wherein,

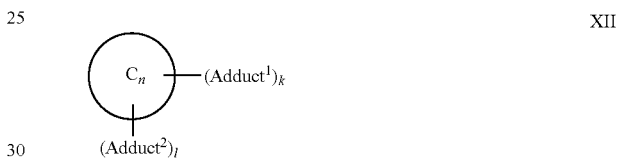

XII $C_n$ denotes a fullerene composed of n carbon atoms, optionally with one or more atoms trapped inside, Adduct[1] is a primary adduct appended to the fullerene $C_n$ with any connectivity, Adduct[2] is a secondary adduct, or a combination of secondary adducts, appended to the fullerene $C_n$ with any connectivity, k is an integer ≥1,
and
l is 0, an integer ≥1, or a non-integer >0.

In the formula XII and its subformulae, k preferably denotes 1, 2, 3 or, 4, very preferably 1 or 2.

The fullerene $C_n$ in formula XII and its subformulae may be composed of any number n of carbon atoms Preferably, in the compounds of formula XII and its subformulae the number of carbon atoms n of which the fullerene $C_n$ is composed is 60, 70, 76, 78, 82, 84, 90, 94 or 96, very preferably 60 or 70.

The fullerene $C_n$ in formula XII and its subformulae is preferably selected from carbon based fullerenes, endohedral fullerenes, or mixtures thereof, very preferably from carbon based fullerenes.

Suitable and preferred carbon based fullerenes include, without limitation, ($C_{60-I_h}$)[5,6]fullerene, ($C_{70-D5h}$)[5,6]fullerene, ($C_{76-D2*}$)[5,6]fullerene, ($C_{84-D2*}$)[5,6]fullerene, ($C_{84-D2d}$)[5,6]fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, $Sc_3$N@$C_{80}$, $Y_3$N@$C_{80}$, $Sc_3C_2$@$C_{80}$ or a mixture of two or more of the aforementioned metallofullerenes.

Preferably the fullerene $C_n$ is substituted at a [6,6] and/or [5,6] bond, preferably substituted on at least one [6,6] bond.

Primary and secondary adduct, named "Adduct" in formula XII and its subformulae, is preferably selected from the following formulae
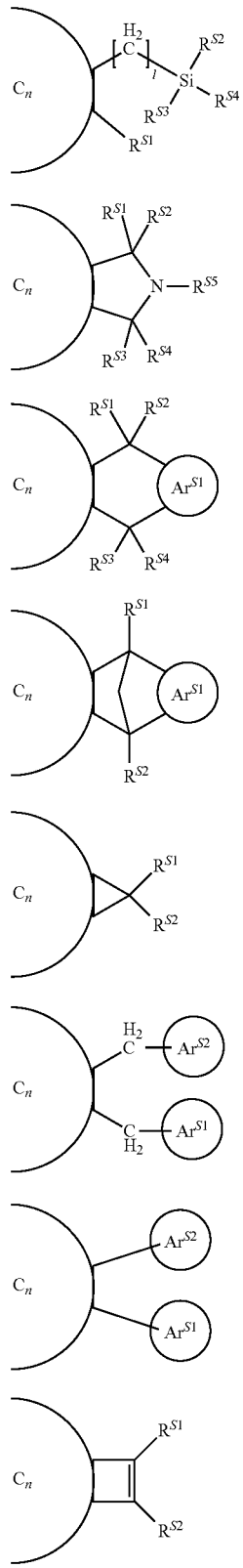
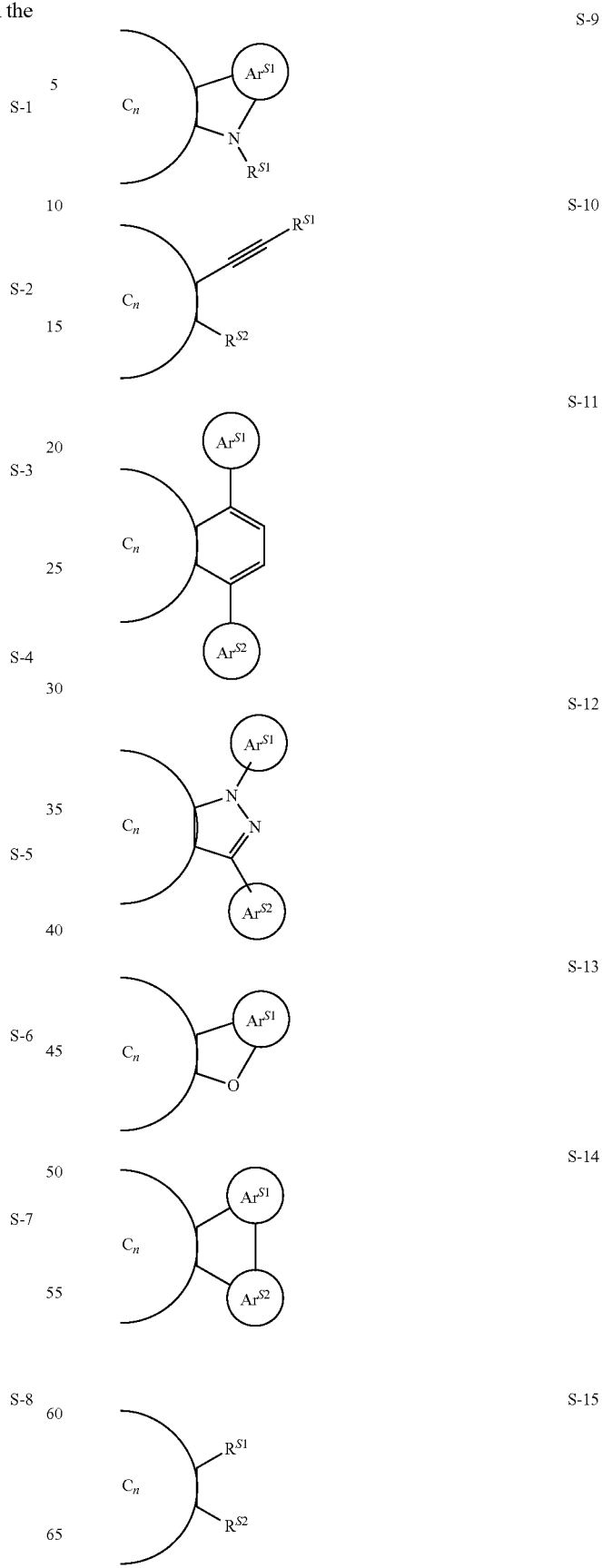

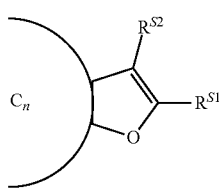

S-16

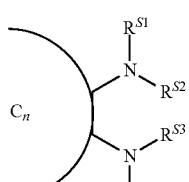

S-17

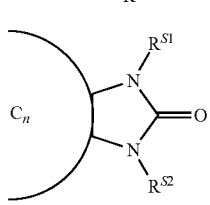

S-18

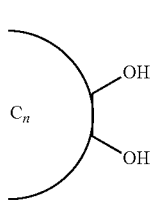

S-19

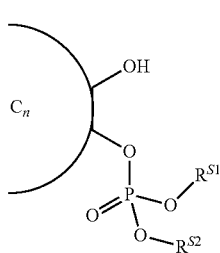

S-20

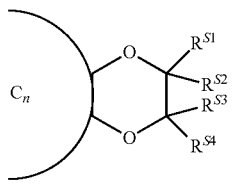

S-21

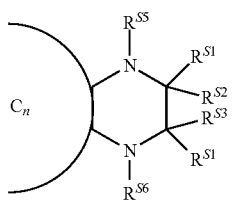

S-22 wherein $C_n$ is as defined in formula XII, $Ar^{S1}$, $Ar^{S2}$ denote, independently of each other, an arylene or heteroarylene group with 5 to 20, preferably 5 to 15, ring atoms, which is mono- or polycyclic, and which is optionally substituted by one or more identical or different substituents having one of the meanings of L as defined above and below, and $R^{S1}$, $R^{S2}$, $R^{S3}$, $R^{S4}$, $R^{S5}$ and $R^{S6}$ independently of each other denote H, CN or have one of the meanings of L as defined above and below.

Preferred compounds of formula XII are selected from the following subformulae:

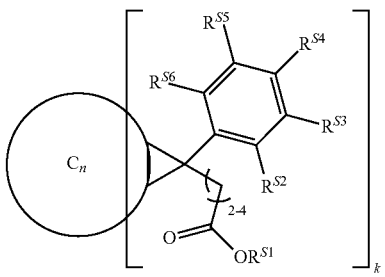

XIIa

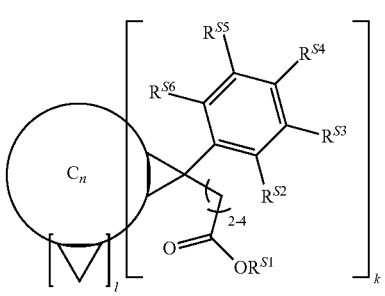

XIIb

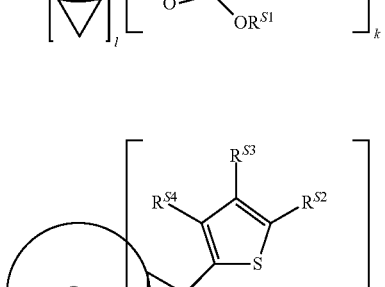

XIIc

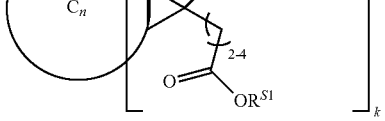

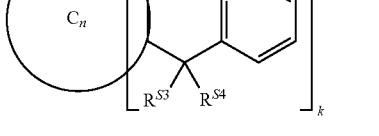

XIId

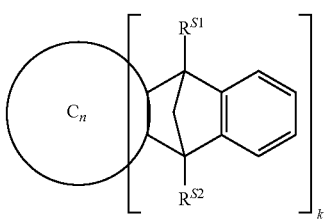

XIIe

-continued

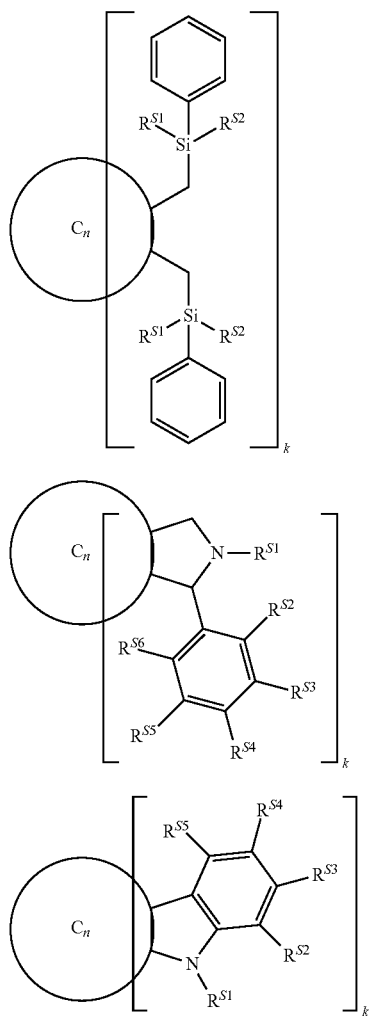

XIIf

XIIg

XIIh wherein $C_n$, k and l are as defined in formula XII, and $R^{S1}$, $R^{S2}$, $R^{S3}$, $R^{S4}$ $R^{S5}$ and $R^{S6}$ independently of each other denote H or have one of the meanings of L as defined above and below.

Also preferably the polymer according to the present invention is blended with other type of n-type semiconductor such as graphene, a metal oxide, like for example, ZnOx, TiOx, ZTO, MoOx, NiOx, quantum dots, like for example, CdSe or CdS, or a conjugated polymer, like for example a polynaphthalenediimide or polyperylenediimide as described, for example, in WO2013142841 A1 to form the active layer in an OPV or OPD device.

The device preferably further comprises a first transparent or semi-transparent electrode on a transparent or semi-transparent substrate on one side of the active layer, and a second metallic or semi-transparent electrode on the other side of the active layer.

Preferably, the active layer according to the present invention is further blended with additional organic and inorganic compounds to enhance the device properties. For example, metal particles such as Au or Ag nanoparticules or Au or Ag nanoprism for enhancements in light harvesting due to near-field effects (i.e. plasmonic effect) as described, for example in *Adv. Mater.* 2013, 25 (17), 2385-2396 and Adv. Ener. Mater. 10.1002/aenm.201400206, a molecular dopant such as 2,3,5,6-tetrafluoro-7,7,8,8-tetracyanoquinodimethane for enhancement in photoconductivity as described, for example in *Adv. Mater.* 2013, 25(48), 7038-7044, or a stabilising agent consisting of a UV absorption agent and/or anti-radical agent and/or antioxidant agent such as 2-hydroxybenzophenone, 2-hydroxyphenylbenzotriazole, oxalic acid anilides, hydroxyphenyl triazines, merocyanines, hindered phenol, N-aryl-thiomorpholine, N-aryl-thiomorpholine-1-oxide, N-aryl-thiomorpholine-1,1-dioxide, N-aryl-thiazolidine, N-aryl-thiazolidine-1-oxide, N-aryl-thiazolidine-1,1-dioxide and 1,4-diazabicyclo[2.2.2]octane as described, for example, in WO2012095796 A1 and in WO2013021971 A1.

The device preferably may further comprise a UV to visible photo-conversion layer such as described, for example, in *J. Mater. Chem.* 2011, 21, 12331 or a NIR to visible or IR to NIR photo-conversion layer such as described, for example, in *J. Appl. Phys.* 2013, 113, 124509.

Further preferably the OPV or OPD device comprises, between the active layer and the first or second electrode, one or more additional buffer layers acting as hole transporting layer and/or electron blocking layer, which comprise a material such as metal oxides, like for example, ZTO, $MoO_x$, $NiO_x$ a doped conjugated polymer, like for example PEDOT:PSS and polypyrrole-polystyrene sulfonate (PPy: PSS), a conjugated polymer, like for example polytriarylamine (PTAA), an organic compound, like for example substituted triaryl amine derivatives such as N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), graphene based materials, like for example, graphene oxide and graphene quantum dots or alternatively as hole blocking layer and/or electron transporting layer, which comprise a material such as metal oxide, like for example, $ZnO_x$, $TiO_x$, AZO (aluminium doped zinc oxide), a salt, like for example LiF, NaF, CsF, a conjugated polymer electrolyte, like for example poly[3-(6-trimethylammoniumhexyl) thiophene], poly(9,9-bis(2-ethylhexyl)-fluorene]-b-poly[3-(6-trimethylammoniumhexyl)thiophene], or poly[(9,9-bis (3'-(N,N-dimethylamino)propyl)-2,7-fluorene)-alt-2,7-(9,9-dioctylfluorene)], a polymer, like for example poly (ethyleneimine) or crosslinked N-containing compound derivatives or an organic compound, like for example tris (8-quinolinolato)-aluminium(III) ($Alq_3$), phenanthroline derivative or $C_{60}$ or $C_{70}$ based fullerenes, like for example, as described in *Adv. Energy Mater.* 2012, 2, 82-86.

In a blend or mixture of a polymer according to the present invention with a fullerene or modified fullerene, the ratio polymer:fullerene is preferably from 5:1 to 1:5 by weight, more preferably from 2:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the polymers, polymer blends or mixtures of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing a blend or mixture of a polymer according to the present invention with a fullerene or modified fullerene like PCBM are preferably prepared. In the preparation of such a formulation, suitable solvents are preferably selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to dichloromethane, trichloromethane, tetrachloromethane, chlorobenzene, o-dichlorobenzene, 1,2,4-trichlorobenzene, 1,2-dichloroethane, 1,1,1-trichloroethane, 1,1,2,2-tetrachloroethane, 1,8-diiodooctane, 1-chloronaphthalene, 1,8-octane-dithiol, anisole, 2,5-di-methylanisole, 2,4-dimethylanisole, toluene, o-xylene, m-xylene, p-xylene, mixture of xylene o-, m-, and p-isomers, 1,2,4-trimethylbenzene, mesitylene, cyclohexane, 1-methylnaphthalene, 2-methylnaphthalene, 1,2-dimethylnaphthalene, tetraline, decaline, indane, 1-methyl-4-(1-methylethenyl)-cyclohexene (d-Limonene), 6,6-dimethyl-2-methylenebicyclo[3.1.1]heptanes (β-pinene), methyl benzoate, ethyl benzoate, nitrobenzene, benzaldehyde, tetrahydrofuran, 1,4-dioxane, 1,3-dioxane, morpholine, acetone, methylethylketone, ethyl acetate, n-butyl acetate, N,N-dimethylformamide, dimethylacetamide, dimethylsulfoxide and/or mixtures thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
optionally a substrate,
a high work function electrode, preferably comprising a metal oxide, like for example ITO and FTO, serving as anode,
an optional conducting polymer layer or hole transport layer, preferably comprising an organic polymer or polymer blend, for example PEDOT:PSS (poly(3,4-ethylenedioxythiophene):poly(styrene-sulfonate), substituted triaryl amine derivatives, for example, TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
a layer, also referred to as "active layer", comprising of at least one p-type and at least one n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF, $TiO_x$, $ZnO_x$, PFN, a poly(ethyleneimine) or crosslinked nitrogen containing compound derivatives or a phenanthroline derivatives
a low work function electrode, preferably comprising a metal like for example aluminum, serving as cathode,
wherein at least one of the electrodes, preferably the anode, is transparent to visible and/or NIR light, and
wherein at least one p-type semiconductor is a polymer according to the present invention.

A second preferred OPV device according to the invention is an inverted OPV device and comprises the following layers (in the sequence from bottom to top):
optionally a substrate,
a high work function metal or metal oxide electrode, comprising for example ITO and FTO, serving as cathode,
a layer having hole blocking properties, preferably comprising a metal oxide like $TiO_x$ or $ZnO_x$, or comprising an organic compound such as polymer like poly(ethyleneimine) or crosslinked nitrogen containing compound derivatives or phenanthroline derivatives,
an active layer comprising at least one p-type and at least one n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic polymer or polymer blend, for example of PEDOT:PSS or substituted triaryl amine derivatives, for example, TBD or NBD,
an electrode comprising a high work function metal like for example silver, serving as anode,
wherein at least one of the electrodes, preferably the cathode, is transparent to visible and/or NIR light, and
wherein at least one p-type semiconductor is a polymer according to the present invention.

In the OPV devices of the present invention the p-type and n-type semiconductor materials are preferably selected from the materials, like the polymer/fullerene systems or polymer/polymer systems, as described above When the active layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, 1-chloronaphthalene, N,N-dimethylformamide, dimethylacetamide, dimethylsulfoxide and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

The polymers, polymer blends, mixtures and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a polymer, polymer blend, mixture or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
  wherein the semiconductor layer preferably comprises a polymer, polymer blend or mixture according to the present invention.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the polymers, polymer blends and mixtures according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emissive layer where their recombination leads to the excitation and hence luminescence of the lumophor units contained in the emission layer.

The polymers, polymer blends and mixtures according to the invention can be employed in one or more of a buffer layer, electron or hole transport layer, electron or hole blocking layer and emissive layer, corresponding to their electrical and/or optical properties. Furthermore their use within the emissive layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the polymers, polymer blends and mixtures according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of a polymer according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of a polymer of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The polymers, polymer blends and mixtures according to the present invention may also be suitable for use in organic plasmon-emitting diodes (OPEDs), as described for example in Koller et al., *Nat. Photonics,* 2008, 2, 684.

According to another use, the polymers according to the present invention can be used alone or together with other materials in or as alignment layers in LCD or OLED devices, as described for example in US 2003/0021913. The use of charge transport polymers according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The polymers according to the present invention having mesogenic or liquid crystalline properties can form oriented anisotropic films as described above, which are especially useful as alignment layers to induce or enhance alignment in a liquid crystal medium provided onto said anisotropic film. The polymers according to the present invention may also be combined with photoisomerisable compounds and/or chromophores for use in or as photoalignment layers, as described in US 2003/0021913 A1.

According to another use the polymers, polymer blends and mixtures according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant ε ("permittivity") refer to values taken at 20° C. and 1,000 Hz.

The invention will now be described in more detail by reference to the following examples, which are illustrative only and do not limit the scope of the invention.

EXAMPLES

Example 1: 3,3'-([2,2':5',2"-Terthiophene]-5,5"-diyl) bis(1-dodecyl-6-dodecoxynaphthyridine-2-one ((NDO)2-3T) (6)

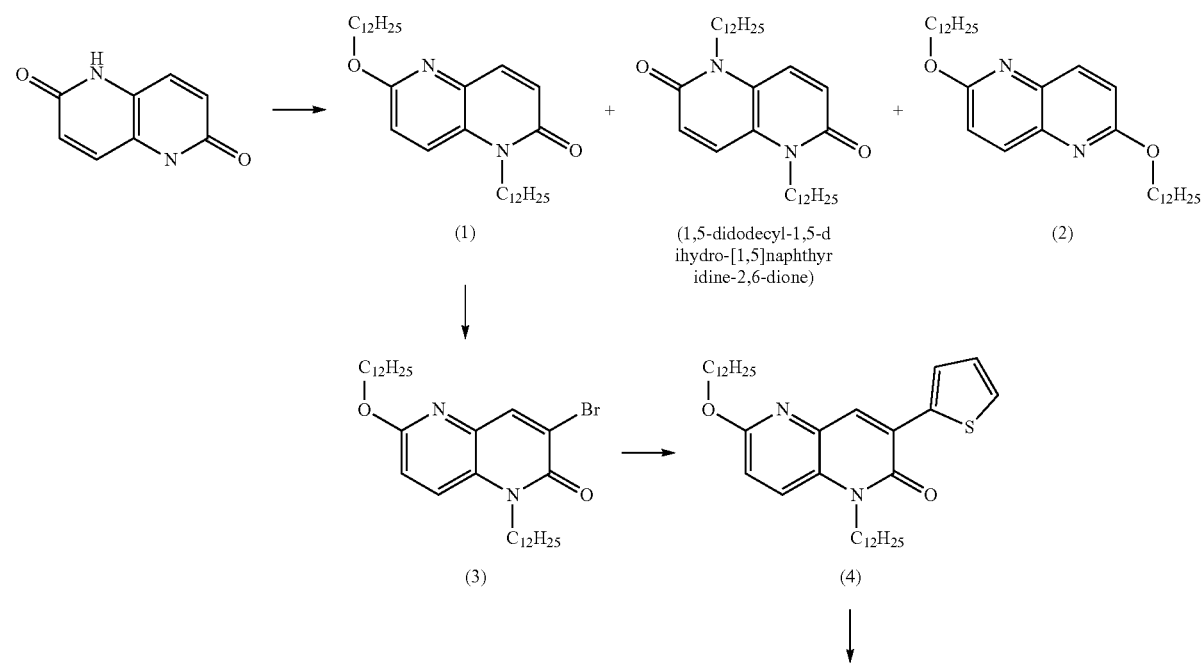

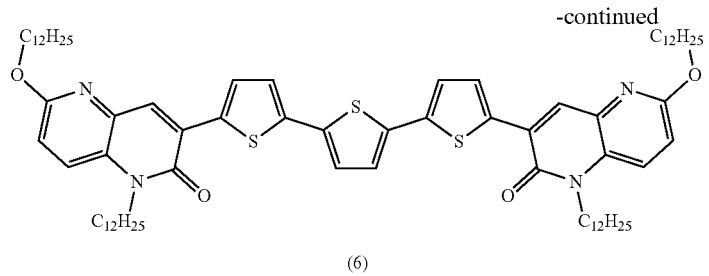

(6)

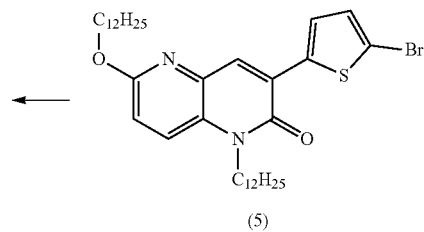

(5)

1-Dodecyl-6-(dodecoxy)naphthyridine-2-one (1)

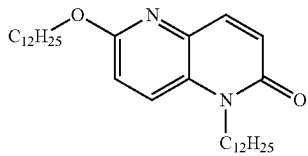

(1)

1,5-Dihydro-[1,5]naphthyridine-2,6-dione (5.0 g, 31 mmol) is added to a solution of 1-bromododecane (50 cm$^3$, 208 mmol), 40% tetrabutylammonium hydroxide in water (247 cm$^3$, 370 mmol) and dimethylsulfoxide (60 cm$^3$). The reaction mixture is stirred at 65° C. for 4 days before precipitation of the crude product by addition of saturated ammonium chloride solution (50 cm$^3$). The crude solid is suspended in a 1:1 mixture of ethyl acetate:petroleum ether, and the solids collected and purified via column chromatography (eluent=20%→100% ethyl acetate/hexane). 1-Dodecyl-6-(dodecoxy)naphthyridine-2-one was formed in highest yield as an off-white solid. Yield=6.35 g (41%). 1H NMR (400 MHz, CDCl3) δ 7.72 (d, J=9.7 Hz, 1H), 7.59 (d, J=9.2 Hz, 1H), 6.94 (d, J=9.2 Hz, 1H), 6.85 (d, J=9.7 Hz, 1H), 4.34 (t, J=6.7 Hz, 2H), 4.27-4.15 (m, 2H), 1.87-1.64 (m, 4H), 1.51-1.16 (m, 36H), 0.88 (t, J=6.8 Hz, 6H); 13C NMR (101 MHz, CDCl3) δ 161.2, 159.3, 139.6, 135.5, 131.3, 125.5, 125.2, 114.2, 66.5, 42.7, 32.1, 29.81, 29.75, 29.70, 29.68, 29.54, 29.52, 29.48, 29.1, 28.1, 27.1, 26.2, 22.8, 14.2; m/z (MALDI): 499.59 (M+H)+; Elemental Analysis: Found: C, 77.21; H, 11.19; N, 5.60; Expected: C, 77.06; H, 10.91; N, 5.62; Melting point: 72-74° C.

The other isomers isolated are 1,5-didodecyl-1,5-dihydro-[1,5]naphthyridine-2,6-dione as a yellow solid, yield=1.86 g (12%), and 2,6-didodecoxynaphthyridine, below.

2,6-Didodecoxynaphthyridine (2)

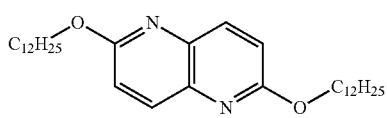

(2)

White solid. Yield=4.34 g (28%) 1H NMR (400 MHz, CDCl3) δ 7.95 (d, J=8.8 Hz, 1H), 7.00 (d, J=8.8 Hz, 1H), 4.40 (t, J=6.7 Hz, 2H), 1.86-1.76 (m, 2H), 1.48 (dt, J=15.0, 6.7 Hz, 2H), 1.42-1.19 (m, 16H), 0.88 (t, J=6.9 Hz, 3H); 13C NMR (101 MHz, CDCl3) δ 161.0, 139.2, 138.0, 115.7, 66.4, 32.1, 29.82, 29.75, 29.6, 29.5, 29.2, 26.3, 22.8, 14.2; m/z (MALDI): 499.49 [M]+: Elemental analysis: Found: C, 77.37, H, 11.07, N, 5.64; Expected: C, 77.06, H, 10.91, N, 5.64; Melting point: 76-78° C.

3-Bromo-1-dodecyl-6-dodecoxynaphthyridine-2one (3)

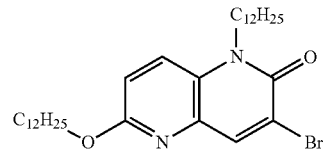

(3)

1-Dodecyl-6-decoxynaphthyridine-2-one (compound 1) (4 g, 8.02 mmol) is added to a flask before the addition of chloroform (32.6 cm$^3$) and acetic acid (14.5 cm$^3$). The flask is then cooled to 0° C. before the dropwise addition of bromine (1.24 cm$^3$, 24.06 mmol). The reaction is then allowed to react at reflux for 16 hours. The reaction mixture is diluted with dichloromethane (40 cm$^3$) and washed with brine (3×100 cm$^3$). The crude product is then purified by column chromatography (1:5 dichloromethane/hexane) to yield the product. Yield=4.40 g (95%). 1H NMR (500 MHz, CDCl3) δ 8.22 (s, 1H), 7.59 (d, J=9.2 Hz, 1H), 6.98 (d, J=9.2 Hz, 1H), 4.34 (t, J=6.7 Hz, 2H), 4.31-4.24 (m, 2H), 1.85-1.68 (m, 4H), 1.50-1.21 (m, 38H), 0.88 (t, J=6.9 Hz, 6H) 13C NMR (101 MHz, CDCl3) δ 159.6, 157.4, 141.2, 134.7, 130.8, 125.7, 121.5, 114.7, 77.5, 77.2, 76.8, 66.7, 44.5, 32.0, 29.78, 29.75, 29.72, 29.66, 29.63, 29.60, 29.50, 29.45, 29.0, 28.0, 27.0, 26.2, 22.8, 14.21, 14.18, 14.15; m/z (MALDI): 577.37 [M]+; Elemental analysis: Found: C, 66.40; H, 9.36; N, 4.85; Expected: C, 66.53; H, 9.25; N, 4.85; Melting point: 61-63° C.

3-(Thiophen-2-yl)-1-dodecyl-6-dodecoxynaphthyridine-2-one (4)

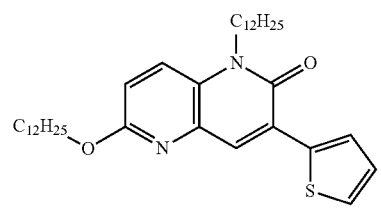

(4)

3-Bromo-1-dodecyl-6-dodecoxynaphthyridine-2one (compound 3) (2.5 g, 4.33 mmol) and 2-tributylstannylthiophene (1.51 cm³, 4.76 mmol) are added to a round bottom flask which is subsequently evacuated and purged with nitrogen before the addition of anhydrous N,N-dimethylformamide (155 cm³). The mixture is degassed by bubbling nitrogen through the solution for 45 minutes before the addition of Pd(PPh3)4 (0.35 g, 0.303 mmol). The reaction is allowed to stir at reflux for 16 hours. The reaction mixture is allowed to cool before, being diluted in 100 cm³ of dichloromethane and washed with saturated aqueous NaHCO₃ solution (3×250 cm³) and water (2×250 cm³). The solvent is removed by evaporation and the crude product is purified by column chromatography (hexane). Yield=1.85 g (73%). 1H NMR (400 MHz, CDCl3) δ 8.22 (s, 1H), 7.83 (dd, J=3.8, 1.1 Hz, 1H), 7.60 (d, J=9.2 Hz, 1H), 7.48 (dd, J=5.1, 1.1 Hz, 1H), 7.14 (dd, J=5.1, 3.8 Hz, 1H), 6.93 (d, J=9.1 Hz, 1H), 4.39 (t, J=6.7 Hz, 2H), 4.36-4.27 (m, 2H), 1.87-1.71 (m, 4H), 1.53-1.19 (m, 36H), 0.89 (t, J=6.9 Hz, 6H) 13C NMR (101 MHz, CDCl3) δ 159.7, 159.2, 137.2, 135.3, 132.3, 130.0, 128.9, 128.2, 126.7, 126.0, 125.2, 113.9, 66.5, 43.6, 32.1, 29.81, 29.75, 29.69, 29.66, 29.63, 29.60, 29.56, 29.51, 29.47, 29.4, 29.2, 28.1, 28.0, 27.2, 27.0, 26.2, 22.8, 17.6, 14.2, 13.7; m/z (MALDI): 580.48 [M]₊ Elemental Analysis: Found: C, 74.20; H, 9.66; N, 4.72; Expected: C, 74.43; H, 9.72; N, 4.82; Melting point: 64-66° C.

3-(5-Bromothiophen-2-yl)-1-dodecyl-6-dodecoxynaphthyridine-2-one (5)

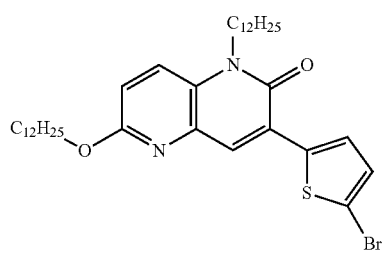

(5)

3-(Thiophen-2-yl)-1-dodecyl-6-dodecoxynaphthyridine-2-one (Compound 4) (1.75 g, 3.02 mmol), N-bromosuccinimide (0.591 g, 3.32 mmol) and chloroform (125 cm³) are added to a round bottom flask and the reaction mixture is allowed to stir at room temperature for 16 hours in the absence of light. The reaction mixture is then washed with brine (3×150 cm³) and the solvent is evaporated before purification by column chromatography (1:5 dichloromethane/hexane). Yield=1.79 g (90%). 1H NMR (400 MHz, CDCl3) δ 8.19 (s, 1H), 7.62 (d, J=9.2 Hz, 1H), 7.53 (d, J=4.1 Hz, 1H), 7.11 (d, J=4.1 Hz, 1H), 6.96 (d, J=9.1 Hz, 1H), 4.39 (t, J=6.7 Hz, 2H), 4.36-4.27 (m, 2H), 1.87-1.71 (m, 4H), 1.53-1.17 (m, 36H), 0.89 (t, J=6.9 Hz, 6H); 13C NMR (101 MHz, CDCl3) δ 159.9, 159.1, 138.2, 135.2, 131.4, 130.0, 129.3, 127.5, 125.3, 125.1, 117.2, 114.2, 66.6, 43.7, 32.1, 29.82, 29.75, 29.7, 29.6, 29.5, 29.2, 28.1, 27.2, 26.2, 22.8, 14.2; m/z (MALDI): 659.17 [M]+; Elemental Analysis: Found: C, 65.48; H, 8.35; N, 4.31; Expected: C, 65.53; H, 8.40; N, 4.31; Melting point: 59-61° C.

3,3'-([2,2':5',2''-Terthiophene]-5,5''-diyl)bis(1-dodecyl-6-dodecoxynaphthyridine-2-one ((NDO)2-3T) (6)

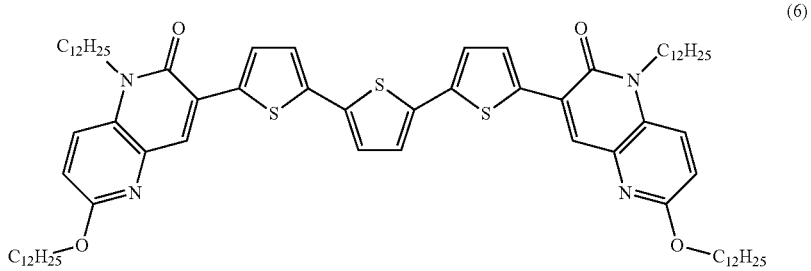

(6)

3-(5-Bromothiophen-2-yl)-1-dodecyl-6-dodecoxynaphthyridine-2-one (compound 5) (0.747 g, 1.07 mmol) and 2,5-bistrimethylstannylthiophene (0.2 g, 0.49 mmol) are added to a flask which is evacuated and purged before the addition of anhydrous N,N-dimethylformamide (13 cm³). The solution is then degassed using nitrogen for 45 minutes before the addition of Pd(PPh3)4 (0.079 g, 0.068 mmol). The reaction is allowed to react at reflux for 16 hours. Once cooled to room temperature, the solution is diluted with dichloromethane (15 cm³) and washed with saturated NaHCO₃ (aq.) solution (3×40 cm³) and water (2×40 cm³). The solvent is then removed by evaporation and the compound is purified by column chromatography (1:2.5 ethyl acetate/hexane). Yield=0.13 g (21%). 1H NMR (400 MHz, CDCl3) δ 8.21 (s, 1H), 7.72 (d, J=4.0 Hz, 1H), 7.60 (d, J=9.2 Hz, 1H), 7.21 (d, J=4.3 Hz, 2H), 6.92 (d, J=9.1 Hz, 1H), 4.39 (t, J=6.7 Hz, 2H), 4.36-4.28 (m, 2H), 1.87-1.72 (m, 4H), 1.54-1.19 (m, 36H), 0.89 (t, J=6.7 Hz, 6H); 13C NMR (101 MHz, CDCl3) δ 159.2, 158.5, 139.9, 136.2, 135.22, 134.7, 130.8, 129.3, 127.2, 125.9, 124.5, 124.1, 122.8, 113.2, 65.9, 43.1, 31.4, 29.2, 29.1, 29.1, 28.9, 28.9, 28.8, 28.5, 27.5, 26.6, 25.6, 22.2, 13.6; m/z (MALDI): 1241.99 [M]+; Elemental Analysis: Found: C, 73.06, H, 8.98, N, 4.74, Expected: C, 73.50, H, 9.09, N, 4.51.

Example 2: 3,3'-(Benzo[1,2,5]thiadiazole-4,7-diyl-bis(thiophene,5,2-diyl))bis(1-dodecyl-6-dodecoxynaphthyridine-3-one) ((NDO-T)2-BT) (7)

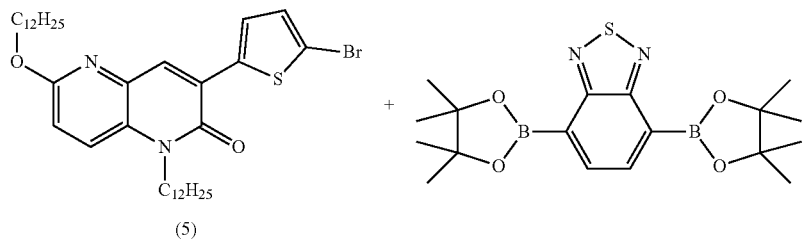

(5)

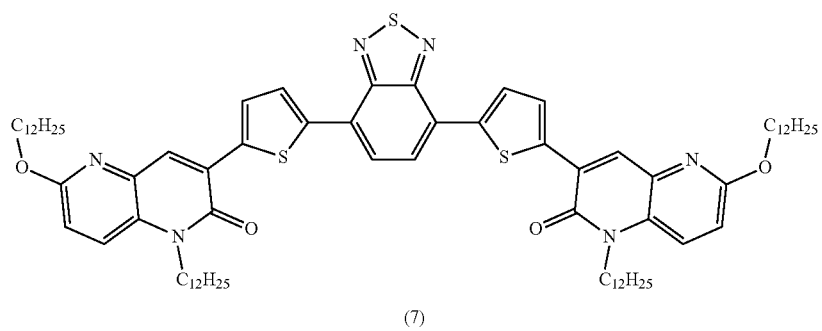

(7)

3,3'-(Benzo[1,2,5]thiadiazole-4,7-diylbis(thiophene,5,2-diyl))bis(1-dodecyl-6-dodecoxynaphthyridine-3-one) ((NDO-T)2-BT) (7)

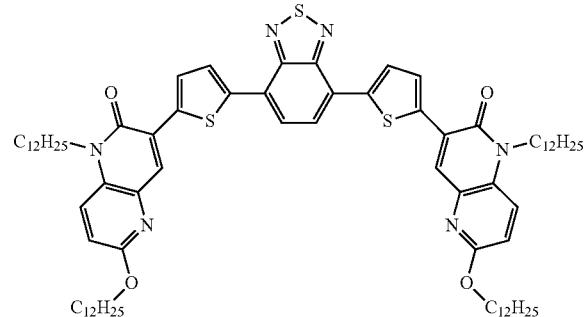

3-(5-Bromothiophen-2-yl)-1-dodecyl-6-dodecoxynaphthyridine-2-one (compound 5) (1.8 g, 2.73 mmol) and 2,1,3-benzothiadiazole-4,7-bis(boronic acid pinacol ester) (0.33 g, 0.85 mmol) and potassium carbonate (0.352 g, 2.55 mmol) are added to a flask which is evacuated and purged with nitrogen before the addition of anhydrous tetrahydrofuran (20 cm$^3$) and degassed water (0.7 cm$^3$). The solution is degassed using nitrogen for 45 minutes before the addition of Pd(PPh$_3$)$_4$ (0.196 g, 0.17 mmol). The reaction mixture is then allowed to react at reflux for 16 hours. The mixture is allowed to cool to room temperature before being diluted with tetrahydrofuran (20 cm$^3$) and washed with brine (3×50 cm$^3$) before the solvent is evaporated. The crude product is purified by column chromatography (1:5 dichloromethane/hexane). Yield=0.29 g (26%). 1H NMR (400 MHz, CDCl3) δ 8.26 (s, 1H), 8.23 (d, J=4.1 Hz, 1H), 7.97 (s, 1H), 7.87 (d, J=4.1 Hz, 1H), 7.59 (d, J=9.2 Hz, 1H), 6.91 (d, J=9.1 Hz, 1H), 4.45-4.30 (m, 4H), 1.89-1.72 (m, 4H), 1.55-1.20 (m, 36H), 0.89 (t, J=6.6 Hz, 6H); 13C NMR (101 MHz, CDCl3) δ 159.1, 158.5, 152.2, 141.9, 137.3, 134.6, 131.3, 129.5, 127.3, 127.1, 126.3, 125.5, 125.2, 124.5, 113.3, 65.9, 43.1, 31.4, 29.2, 29.1, 29.0, 28.9, 28.9, 28.6, 27.5, 26.6, 25.6, 22.2, 13.6; m/z (MALDI): 1293.96 [M]+; Elemental Analysis: Found: C, 72.19; H, 8.72; N, 6.56; Calculated: C, 72.40; H, 8.72; N, 6.49; Melting point: 156-158° C.

Example 3: 3-(5'-(Benzofuran-2-yl)-[2,2'-bithi-ophen]-5-yl)-1-dodecyl-6-dodecoxynaphthyridine-2-one (NDO-2T-BF) (9)

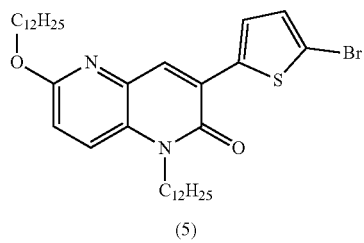 + 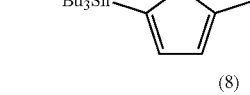

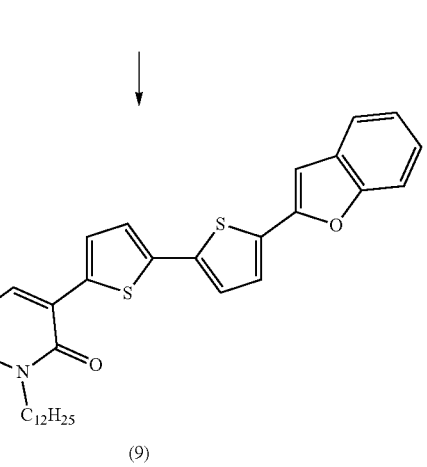

2-(5-Tributylstannylstannylthiophen-2-yl)benzofuran (8)

3-(5'-(Benzofuran-2-yl)-[2,2'-bithiophen]-5-yl)-1-dodecyl-6-dodceoxynaphthyridine-2-one (NDO-2T-BF) (9)

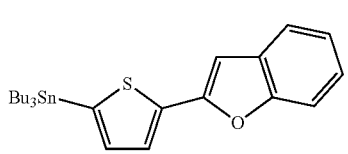

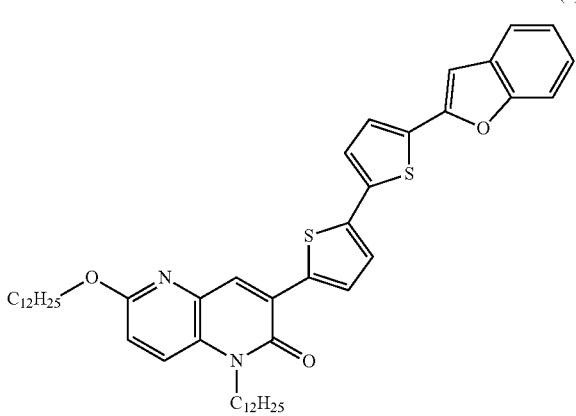

N-butyllithium (0.50 cm³, 1.20 mmol, 2.40 M) is added to a flask containing 2-(thiophene-2-yl)-benzofuran (0.20 g, 1.00 mmol) and diethyl ether (10 cm³) under an inert atmosphere at −78° C. The solution is allowed to stir for 2 hours before the addition of tributyltin chloride at 0° C. The reaction mixture is left to stir at room temperature. The reaction is quenched with water (2 cm³) and washed with brine (3×10 cm³). The organic phase is then dried over MgSO₄ and the solvent is evaporated to give a crude oil which is used without further purification. Yield=0.49 g (100%) 1H NMR (400 MHz, CDCl3) δ 7.60 (d, J=3.4 Hz, 1H), 7.55-7.51 (m, 1H), 7.51-7.46 (m, 1H), 7.23 (m, 2H), 7.15 (d, J=3.4 Hz, 1H), 6.85 (d, J=0.7 Hz, 1H), 1.66-1.55 (m, 6H), 1.42-1.30 (m, 6H), 1.19-1.09 (m, 6H), 0.91 (m, 9H).

3-(5-Bromothiophen-2-yl)-1-dodecyl-6-dodecoxynaph-thyridine-2-one (compound 5) (0.35 g, 0.53 mmol) and 2-(5-tributylstannylstannylthiophen-2-yl)benzofuran (compound 8) (0.313 g, 0.64 mmol) are added to a flask which is purged with nitrogen and evacuated. Anhydrous N,N-dim-ethylformamide (15 cm³) is then added to flask and the mixture is subsequently degassed by bubbling with nitrogen for 45 minutes. Pd(PPh₃)₄ (0.043 g, 0.037 mmol) is added to the flask and the reaction mixture is left to react at reflux for 16 hours. Once cooled, the solution is diluted with diethyl ether (100 cm³) and washed with saturated NaHCO₃ solution (2×60 cm³) and brine (2×60 cm³). The solvent is evaporated to yield the crude product, which is purified by column chromatography (0%→50% dichloromethane: hexane). Yield=0.280 g (68%). 1H NMR (400 MHz, CDCl3) δ 8.22 (s, 1H), 7.72 (d, J=4.0 Hz, 1H), 7.59 (d, J=9.2 Hz, 1H), 7.56-7.51 (m, 1H), 7.51-7.46 (m, 1H), 7.39 (d, J=3.8 Hz, 1H), 7.30-7.20 (m, 4H), 6.92 (d, J=9.1 Hz, 1H), 6.85 (d, J=0.7 Hz, 1H), 4.36 (dt, J=15.8, 7.4 Hz, 4H), 1.87-1.71 (m, 4H), 1.53-1.19 (m, 36H), 0.88 (dd, J=6.9, 6.1 Hz, 6H); 13C NMR (101 MHz, CDCl3) δ 159.9, 159.1, 154.8, 151.1, 140.2, 138.3, 136.3, 135.3, 132.0, 131.6, 130.1, 129.3, 127.7, 126.5, 125.6, 125.2, 124.5, 123.7, 123.3, 120.9, 114.0, 111.2, 101.4, 66.6, 43.8, 32.1, 29.8, 29.8, 29.7, 29.6, 29.53, 29.50, 29.2, 28.2, 27.2, 26.3, 22.8, 14.3; m/z (MALDI): 779.11 [M]+; Elemental analysis: Found: C, 73.79; H, 7.72; N, 3.76; Calculated: C, 73.99; H, 8.02; N, 3.60; Melting point: 98-100° C.

Example 4: 3-(5"-Benzofuran-2-yl)-[2,2':5',2"-terthiophen]-5-yl)-1-dodecyl-6-dodecoxynaphthyridine-2-one (NDO-3T-BF) (12)

3-([2,2'-Bithiophen]-5-yl)-1-dodecyl-6-dodecoxynaphthyridine-2-one (10)

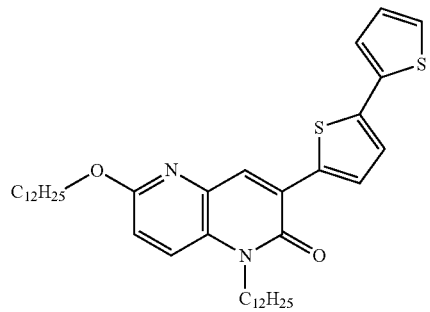

3-Bromo-1-dodecyl-6-dodecoxynaphthyridine-2one (compound 3) (0.50 g, 0.87 mmol) and 5-tributylstannyl-2,2'-bithiophene (0.43 g, 0.95 mmol) are added to a flask which is evacuated and purged with nitrogen. Anhydrous N,N-dimethylformamide (31 cm³) is then added before the solution is degassed by bubbling through nitrogen for 45

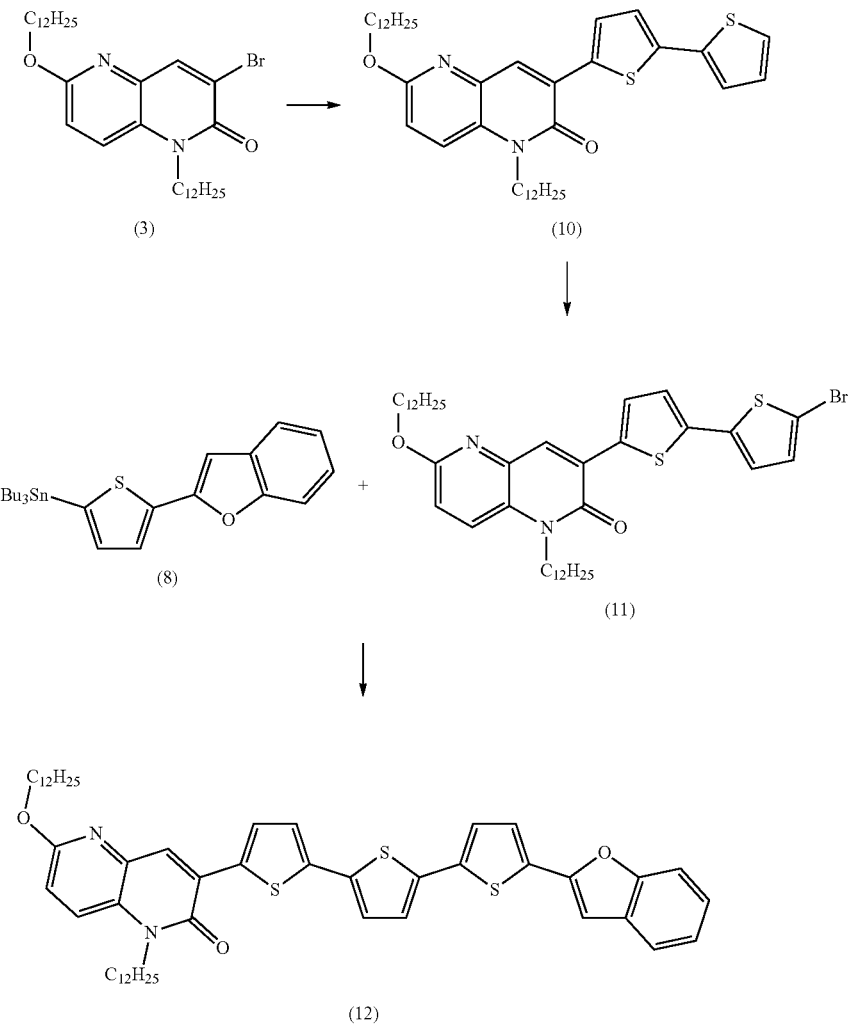

minutes. Pd(PPh3)4 (0.07 g, 0.061 mmol) is then added and the reaction is heated at reflux with stirring for 16 hours. The solution is diluted with diethyl ether (50 cm³) and washed with saturated NaHCO3(aq) solution (2×100 cm³) and brine (2×100 cm³). The organic phase is then dried over MgSO4, the solvent evaporated under reduced pressure and the crude product purified by column chromatography (1:1 dichloromethane:hexane mobile phase) to yield the product. Yield=0.44 g (77%). 1H NMR (400 MHz, CDCl3) δ 8.20 (s, 1H), 7.70 (d, J=3.7 Hz, 1H), 7.59 (d, J=9.1 Hz, 1H), 7.28 (d, J=2.7 Hz, 1H), 7.22 (s, 2H), 7.09-6.97 (m, 1H), 6.92 (d, J=9.0 Hz, 1H), 4.35 (dt, J=14.7, 7.0 Hz, 4H), 1.92-1.66 (m, 4H), 1.54-1.07 (m, 36H), 0.88 (t, J=6.1 Hz, 6H); 13C NMR (101 MHz, CDCl3) δ 159.9, 159.2, 140.8, 137.9, 135.7, 135.4, 131.5, 123.0, 128.1, 128.0, 126.5, 125.2, 124.7, 123.9, 123.4, 113.9, 66.6, 43.7, 32.1, 29.8, 29.77, 29.7, 29.6, 29.54, 29.50, 29.2, 28.2, 26.3, 22.8, 14.3; m/z (MALDI): 663.03 [M]+; Elemental Analysis: Found: C, 72.28; H, 8.78; N, 4.22; Expected: C, 72.46; H, 8.78; N, 4.22; Melting point: 84-86° C.

3-([5-Bromo-2,2'-bithiophene-5'-yl)-1-dodecyl-6-dodecoxynaphthyridine-2-one (11)

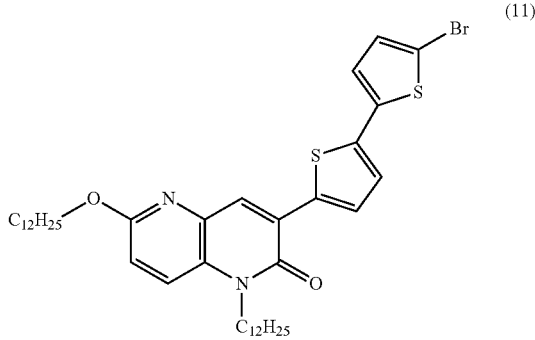

Chloroform (6 cm³) and acetic acid (6 cm³) are added to a flask containing 3-([2,2'-bithiophen]-5-yl)-1-dodecyl-6-dodecoxynaphthyridine-2-one (compound 10) (0.255 g, 0.38 mmol) and N-bromosuccinimide (0.075 g, 0.42 mmol) and the solution is allowed to stir for 16 hours at room temperature in the absence of light. The reaction mixture is diluted with dichloromethane (20 cm³) and washed with 10% w/v KOH(aq) solution (3×30 cm³). The organic phase is dried over MgSO4 before evaporation of the solvent to yield the crude product. The crude product is purified by column chromatography (3:2 dichloromethane:hexane mobile phase). Yield=0.23 g (81%); 1H NMR (400 MHz, CDCl3) δ 8.22 (s, 1H), 7.68 (d, J=4.0 Hz, 1H), 7.61 (d, J=9.2 Hz, 1H), 7.15 (d, J=4.0 Hz, 1H), 7.02 (d, J=3.9 Hz, 1H), 6.97 (dd, J=6.1, 4.4 Hz, 1H), 6.96-6.91 (m, 1H), 4.35 (ddd, J=15.7, 13.4, 6.9 Hz, 4H), 1.86-1.71 (m, 4H), 1.52-1.15 (m, 36H), 0.88 (t, J=6.8 Hz, 6H); 13C NMR (101 MHz, CDCl3) δ 159.9, 159.1, 145.1, 139.7, 139.5, 136.2, 135.3, 131.7, 131.0, 130.1, 127.7, 125.3, 123.9, 123.6, 114.1, 111.2, 66.6, 43.8, 32.1, 29.8, 29.8, 29.7, 29.6, 29.5, 29.19, 29.16, 28.1, 27.2, 26.3, 22.8, 14.3; m/z (MALDI): 741.78 [M]+; Elemental Analysis: Found: C, 64.42; H, 7.56; N, 3.61; Expected: C, 64.76; H, 7.74; N, 3.78; Melting point: 87-89° C.

3-(5"-Benzofuran-2-yl)-[2,2':5',2"-terthiophen]-5-yl)-1-dodecyl-6-dodecoxynaphthyridine-2-one (NDO-3T-BF) (12)

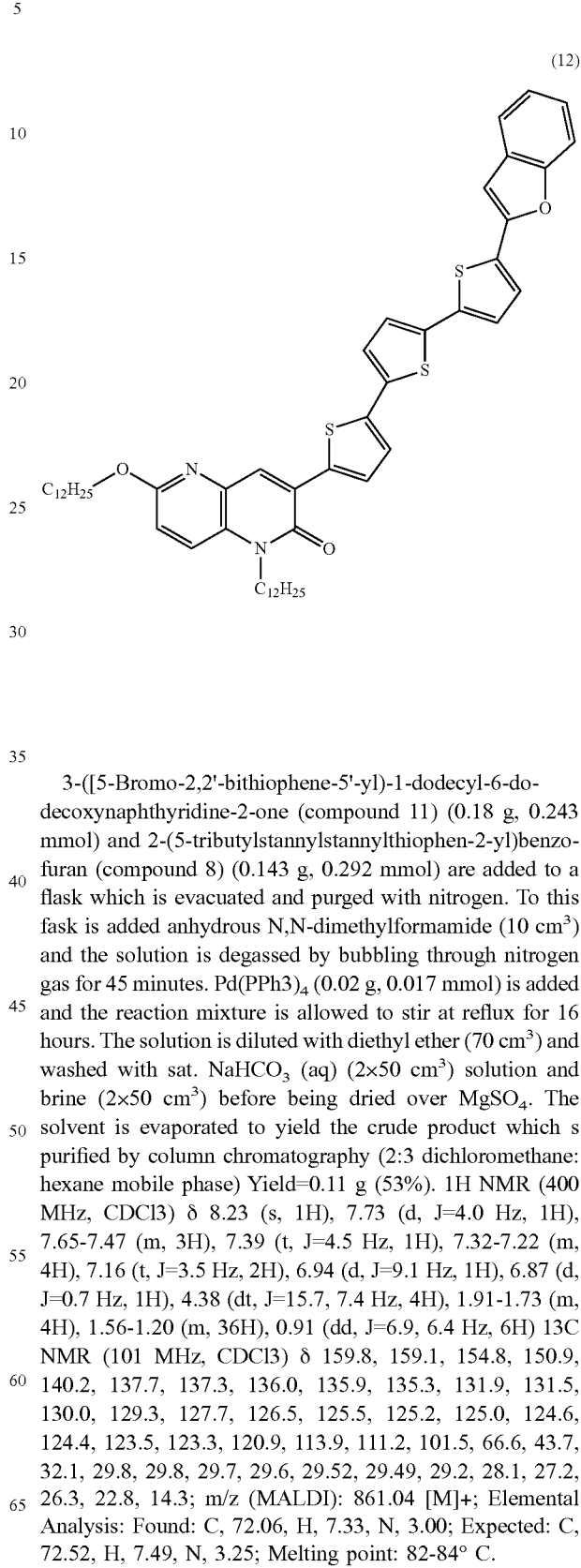

3-([5-Bromo-2,2'-bithiophene-5'-yl)-1-dodecyl-6-dodecoxynaphthyridine-2-one (compound 11) (0.18 g, 0.243 mmol) and 2-(5-tributylstannylstannylthiophen-2-yl)benzofuran (compound 8) (0.143 g, 0.292 mmol) are added to a flask which is evacuated and purged with nitrogen. To this fask is added anhydrous N,N-dimethylformamide (10 cm³) and the solution is degassed by bubbling through nitrogen gas for 45 minutes. Pd(PPh3)4 (0.02 g, 0.017 mmol) is added and the reaction mixture is allowed to stir at reflux for 16 hours. The solution is diluted with diethyl ether (70 cm³) and washed with sat. NaHCO3 (aq) (2×50 cm³) solution and brine (2×50 cm³) before being dried over MgSO4. The solvent is evaporated to yield the crude product which s purified by column chromatography (2:3 dichloromethane:hexane mobile phase) Yield=0.11 g (53%). 1H NMR (400 MHz, CDCl3) δ 8.23 (s, 1H), 7.73 (d, J=4.0 Hz, 1H), 7.65-7.47 (m, 3H), 7.39 (t, J=4.5 Hz, 1H), 7.32-7.22 (m, 4H), 7.16 (t, J=3.5 Hz, 2H), 6.94 (d, J=9.1 Hz, 1H), 6.87 (d, J=0.7 Hz, 1H), 4.38 (dt, J=15.7, 7.4 Hz, 4H), 1.91-1.73 (m, 4H), 1.56-1.20 (m, 36H), 0.91 (dd, J=6.9, 6.4 Hz, 6H) 13C NMR (101 MHz, CDCl3) δ 159.8, 159.1, 154.8, 150.9, 140.2, 137.7, 137.3, 136.0, 135.9, 135.3, 131.9, 131.5, 130.0, 129.3, 127.7, 126.5, 125.5, 125.2, 125.0, 124.6, 124.4, 123.5, 123.3, 120.9, 113.9, 111.2, 101.5, 66.6, 43.7, 32.1, 29.8, 29.8, 29.7, 29.6, 29.52, 29.49, 29.2, 28.1, 27.2, 26.3, 22.8, 14.3; m/z (MALDI): 861.04 [M]+; Elemental Analysis: Found: C, 72.06, H, 7.33, N, 3.00; Expected: C, 72.52, H, 7.49, N, 3.25; Melting point: 82-84° C.

Example 5: 3,3'-(2,2'-Bithiophene-5'-yl)-bis(1-dodecyl-6-dodecoxynaphthyridine-2-one (NDO)2-2T (13)

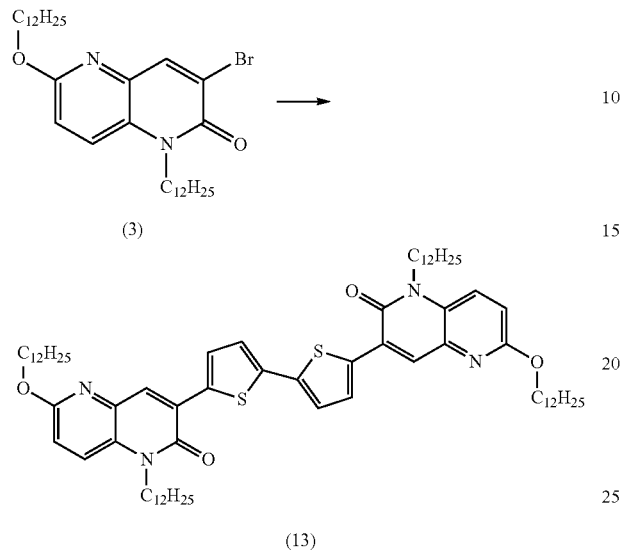

3,3'-(2,2'-Bithiophene-5'-yl)-bis(1-dodecyl-6-dodecoxynaphthyridine-2-one (NDO)2-2T (13)

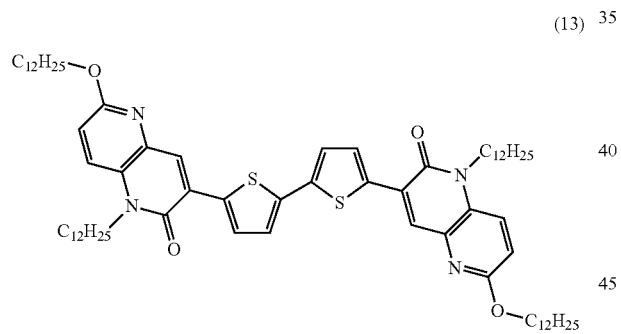

3-Bromo-1-dodecyl-6-dodecoxynaphthyridine-2one (compound 3) (0.20 g, 0.17 mmol) and 5,5'-bis(tributylstannyl)-2,2'-bithiophene (0.065 g, 0.09 mmol) are added to a microwave vial which was purged with nitrogen before the addition of anhydrous N,N-dimethylformamide (5 cm$^3$). The solution is then degassed for 30 minutes by bubbling nitrogen through the mixture, before Pd(PPh$_3$)$_4$ (0.019 g, 0.017 mmol) is added. The reaction is then carried out in a microwave reactor for 2 hours at 160° C. The reaction mixture is diluted in diethyl ether (25 cm$^3$) and washed with brine (3×40 cm$^3$). The organic phase is dried over MgSO$_4$ and the solvent is evaporated. The crude product is then purified by column chromatography (mobile phase: 0%→20% ethyl acetate/hexane) to give a sticky red solid. Yield=0.014 g (14%); 1H NMR (400 MHz, CDCl3) δ 8.23 (s, 2H), 7.75 (d, J=4.0 Hz, 2H), 7.61 (d, J=9.2 Hz, 2H), 7.35 (d, J=4.0 Hz, 2H), 6.93 (d, J=9.1 Hz, 2H), 4.37 (dt, J=15.4, 7.3 Hz, 8H), 1.88-1.72 (m, 8H), 1.52-1.18 (m, 72H), 0.88 (t, J=6.7 Hz, 12H); m/z (MALDI): 1158.67 [M]+.

Example 6: Monomer for Polymerisations; 3,7-Dibromo-1,5-dihexadecyl-1,5-dihydro-[1,5]naphthyridine-2,6-dione (15)

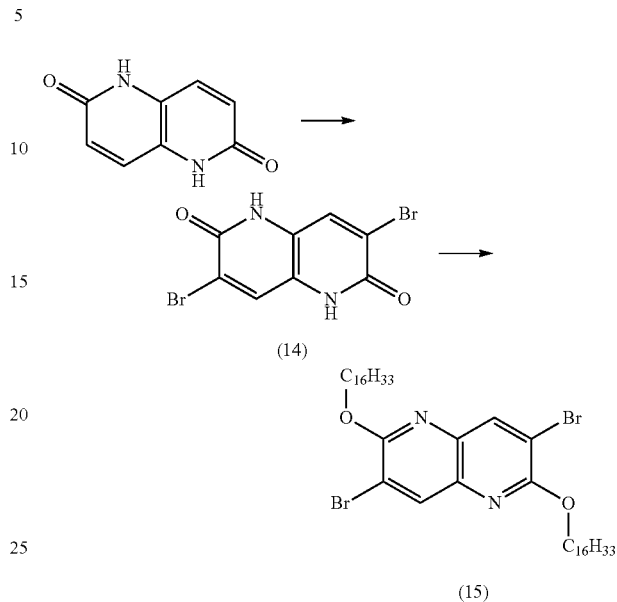

3,7-Dibromo-1,5-dihydro-[1,5]naphthyridine-2,6-dione (14)

To a solution of 1,5-dihydro-[1,5]naphthyridine-2,6-dione (0.10 g, 0.62 mmol) in fuming sulfuric acid (5 cm$^3$) is added slowly a solution of 1,3-dibromo-[1,3,5]triazinane-2,4,6-trione (0.18 g, 0.62 mmol) in fuming sulfuric acid (5 cm$^3$). The mixture is stirred at room temperature for 16 hours and precipitated into methanol (50 cm$^3$). The solids are collected by filtration to yield the product as a brown solid. Yield=0.086 g (44%); 1H NMR (300 MHz, d-trifluoroacetic acid) δ 7.89 (s, 2H).

3,7-Dibromo-1,5-dihexadecyl-1,5-dihydro-[1,5]naphthyridine-2,6-dione (15)

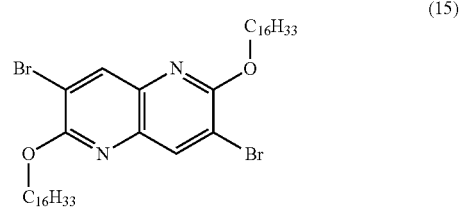

To a round bottom flask is added 3,7-dibromo-1,5-dihydro-[1,5]naphthyridine-2,6-dione (2.0 g, 6.3 mmol), potassium carbonate (2.6 g, 18.8 mmol) and N,N-dimethylformamide (20 cm$^3$). The reaction mixture is stirred at 120° C. for 1 hour before adding 1-bromo-hexadecane (5.7 cm$^3$, 18.8 mmol). The reaction mixture is stirred at 120° C. for 16 hours, then cooled to room temperature and precipitated into methanol. The solids are collected by filtration and purified by column chromatography (mobile phase: dichloromethane) to yield the product as a white solid. Yield=2.0 g (42%); 1H NMR (300 MHz, CDCl3) δ 8.26 (s, 2H), 4.45 (t, J=6.5 Hz, 4H), 1.86 (m, 4H), 1.51 (m, 4H), 1.27 (m, 48H), 0.89 (t, J=6.1 Hz, 6H).

Example 7: Poly-[2,6-(4,8-didodecyl-benzo[1,2-b;4,5-b']dithiophene)-co-2,5-bis-thiophene-co-3,7-(2,6-bis-hexadecyloxy-[1,5]naphthyridine)] (16)

tris(dibenzylideneacetone)dipalladium(0) (6.41 mg, 7.0 μmol). To the vessel is added degassed chlorobenzene (5.5 cm$^3$) and the reaction mixture is degassed further for 30 minutes. The reaction mixture is heated to 130° C. and stirred at this temperature for 1 hour. After completion of the reaction, the reaction mixture is allowed to cool to 50° C. and precipitated into stirred methanol (100 cm$^3$). The polymer is collected by filtration and washed with methanol (2×10 cm$^3$) to give a solid. The polymer is sequentially extracted by Soxhlet extraction with acetone, petroleum ether (40-60° C.), cyclohexane and chloroform. The chloroform fraction is concentrated in vacuo to 25 cm$^3$, precipitated by addition to stirred methanol (100 cm$^3$) and collected by filtration to give a red solid (579 mg, 91%).

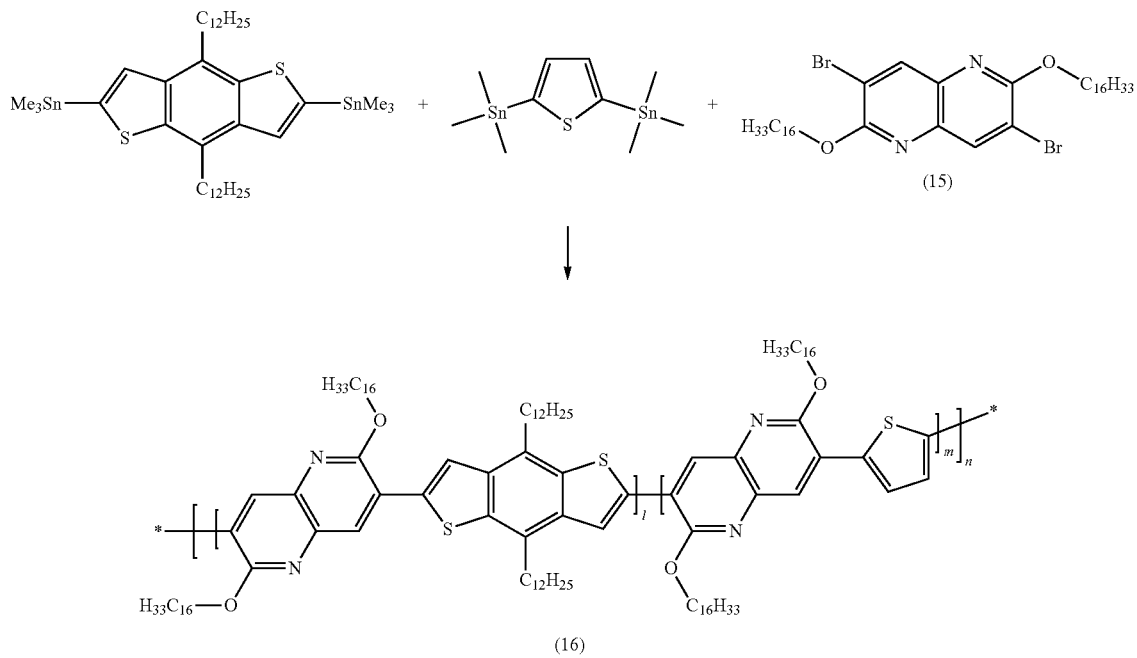

(16)

To a round bottomed flask is added 4,8-didodecyl-2,6-bis-trimethylstannanyl-benzo[1,2-b;4,5-b']dithiophene (298.5 mg, 0.35 mmol), 3,7-dibromo-2,6-bis-hexadecyloxy-[1,5]naphthyridine (compound 15) (538.4 mg, 0.70 mmol), 2,5-bis-trimethylstannanyl-thiophene (143.5 mg, 0.35 mmol), tri-o-tolyl-phosphine (8.53 mg, 28.0 μmol) and GPC (50° C., chlorobenzene) Mn=123.9 kg mol-1; Mw=455.8 kg mol-1; PDI=3.68.

Example 8: Poly-[5,5'-(2,2'-bithiophene)-co-3,7-(2,6-bis-hexadecyloxy-[1,5]naphthyridine)] (17)

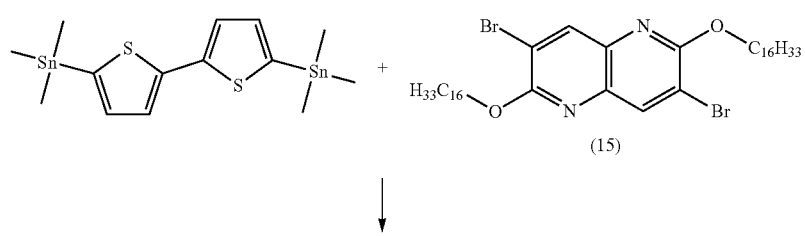

-continued

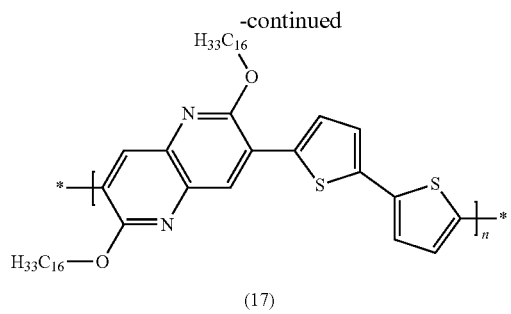

(17)

To a round bottomed flask is added 3,7-dibromo-2,6-bis-hexadecyloxy-[1,5]naphthyridine (compound 15) (300.0 mg, 0.390 mmol), 5,5'-bis-trimethylstannanyl-[2,2']bithiophenyl (191.9 mg, 0.390 mmol), tri-o-tolyl-phosphine (9.50 mg, 31.0 μmol) and tris(dibenzylideneacetone)dipalladium(0) (5.49 mg, 8.0 μmol). To the vessel is added degassed toluene (12.5 cm$^3$) and N,N-dimethylformamide (2.5 cm$^3$) and the reaction mixture is degassed further for 1 hour. The reaction mixture is heated to 100° C. and stirred at this temperature for 2 hours. Bromobenzene (0.08 cm$^3$, 0.780 mmol) is then added followed by an additional 10 minutes heating at 100° C. Next, tributyl-phenyl-stannane (0.38 cm$^3$, 1.171 mmol) is added followed by an additional 20 minutes heating at 100° C. After completion of the reaction, the reaction mixture is allowed to cool to 50° C. and precipitated into stirred methanol (100 cm$^3$). The polymer is collected by filtration and washed with methanol (50 cm$^3$) to give a solid. The polymer is sequentially extracted by Soxhlet extraction with acetone, petroleum ether (40-60° C.), cyclohexane, chloroform and chlorobenzene. The chloroform and chlorobenzene fractions are concentrated in vacuo to 25 cm$^3$, precipitated by addition to stirred methanol (100 cm$^3$) and collected by filtration to give black solids, chloroform fraction (130 mg, 43%), chlorobenzene fraction (80 mg, 27%).

Chloroform fraction; GPC (120° C., 1,2,4-trichlorobenzene) Mn=87.8 kg mol-1; Mw=160.6 kg mol-1; PDI=1.83.

Chlorobenzene fraction; GPC (120° C., 1,2,4-trichlorobenzene) Mn=71.6 kg mol-1; Mw=159.0 kg mol-1; PDI=2.23.

Use Example A

Fabrication of OFET Devices with Compound 7

Organic field-effect transistors (OFETs) are fabricated on SiO$_2$ substrates with prefabricated interdigitated Au source-drain channels with lengths of 2.5, 5, 10 and 20 μm, and a width of 1 cm. N-doped Si and SiO$_2$ are used as the gate electrode and gate dielectric respectively. The substrates are cleaned using water, acetone and ethanol before being treated in UV-ozone for 30 seconds. The pentafluorobenzenethiol (PFBT) self-assembled monolayer (SAM) is prepared by dropcasting a solution of PFBT (10 mM in ethanol) onto the substrate. After 1 minute, the residual PFBT is washed with ethanol and the substrate is dried over a stream of compressed air. Similarly, octadecyltrichlorosilane (OTS) SAM is prepared by dropcasting an OTS solution (13 mM in toluene) onto the substrate which is washed with toluene and dried after 1 minute.

Hexamethyldisilazane (HDMS) SAM is added by spin-coating onto the prefabricated OFET substrate at 2000 rpm before annealing at 150° C. for 20 minutes. Solutions of Compound 7 (10 mg ml$^{-1}$) are spin-coated onto the OFET substrate at 2000 rpm and the substrates are annealed for 20 minutes at 120° C. Current-voltage characteristics are recorded using a Keithley 4200 semiconductor parameter analyser at room temperature in a nitrogen atmosphere. The field-effect mobilities were calculated from the saturation regime ($V_d$>($V_g$-$V_0$)) using equation (1):

$$\left(\frac{dI_d^{sat}}{dV_g}\right)_{V_d} = \frac{WC_i}{L}\mu^{sat}(V_g - V_0) \tag{1}$$

where W is the channel width, L the channel length, $C_i$ the capacitance of insulating layer, $V_g$ the gate voltage, $V_0$ the turn-on voltage, and μsat is the charge carrier mobility in the saturation regime. Turn-on voltage ($V_0$) was determined as the onset of source-drain current.

Figure 1B:
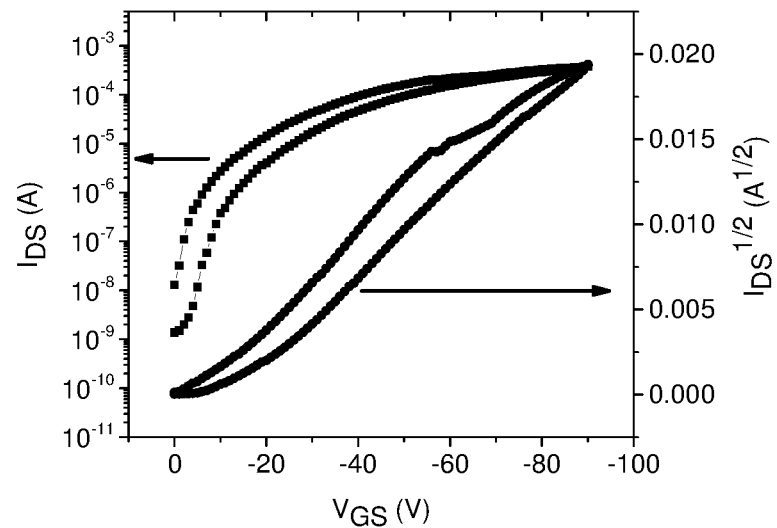
FIG. 1b shows the transfer graph of an OFET prepared according to Use Example A.

FIG. 1a shows the output graph of a OFET device with compound 7, and FIG. 1b shows the transfer graph of the OFET device.

The mobility and on/off ratio values are summarized in Table 1 below.

TABLE 1

| Self-assembled Monolayer | Annealing temperature (° C.) | $\mu_h$ (cm$^2$ V$^{-1}$ s$^{-1}$) average | ON/OFF ratio |
| --- | --- | --- | --- |
| PFBT | 25 | 3.6 × 10$^{-3}$ | 10$^4$ |
| PFBT/OTS | 25 | 2.3 × 10$^{-3}$ | 10$^4$ |
| OTS | 25 | 0.014 | 10$^4$ |
| HMDS | 25 | 5.5 × 10$^{-3}$ | 10$^3$ |
| PFBT | 120 | 4.6 × 10$^{-3}$ | 10$^5$ |
| PFBT/OTS | 120 | 4.7 × 10$^{-3}$ | 10$^4$ |
| OTS | 120 | 0.022 | 10$^4$ |
| HMDS | 120 | 3.9 × 10$^{-3}$ | 10$^4$ |

The results herein show that OFETs fabricated using compound 7 with an OTS SAM and subsequent annealing at 120° C. are able to yield mobilites reaching an average of 0.022 cm$^2$ V$^{-1}$ s$^{-1}$, with an on/off ratio of 10$^4$. This result demonstrates the applicability of small molecules containing the 2,6-disubstituted-[1,5]naphthyridine core for use in OFETs.

Use Example B

Fabrication of OFET Devices with Polymer 17

Top-gate thin-film OFETs were fabricated on glass substrates with photolithographically defined Au source-drain electrodes. A 7 mg/cm$^3$ solution of the organic semiconductor in dichlorobenzene was spin-coated on top (an optional annealing of the film is carried out at 100° C., 150° C. or 200° C. for between 1 and 5 minutes) followed by a spin-coated fluoropolymer dielectric material (Lisicon®

D139 from Merck, Germany). Finally a photolithographically defined Au gate electrode was deposited. The electrical characterization of the transistor devices was carried out in ambient air atmosphere using computer controlled Agilent 4155C Semiconductor Parameter Analyser. Charge carrier mobility in the saturation regime (μsat) was calculated for the compound. Field-effect mobility was calculated in the saturation regime $(V_d>(V_g-V_0))$ using equation (1):

$$\left(\frac{dI_d^{sat}}{dV_g}\right)_{V_d} = \frac{WC_i}{L}\mu^{sat}(V_g - V_0) \tag{1}$$

where W is the channel width, L the channel length, $C_i$ the capacitance of insulating layer, $V_g$ the gate voltage, $V_0$ the turn-on voltage, and μsat is the charge carrier mobility in the saturation regime. Turn-on voltage $(V_0)$ was determined as the onset of source-drain current.

Figure 2:
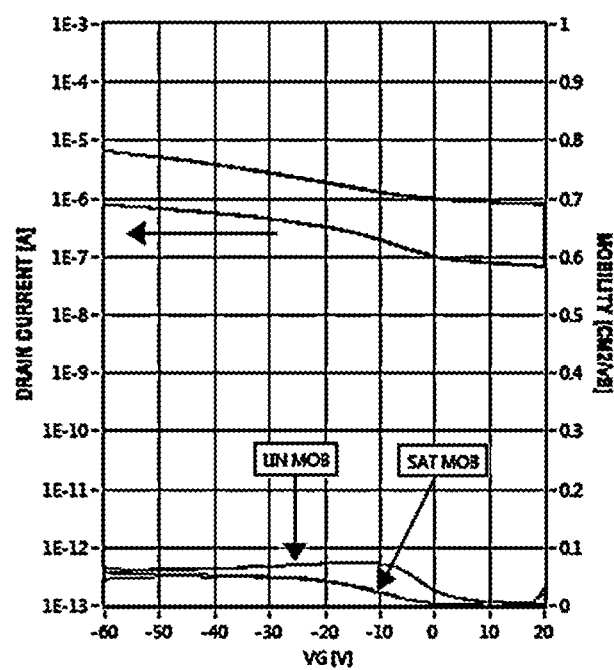
FIG. 2 shows the transfer characteristics and the charge carrier mobility of a top-gate OFET prepared according to Use Example B.

FIG. 2 shows the transfer characteristics and the charge carrier mobility of a top-gate OFET device with polymer 17.

The mobility ($\mu_{sat}$) for polymer 17 in top-gate OFETs is 0.063 cm$^2$ V$^{-1}$ s$^{-1}$.

This result demonstrates that OFETs fabricated using polymer 17 are able to yield mobilites reaching 0.063 cm$^2$ V$^{-1}$ s$^{-1}$, this result demonstrates the applicability of polymers containing the 2,6-disubstituted-[1,5]naphthyridine core for use in OFETs.

The invention claimed is:

1. A compound comprising one or more divalent units of formula I1 or I2

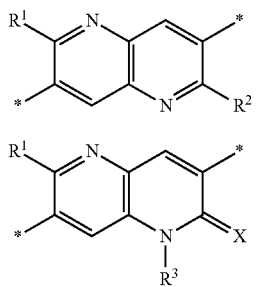

wherein
X is each independently O or S,
R$^1$, R$^2$, R$^3$ are each independently selected from the group consisting of alkyl, alkoxy, thioalkyl, alkylcarbonyl, alkylcarbonyloxy, alkyloxycarbonyl and alkoxycarbonyloxy with 2 to 20 C atoms, each of which is straight-chain or branched and is unsubstituted or substituted by one or more F atoms,
L is each independently F, Cl, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 20 C atoms that is optionally substituted and optionally comprises one or more hetero atoms,
Y$^1$, Y$^2$ are each independently H, F, Cl or CN,
X$^0$ is each independently halogen,
R$^0$, R$^{00}$ are each independently H or alkyl with 1 to 12 C atoms, wherein the compound is a conjugated polymer, which comprises one or more repeating units of formula III or II2, and optionally one or more repeating units of formula II3:

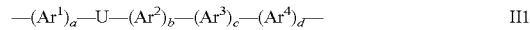 III

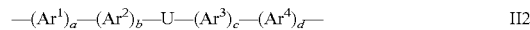 II2

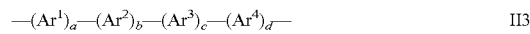 II3 wherein
U is each independently a unit of formula I1 or I2,
Ar$^{1-4}$ are each independently arylene or heteroarylene that is different from U, has 5 to 30 ring atoms, and is optionally substituted by one or more groups L,
a, b, c, d are each independently 0 or 1, wherein in formula II3 a+b+c+d≥1,
or wherein the compound is of formula VI1 or VI2

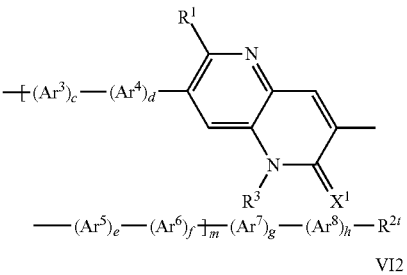 VI1

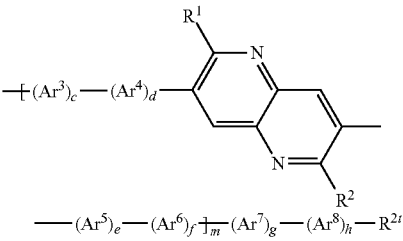 VI2 wherein
Ar$^{1-8}$ are each independently arylene or heteroarylene that is different from U, has 5 to 30 ring atoms, and is optionally substituted by one or more groups L, —CY$^1$=CY$^2$—, —C≡C—, or a unit of formula I1 or I2,
R$^{1t, 2t}$ independently of each other denote F, Cl, Br, —CN, —CF$_3$, —CF$_2$—R, —O—R, —S—R, —SO$_2$—R, —SO$_3$—R, —C(O)—R, —C(S)—R, —C(O)—CF$_2$—R, —C(O)—OR, —C(S)—OR, —O—C(O)—R, —O—C(S)—R, —C(O)—SR, —S—C(O)—R, —C(O)NRR', —NR'—C(O)—R, —NHR, —NRR', —CR'=CR"R'", —C≡C—R', —C≡C—SiR'R"R'", —SiR'R"R'", —CH=C(CN)—C(O)—OR, —CH=C(COOR)$_2$, CH=C(CONRR')$_2$, CH=C(CN)(Ar$^9$),

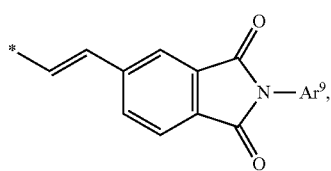

Ar$^{9,10}$ are each independently aryl or heteroaryl, each having from 4 to 30 ring atoms, optionally containing fused rings and being unsubstituted or substituted with one or more groups L, R is each independently alkyl with 1 to 20 C atoms which is straight-chain, branched or cyclic, and is unsubstituted, substituted with one or more F or Cl atoms or CN groups, or perfluorinated, and in which one or more C atoms are optionally replaced by —O—, —S—, —C(O)—, —C(S)—, —SiR$^{o}$R$^{oo}$—, —NR$^{o}$R$^{oo}$—, —CHR$^{o}$=CR$^{oo}$— or —C≡C— such that O- and/or S-atoms are not directly linked to each other, R', R", R''' are each independently H or one of the meanings of R, a-h are each independently 0 or 1, with at least one of a-h being 1, m is each independently 1, 2 or 3.

2. The compound according to claim 1, wherein X in the units of formula I2 is O.

3. The compound according to claim 1, wherein R$^3$ in the units of formula I1 and I2 denotes H or is selected from the group consisting of alkyl, alkoxy and thioalkyl with 1 to 20, C atoms, each of which is straight-chain, branched or cyclic and is unsubstituted or substituted by one or more F atoms.

4. The compound according to claim 1, which is a conjugated polymer comprising one or more units of formula I1 or I2 as defined in claim 1.

5. The conjugated polymer according to claim 1, which is selected of formula III:

$$*-[(A)_x-(B)_y]_n-*$$  III wherein
A is a unit of formula II1 or II2,
B is a unit of formula II1, II2 or II3,
x is >0 and ≤1,
y is ≥0 and <1,
x+y is 1, and
n is an integer >1.

6. The conjugated polymer according to claim 4, which is selected from the following formulae -continued

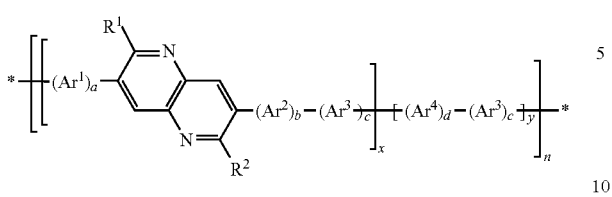
(III8)

A$^{1-4}$ is arylene or heteroarylene that is not of formula I1 or I2, has 5 to 30 ring atoms, and is optionally substituted by one or more groups L, a, b, c and d are 0 or 1, x is >0 and ≤1, y is ≥0 and <1, x+y is 1, and n is an integer >1.

7. The conjugated polymer according to claim 5, which is of formula IV $$R^5\text{-chain-}R^6 \qquad \text{IV}$$

wherein "chain" denotes a polymer chain of formulae III, R$^5$ and R$^6$ have independently of each other one of the meanings of L, or denote, independently of each other, H, F, Br, Cl, I, —CH$_2$Cl, —CHO, —CR'═CR"$_2$, —SiR'R"R'", —SiR'X'X", —SiR'R"X', —SnR'R"R'", —BR'R", —B(OR')(OR"), —B(OH)$_2$, —O—SO$_2$—R', —C≡CH, —C≡C—SiR'$_3$, —ZnX' or an endcap group, X' and X" denote halogen, R', R" and R'" have independently of each other one of the meanings of R$^0$, and two of R', R" and R'" may also form a cyclosilyl, cyclostannyl, cycloborane or cycloboronate group with 2 to 20 C atoms together with the respective hetero atom to which they are attached.

8. The conjugated polymer according to claim 1, wherein one or more of Ar$^1$, Ar$^2$, Ar$^3$ and Ar$^4$ denote arylene or heteroarylene selected from the group consisting of the following formulae

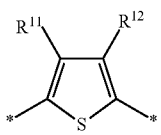
(D1)

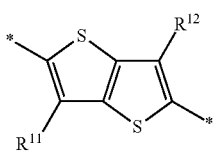
(D10)

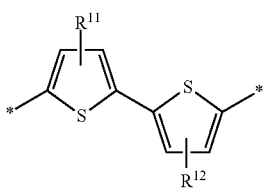
(D19)

-continued

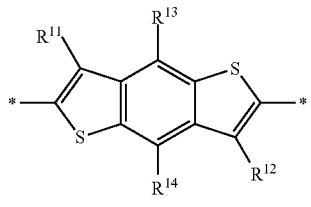
(D22)

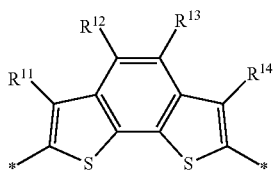
(D30)

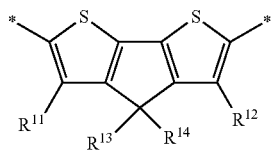
(D35)

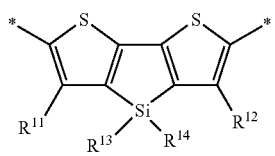
(D36)

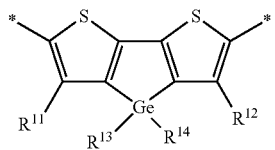
(D37)

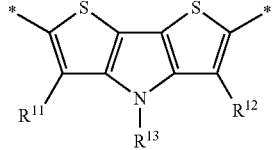
(D38)

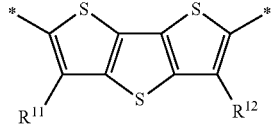
(D42)

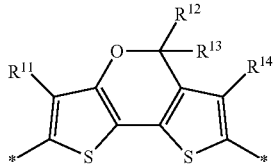
(D44)

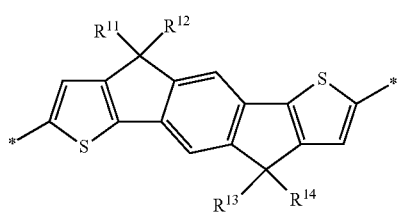
(D55)

(D84) 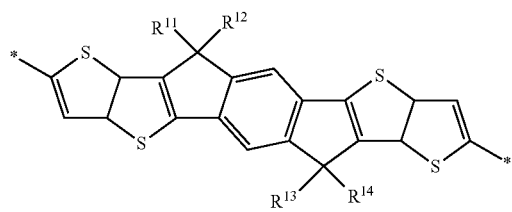
(D93) 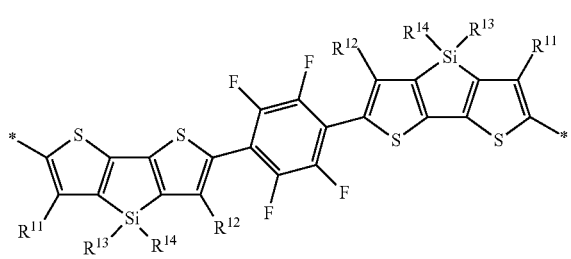
(D94) 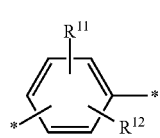
(D103) 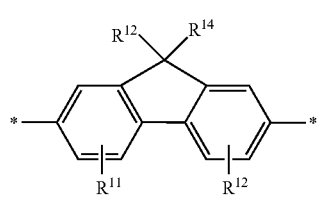
(D108) 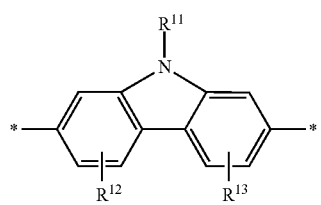
(D111) 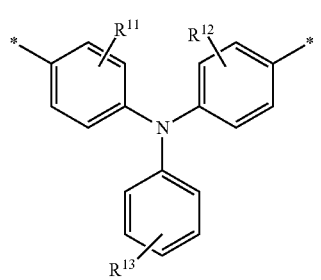
(D137) 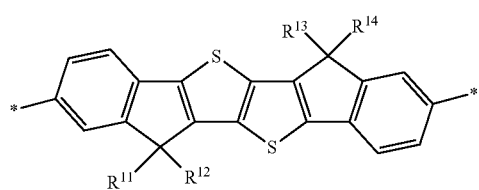
(D139) 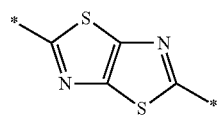
(D140) 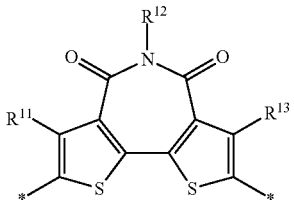
(D141) 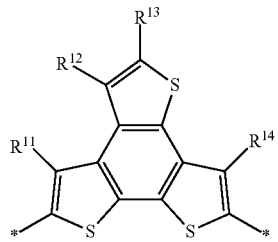
wherein $R^{11}$, $R^{12}$, $R^{13}$, $R^{14}$ independently of each other denote H or have one of the meanings of L.
9. The conjugated polymer according to claim 1, wherein one or more of $Ar^1$, $Ar^2$, $Ar^3$ and $Ar^4$ denote arylene or heteroarylene selected from the group consisting of the following formulae
(A1) 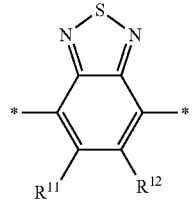
(A2) 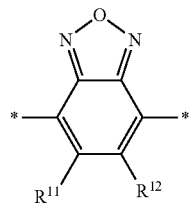
(A3) 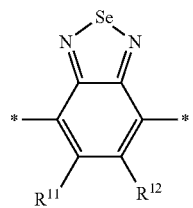

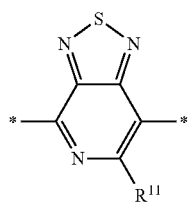 (A7)
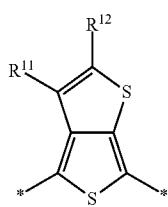 (A15)
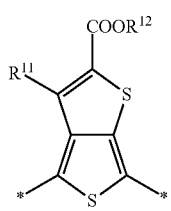 (A16)
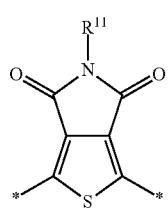 (A20)
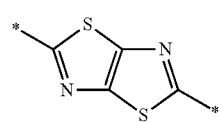 (A41)
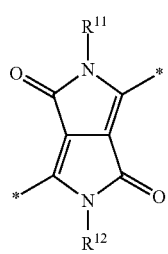 (A48)
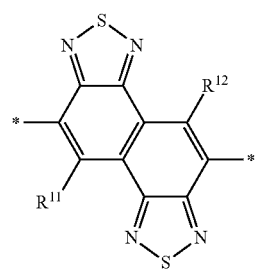 (A74)
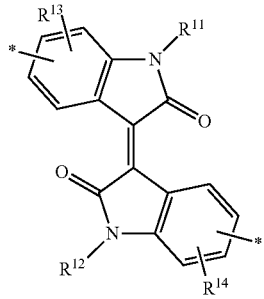 (A84)
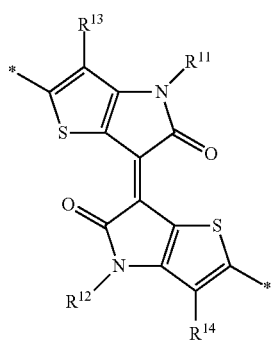 (A85)
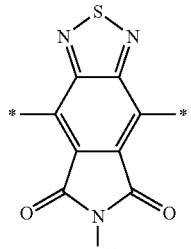 (A88)
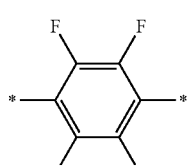 (A94)
wherein $R^{11}$, $R^{12}$, $R^{13}$, $R^{14}$ independently of each other denote H or have one of the meanings of L.
10. The conjugated polymer according to claim 1, wherein one or more of $Ar^1$, $Ar^2$, $Ar^3$ and $Ar^4$ denote arylene or heteroarylene selected from the group consisting of the following formulae
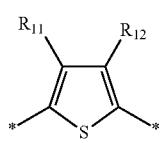 Sp1
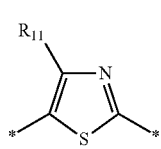 Sp2

-continued

Sp3 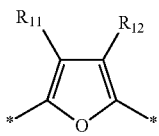

Sp4 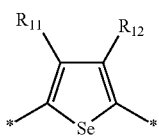

Sp5 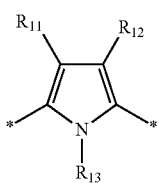

Sp6 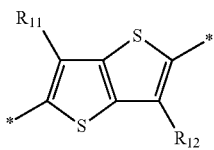

Sp7 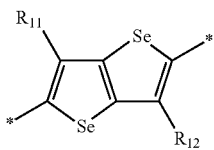

Sp8 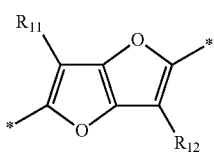

Sp9 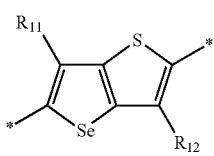

Sp10 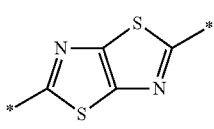

Sp11 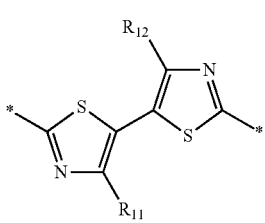

Sp12 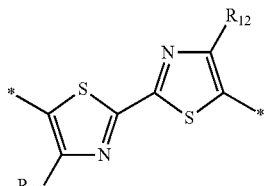

Sp13 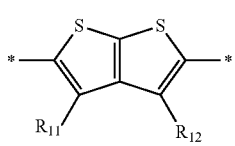

Sp14 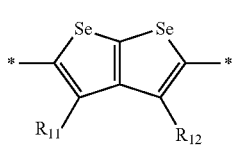

Sp15 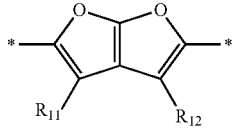

Sp16 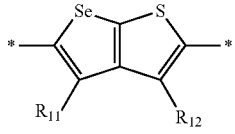

wherein $R^{11-13}$ independently of each other denote H or have one of the meanings of L.

11. The compound according to claim 1, which is selected from formula V1 or V2

$$R^7\text{—}(Ar^1)_a\text{—}U\text{—}(Ar^2)_b\text{—}(Ar^3)_c\text{—}(Ar^4)_d\text{—}R^8 \quad\quad V1$$

$$R^7\text{—}(Ar^1)_a\text{—}(Ar^2)_b\text{—}U\text{—}(Ar^3)_c\text{—}(Ar^4)_d\text{—}R^8 \quad\quad V2$$

wherein

U is a unit of formula I1 or I2, $Ar^{1-4}$ are each independently arylene or heteroarylene that is different from U, has 5 to 30 ring atoms, and is optionally substituted by one or more groups L, a, b, c and d are 0 or 1, and $R^7$ and $R^8$ are each independently an activated C—H bond, Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, Z$^{1-4}$ are selected from the group consisting of C$_{1-10}$ alkyl and C$_{6-12}$ aryl, each being optionally substituted, and two groups Z$^2$ may also form a cycloboronate group having 2 to 20 C atoms together with the B- and O-atoms.

12. The compound according to claim 1 of the following formulae $$R^7\text{—}Ar^1\text{—}U\text{—}Ar^2\text{—}R^8 \quad\quad V1a$$

$$R^7\text{—}U\text{—}R^8 \quad\quad V1b$$

R⁷—Ar¹—U—R⁸  V1c

R⁷—U—Ar²—R⁸  V1d

U is a unit of formula I1 or I2,
Ar¹⁻² is arylene or heteroarylene that is different from U, has 5 to 30 ring atoms, and is optionally substituted by one or more groups L,
R⁷ and R⁸ are each independently an activated C—H bond, Cl, Br, I, O-tosylate, O-triflate, O-mesylate, O-nonaflate, —SiMe₂F, —SiMeF₂, —O—SO₂Z¹, —B(OZ²)₂, —CZ³=C(Z³)₂, —C≡CH, —C≡CSi(Z¹)₃, —ZnX⁰ and —Sn(Z⁴)₃, wherein X⁰ is halogen, Z¹⁻⁴ are C₁₋₁₀ alkyl or C₆₋₁₂ aryl, each being optionally substituted, and two groups Z² may also form a cycloboronate group having 2 to 20 C atoms together with the B- and O-atoms.

13. The compound according to claim 1, wherein
a) one or more of Ar¹, Ar², Ar³ and Ar⁴ denote arylene or heteroarylene, selected from the group consisting of the formulae D1, D10, D19, D22, D30, D35, D36, D37, D38, D42, D44, D55, D84, D93, D94, D103, D108, D111, D137, D139, D140 and D141

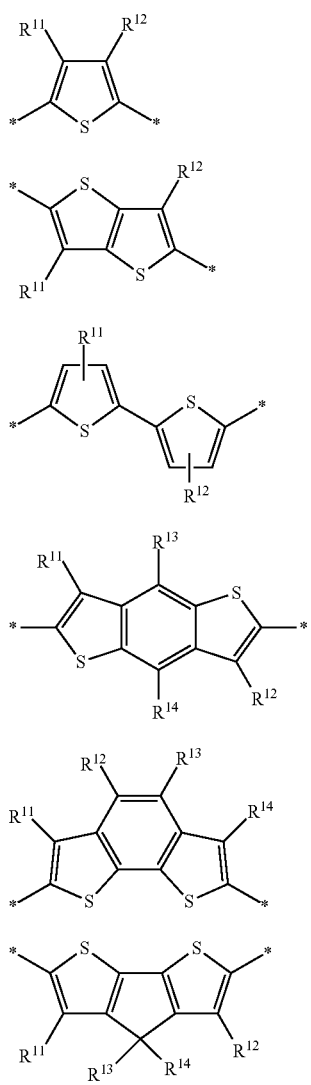

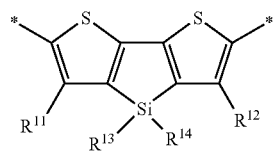

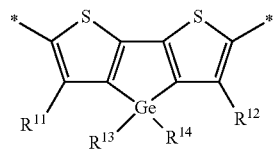

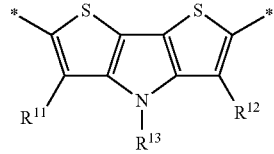

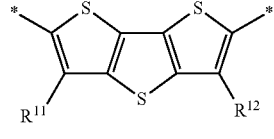

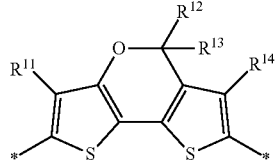

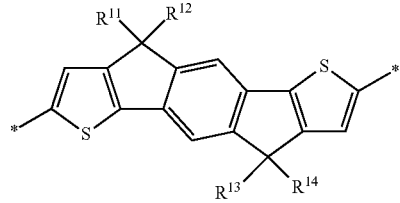

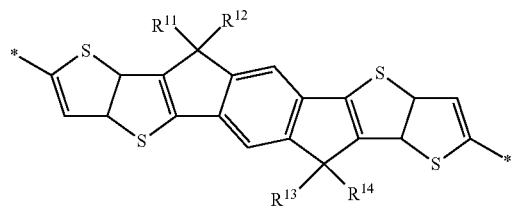

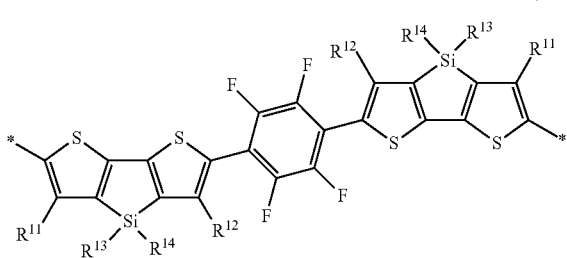

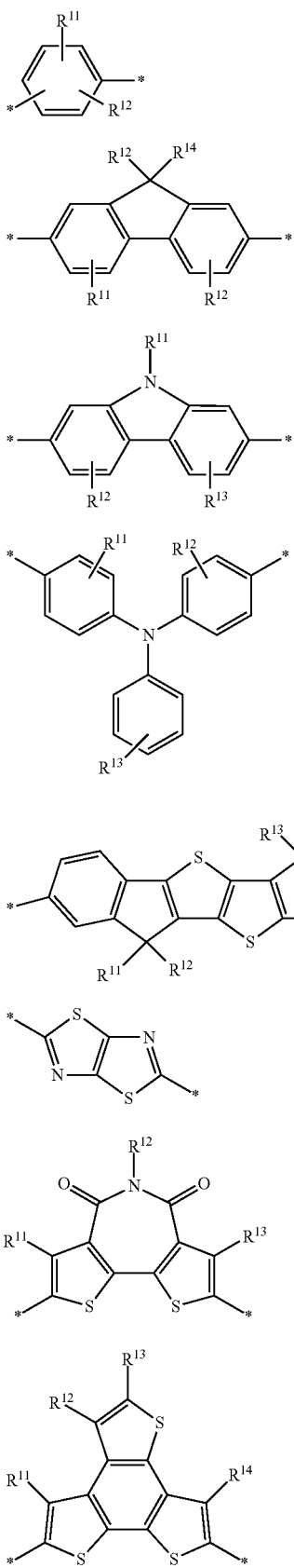

wherein $R^{11-14}$ are each independently H or L, b) one or more of $Ar^1$, $Ar^2$, $Ar^3$ and $Ar^4$ denote arylene or heteroarylene selected from the group consisting of the formulae Sp1, Sp6 and Sp10

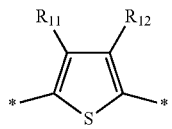

Sp1

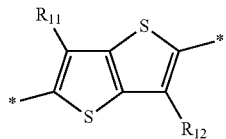

Sp6

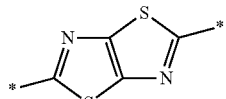

Sp10 and $R^{11}$ and $R^{12}$ are each independently H or L.

14. The compound of claim 1, wherein $Ar^{1-10}$ are selected from the following groups a) the group consisting of the formulae D1, D10, D19, D22, D30, D35, D36, D37, D38, D42, D44, D55, D84, D93, D94, D103, D108, D111, D137, D139, D140 and D141,

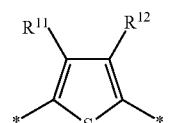

(D1)

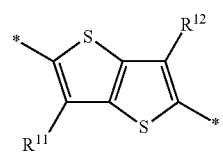

(D10)

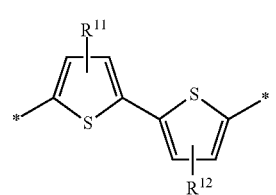

(D19)

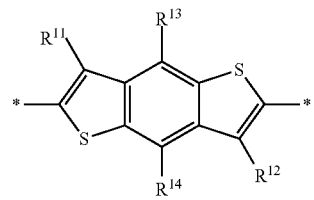

(D22)

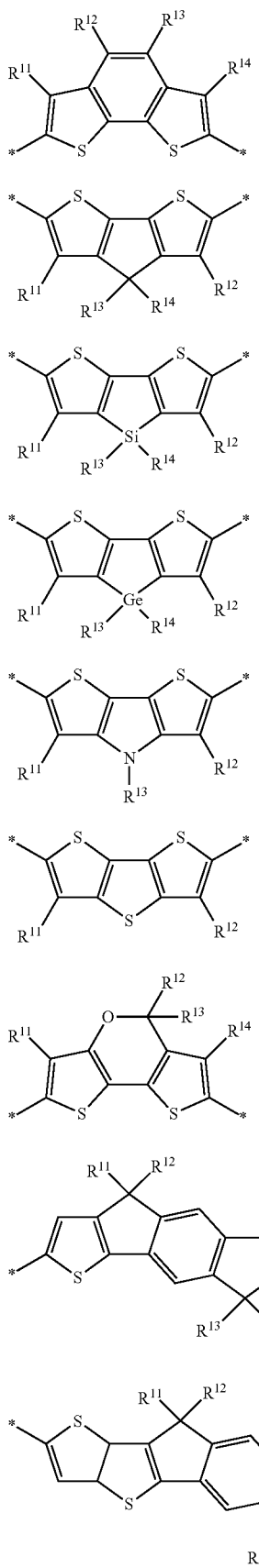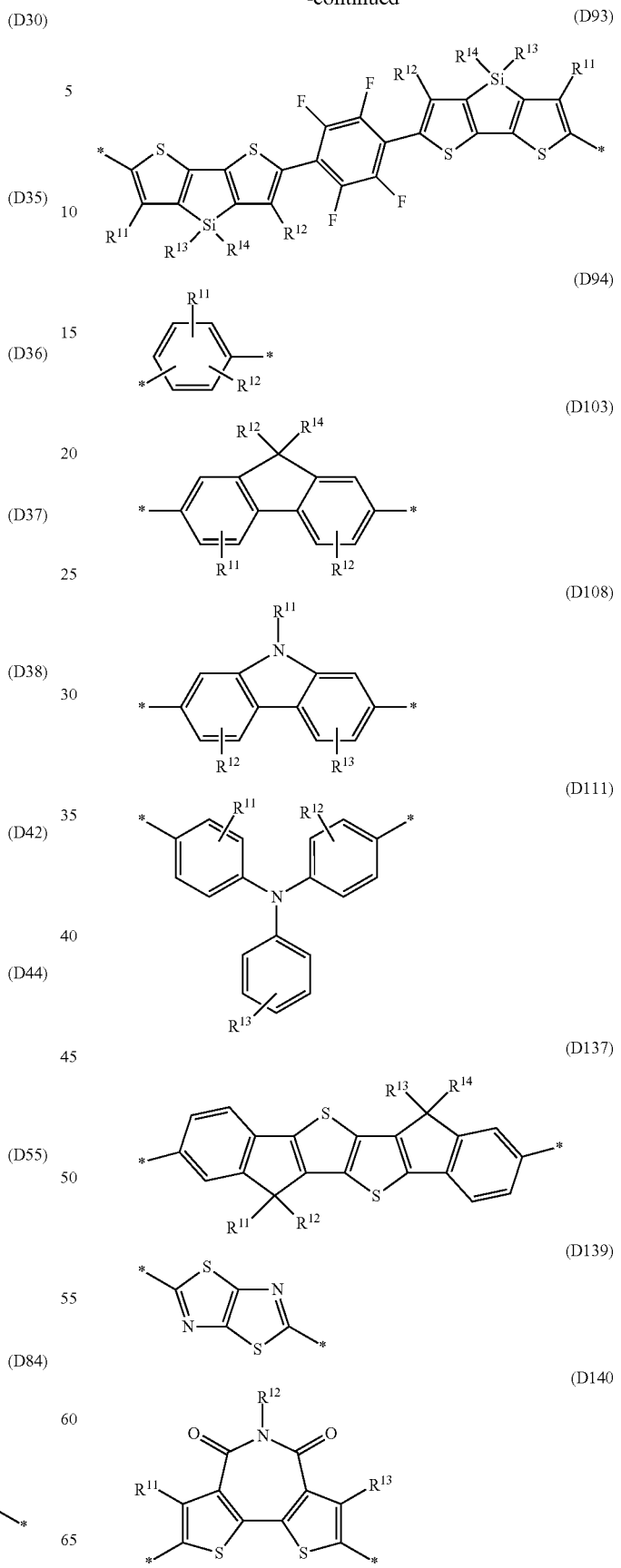

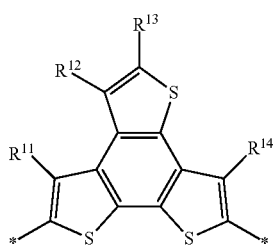
(D141)
wherein $R^{11-14}$ are each independently H or L,
b) the group consisting of the formulae A1, A2, A3, A7, A15, A16, A20, A41, A48, A74, A84, A85, A88 and A94,
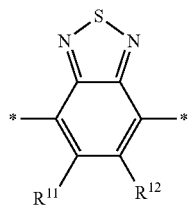
(A1)
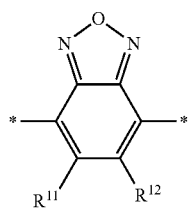
(A2)
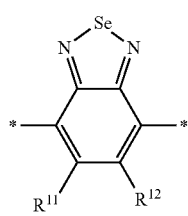
(A3)
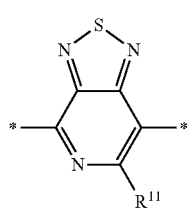
(A7)
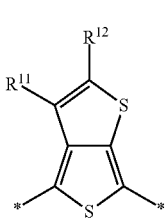
(A15)
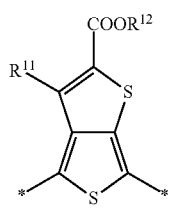
(A16)
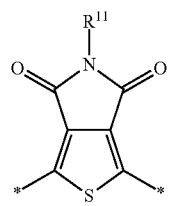
(A20)
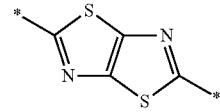
(A41)
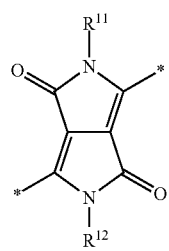
(A48)
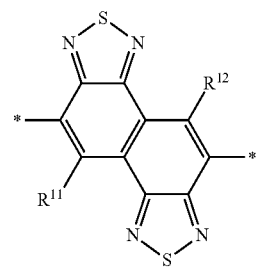
(A74)
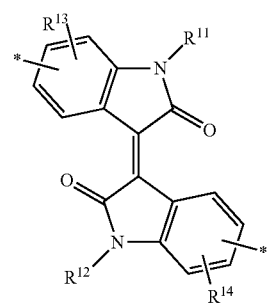
(A84)

-continued (A85)

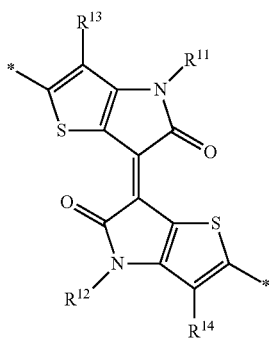

(A88)

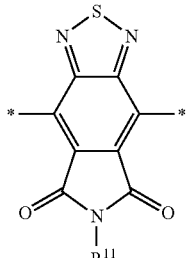

(A94)

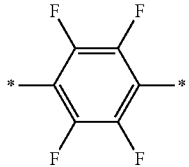

wherein $R^{11-14}$ are each independently H or L,
c) the group consisting of the formulae Sp1, Sp6 and Sp10

Sp1

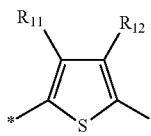

Sp6

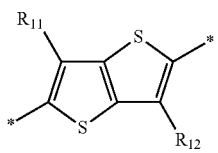

Sp10

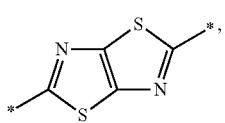

and $R^{11-12}$ are each independently H or L.

15. A mixture comprising one or more compounds according to claim 1 and one or more additional compounds having one or more of semiconducting, charge transport, hole or electron transport, hole or electron blocking, electrically conducting, photoconducting or light emitting properties.

16. A mixture comprising one or more compounds according to claim 1 and one or more n-type organic semiconductors.

17. The mixture of claim 16, wherein the n-type organic semiconductors are selected from fullerenes or substituted fullerenes.

18. A formulation comprising one or more compounds or mixtures according to claim 1, and further comprising one or more solvents selected from organic solvents.

19. An optical, electrooptical, electronic, electroluminescent or photoluminescent device, or a component thereof, or an assembly comprising it, which is prepared using a formulation according to claim 18.

20. A semiconducting, charge transport, electrically conducting, photoconducting or light emitting material comprising a compound or mixture according to claim 1.

21. An optical, electrooptical, electronic, electroluminescent or photoluminescent device, or a component thereof, or an assembly comprising it, which comprises a compound according to claim 1.

22. The optical, electrooptical, electronic, electroluminescent or photoluminescent device of claim 21, which is selected from organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye-sensitized solar cells (DSSC), perovskite-based solar cells, laser diodes, Schottky diodes, photoconductors and photodetectors.

23. The device of claim 21, which is selected from charge injection layers, charge transport layers, interlayers, planarising layers, antistatic films, polymer electrolyte membranes (PEM), conducting substrates and conducting patterns.

24. The device of claim 21, which is selected from integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

25. A bulk heterojunction which comprises, or is being formed from, a mixture according to claim 15.

26. A bulk heterojunction (BHJ) OPV device or inverted BHJ OPV device, comprising a bulk heterojunction of claim 25.

27. A process of preparing a conjugated polymer according to claim 4, by coupling one or more monomers of $$R^7—(Ar^1)_a—U—(Ar^2)_b—(Ar^3)_c—(Ar^4)_d—R^8 \quad \text{V1}$$

$$R^7—(Ar^1)_a—(Ar^2)_b—U—(Ar^3)_c—(Ar^4)_d—R^8 \quad \text{V2}$$

with each other and/or with one or more monomers of formulae MI-MIV in an aryl-aryl coupling reaction $$R^7—Ar^1—R^8 \quad \text{MI}$$

$$R^7—Ar^1—R^8 \quad \text{MII}$$

$$R^7—Ar^a—R^8 \quad \text{MIII}$$

$$R^7—Ar^4—R^8 \quad \text{MIV}$$

wherein
U a unit of formula I1 or I2,
$Ar^{1-4}$ arylene or heteroarylene that is different from U, has 5 to 30 ring atoms, and is optionally substituted by one or more groups L,
a, b, c and d are 0 or 1, and
$R^7$ and $R^8$ are each independently an activated C—H bond, Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ or —Sn(Z$^4$)$_3$, wherein X$^0$ is halogen, Z$^{1-4}$ are C$_{1-10}$ alkyl or C$_{6-12}$ aryl, each being optionally substituted, and two groups Z$^2$ may also form a cycloboronate group having 2 to 20 C atoms together with the B- and O-atoms.

\* \* \* \* \*